US005908970A

United States Patent [19]
Van Mellaert et al.

[11] Patent Number: 5,908,970
[45] Date of Patent: Jun. 1, 1999

[54] RECOMBINANT PLANT EXPRESSING NON-COMPETITIVELY BINDING BT INSECTICIDAL CRYSTAL PROTEINS

[75] Inventors: Herman Van Mellaert, Leuven; Johan Botterman, Zevergem-de Pinte; Jeroen Van Rie, Eeklo; Henk Joos, Aalter, all of Belgium

[73] Assignee: Plant Genetic Systems N.V.

[ * ] Notice: This patent is subject to a terminal disclaimer.

[21] Appl. No.: 08/463,240

[22] Filed: Jun. 5, 1995

Related U.S. Application Data

[62] Division of application No. 08/173,274, Dec. 23, 1993, abandoned, which is a continuation of application No. 07/640,400, filed as application No. PCT/EP90/00905, May 30, 1990, abandoned.

[30] Foreign Application Priority Data

May 31, 1989 [GB] United Kingdom ................. 89401499

[51] Int. Cl.⁶ ............................... A01H 5/00; A01H 5/10; C12N 15/32; C12N 15/82
[52] U.S. Cl. .................. 800/205; 435/172.3; 435/320.1; 435/419; 536/23.71; 800/250
[58] Field of Search ..................................... 800/205, 250; 435/240.4, 172.3, 320.1, 419; 536/23.71

[56] References Cited

FOREIGN PATENT DOCUMENTS

| 0192319 | 8/1986 | European Pat. Off. . |
| 0193259 | 9/1986 | European Pat. Off. . |
| 0221024 | 5/1987 | European Pat. Off. . |
| 0228838 | 7/1987 | European Pat. Off. . |
| 305275 | 3/1989 | European Pat. Off. . |
| 88/08880 | 11/1988 | WIPO . |

OTHER PUBLICATIONS

"Specificity of *Bacillus thuringiensis* delta–endotoxins is correlated with the presence of high–affinity binding sites in the brush border membrane of traget insect midgut", *Proc. Natl. Acad. Sci.*, vol. 85, (1988), pp. 7844–7848.

"Chimera insecticidal protein of *Bacillus thuringiensis*", *Patent Abstracts of Japan*, vol. 12, No. 391, (1988), (C–537).

Aronson et al. *Microbiol. Reviews*, Mar. 1986, vol. 50, No. 1, pp. 1–24.

M. DeBlock, *The EMBO Journal*, vol. 6, No. 9, pp. 2513–2518, (1987).

Gasser et al., *Science*, vol. 244, Jun. 16, 1989, pp. 1293–1299.

van der Salm, et al., *Plant Molecular Biology*, vol. 25, pp. 51–59, (1994).

Chungjatupornchai, et al., *Eur. J. Biochem.*, vol. 173, pp. 9–16 (1988).

Adang, et al., *Gene*, vol. 36, pp. 289–300 (1985).

Hofte, et al., *Eur. J. Biochem.*, vol. 161, pp. 273–280 (1986).

Schnepf, et al., *Journal of Biological Chemistry*, vol. 260, No. 1, Issue of May 25, 1985, pp. 6273–6280.

McPherson, et al., *Biotechnology*, vol. 6, Jan. 1988, pp. 61–66.

Hofte et al., *Microbiological Reviews*, vol. 53, No. 2, Jun. 1989, pp. 242–255.

Perlak, et al., *Biotechnology*, vol. 8, Oct. 1990, pp. 939–943.

Rie, et al., *Science*, vol. 247, Jan. 5, 1990, pp. 72–74.

"Current Uses and Future Prospects for Microbial Pest Control Agents", *Med. Fac. Landbouww. Rijksuniv.*, Gent, 52(2a), 1987, pp. 113–123, C. Payne.

"The Binding of *Bacillus thuringiensis* delta–endotoxin to cultured insect cells and to brush border membrane vesicles", Diss. ETH No. 8498, Christina Hofmann. 1988.

"Evolution of Resistance in the Presence of Two Insecticides", *The Genetics Society of America*, G. Mani, Nov. 1984, pp. 761–783.

"Binding of Different Types of *Bacillus Thuringiensis* Delta–Endotoxins to Midgut Brush Border Membrane Vesicles is Correlated with the Insecticidal Spectrum", Van Mellaert et al., XXI Annual Meeting of the Society for Inveertebrate Pathology at the University of California, San Diego at La Jolla on Aug. 14–18, 1988.

Hofmann (1988) Ph.D. Thesis Swiss Federal Institute of Technology, Zurich, Diss ETH No. 8498.

Mani (1985) Genetics 109: 761–783.
Vaeck, et al. (1987) Nature 328: 33–37.

*Primary Examiner*—Douglas W. Robinson
*Assistant Examiner*—Amy J. Nelson
*Attorney, Agent, or Firm*—Burns, Doane, Swecker & Mathis, L.L.P.

[57] ABSTRACT

Plants made resistant to insects by transforming their nuclear genome with two or more DNA sequences, each encoding a different non-competitively binding *B. thuringiensis* protoxin or insecticidal part thereof, preferably the toxin thereof.

21 Claims, 54 Drawing Sheets

```
        10         20         30         40         50
GGATCTGTTT TAATATAAGG GATTTGTGCC CTTCTCGTTA TATTCTTTTA 60         70         80         90        100
TTAGCCCCAA AAACTAGTGC AACTAAATAT TTTTATAATT ACACTGATTA 110        120        130        140        150
AATACTTTAT TTTTGGGAGT AAGATTTATG CTGAAATGTA ATAAAATTCG 160        170        180        190        200
TTCCATTTTC TGTATTTTCT CATAAAATGT TTCATATGCT TTAAATTGTA 210        220        230        240        250
GTAAAGAAAA ACAGTACAAA CTTAAAGGA CTTTAGTAAT TTAATAAAAA 260        269        278        287
AAGGGGATAG TTT ATG GAA ATA AAT AAT CAA AAC CAA TGT
           MET Glu Ile Asn Asn Gln Asn Gln Cys
```

FIG. 13A

```
        296             305             314             323
GTG CCT TAC AAT TGT TTA AGT AAT CCT AAG GAG ATA ATA
Val Pro Tyr Asn Cys Leu Ser Asn Pro Lys Glu Ile Ile 332             341             350             359             368
TTA GGC GAG GAA AGG CTA GAA ACA GGG AAT ACT GTA GCA
Leu Gly Glu Glu Arg Leu Glu Thr Gly Asn Thr Val Ala 377             386             395             404
GAC ATT TCA TTA GGG CTT ATT AAT TTT CTA TAT TCT AAT
Asp Ile Ser Leu Gly Leu Ile Asn Phe Leu Tyr Ser Asn 413             422             431             440
TTT GTA CCA GGA GGA GGA TTT ATA GTA GGT TTA CTA GAA
Phe Val Pro Gly Gly Gly Phe Ile Val Gly Leu Leu Glu 449             458             467             476             485
TTA ATA TGG GGA TTT ATA GGG CCT TCG CAA TGG GAT ATT
Leu Ile Trp Gly Phe Ile Gly Pro Ser Gln Trp Asp Ile 494             503             512             521
TTT TTA GCT CAA ATT GAG CAA TTG ATT AGT CAA AGA ATA
Phe Leu Ala Gln Ile Glu Gln Leu Ile Ser Gln Arg Ile
```

FIG. 13B

```
      530         539         548         557
GAA GAA TTT GCT AGG AAT CAG GCA ATT TCA AGA TTG GAG
Glu Glu Phe Ala Arg Asn Gln Ala Ile Ser Arg Leu Glu 566         575         584         593         602
GGG CTA AGC AAT CTT TAT AAG GTC TAT GTT AGA GCG TTT
Gly Leu Ser Asn Leu Tyr Lys Val Tyr Val Arg Ala Phe 611         620         629         638
AGC GAC TGG GAG AAA GAT CCT ACT AAT CCT GCT TTA AGG
Ser Asp Trp Glu Lys Asp Pro Thr Asn Pro Ala Leu Arg 647         656         665         674
GAA GAA ATG CGT ATA CAA TTT AAT GAC ATG AAT AGT GCT
Glu Glu MET Arg Ile Gln Phe Asn Asp MET Asn Ser Ala 683         692         701         710         719
CTC ATA ACG GCT ATT CCA CTT TTT AGA GTT CAA AAT TAT
Leu Ile Thr Ala Ile Pro Leu Phe Arg Val Gln Asn Tyr 728         737         746         755
GAA GTT GCT CTT TTA TCT GTA TAT GTT CAA GCC GCA AAC
Glu Val Ala Leu Leu Ser Val Tyr Val Gln Ala Ala Asn
```

FIG. 13C

```
    764             773             782             791
TTA CAT TTA TCT ATT TTA AGG GAT GTT TCA GTT TTC GGA
Leu His Leu Ser Ile Leu Arg Asp Val Ser Val Phe Gly 800             809             818             827             836
GAA AGA TGG GGA TAT GAT ACA GCG ACT ATC AAT AAT CGC
Glu Arg Trp Gly Tyr Asp Thr Ala Thr Ile Asn Asn Arg 845             854             863             872
TAT AGT GAT CTG ACT AGC CTT ATT CAT GTT TAT ACT AAC
Tyr Ser Asp Leu Thr Ser Leu Ile His Val Tyr Thr Asn 881             890             899             908
CAT TGT GTG GAT ACG TAT AAT CAG GGA TTA AGG CGT TTG
His Cys Val Asp Thr Tyr Asn Gln Gly Leu Arg Arg Leu 917             926             935             944             953
GAA GGT CGT TTT CTT AGC GAT TGG ATT GTA TAT AAT CGT
Glu Gly Arg Phe Leu Ser Asp Trp Ile Val Tyr Asn Arg 962             971             980             989
TTC CGG AGA CAA TTG ACA ATT TCA GTA TTA GAT ATT GTT
Phe Arg Arg Gln Leu Thr Ile Ser Val Leu Asp Ile Val
```

FIG. 13D

```
        998         1007        1016        1025
  GCG TTT TTT CCA AAT TAT GAT ATT AGA ACA TAT CCA ATT
  Ala Phe Phe Pro Asn Tyr Asp Ile Arg Thr Tyr Pro Ile 1034        1043        1052        1061        1070
  CAA ACA GCT ACT CAG CTA ACG AGG GAA GTC TAT CTG GAT
  Gln Thr Ala Thr Gln Leu Thr Arg Glu Val Tyr Leu Asp 1079        1088        1097        1106
  TTA CCT TTT ATT AAT GAA AAT CTT TCT CCT GCA GCA AGC
  Leu Pro Phe Ile Asn Glu Asn Leu Ser Pro Ala Ala Ser 1115        1124        1133        1142
  TAT CCA ACC TTT TCA GCT GCT GAA AGT GCT ATA ATT AGA
  Tyr Pro Thr Phe Ser Ala Ala Glu Ser Ala Ile Ile Arg 1151        1160        1169        1178        1187
  AGT CCT CAT TTA GTA GAC TTT TTA AAT AGC TTT ACC ATT
  Ser Pro His Leu Val Asp Phe Leu Asn Ser Phe Thr Ile 1196        1205        1214        1223
  TAT ACA GAT AGT CTG GCA CGT TAT GCA TAT TGG GGA GGG
  Tyr Thr Asp Ser Leu Ala Arg Tyr Ala Tyr Trp Gly Gly
```

FIG. 13E

```
1232        1241        1250        1259
CAC TTG GTA AAT TCT TTC CGC ACA GGA ACC ACT ACT AAT
His Leu Val Asn Ser Phe Arg Thr Gly Thr Thr Thr Asn 1268        1277        1286        1295        1304
TTG ATA AGA TCC CCT TTA TAT GGA AGG GAA GGA AAT ACA
Leu Ile Arg Ser Pro Leu Tyr Gly Arg Glu Gly Asn Thr 1313        1322        1331        1340
GAG CGC CCC GTA ACT ATT ACC GCA TCA CCT AGC GTA CCA
Glu Arg Pro Val Thr Ile Thr Ala Ser Pro Ser Val Pro 1349        1358        1367        1376
ATA TTT AGA ACA CTT TCA TAT ATT ACA GGC CTT GAC AAT
Ile Phe Arg Thr Leu Ser Tyr Ile Thr Gly Leu Asp Asn 1385        1394        1403        1412        1421
TCA AAT CCT GTA GCT GGA ATC GAG GGA GTG GAA TTC CAA
Ser Asn Pro Val Ala Gly Ile Glu Gly Val Glu Phe Gln 1430        1439        1448        1457
AAT ACT ATA AGT AGA AGT ATC TAT CGT AAA AGC GGT CCA
Asn Thr Ile Ser Arg Ser Ile Tyr Arg Lys Ser Gly Pro
```

FIG. 13F

```
    1466        1475        1484        1493
ATA GAT TCT TTT AGT GAA TTA CCA CCT CAA GAT GCC AGC
Ile Asp Ser Phe Ser Glu Leu Pro Pro Gln Asp Ala Ser 1502        1511        1520        1529        1538
GTA TCT CCT GCA ATT GGG TAT AGT CAC CGT TTA TGC CAT
Val Ser Pro Ala Ile Gly Tyr Ser His Arg Leu Cys His 1547        1556        1565        1574
GCA ACA TTT TTA GAA CGG ATT AGT GGA CCA AGA ATA GCA
Ala Thr Phe Leu Glu Arg Ile Ser Gly Pro Arg Ile Ala 1583        1592        1601        1610
GGC ACC GTA TTT TCT TGG ACA CAC CGT AGT GCC AGC CCT
Gly Thr Val Phe Ser Trp Thr His Arg Ser Ala Ser Pro 1619        1628        1637        1646        1655
ACT AAT GAA GTA AGT CCA TCT AGA ATT ACA CAA ATT CCA
Thr Asn Glu Val Ser Pro Ser Arg Ile Thr Gln Ile Pro 1664        1673        1682        1691
TGG GTA AAG GCG CAT ACT CTT GCA TCT GGT GCC TCC GTC
Trp Val Lys Ala His Thr Leu Ala Ser Gly Ala Ser Val
```

FIG. 13G

```
   1700         1709         1718         1727
ATT AAA GGT CCT GGA TTT ACA GGT GGA GAT ATT CTG ACT
Ile Lys Gly Pro Gly Phe Thr Gly Gly Asp Ile Leu Thr 1736         1745         1754         1763         1772
AGG AAT AGT ATG GGC GAG CTG GGG ACC TTA CGA GTA ACC
Arg Asn Ser MET Gly Glu Leu Gly Thr Leu Arg Val Thr 1781         1790         1799         1808
TTC ACA GGA AGA TTA CCA CAA AGT TAT TAT ATA CGT TTC
Phe Thr Gly Arg Leu Pro Gln Ser Tyr Tyr Ile Arg Phe 1817         1826         1835         1844
CGT TAT GCT TCG GTA GCA AAT AGG AGT GGT ACA TTT AGA
Arg Tyr Ala Ser Val Ala Asn Arg Ser Gly Thr Phe Arg 1853         1862         1871         1880         1889
TAT TCA CAG CCA CCT TCG TAT GGA ATT TCA TTT CCA AAA
Tyr Ser Gln Pro Pro Ser Tyr Gly Ile Ser Phe Pro Lys 1898         1907         1916         1925
ACT ATG GAC GCA GGT GAA CCA CTA ACA TCT CGT TCG TTC
Thr MET Asp Ala Gly Glu Pro Leu Thr Ser Arg Ser Phe
```

FIG. 13H

```
     1934        1943        1952        1961
  GCT CAT ACA ACA CTC TTC ACT CCA ATA ACC TTT TCA CGA
  Ala His Thr Thr Leu Phe Thr Pro Ile Thr Phe Ser Arg 1970        1979        1988        1997        2006
  GCT CAA GAA GAA TTT GAT CTA TAC ATC CAA TCG GGT GTT
  Ala Gln Glu Glu Phe Asp Leu Tyr Ile Gln Ser Gly Val
                                                  ---
        2015        2024        2033        2042
  TAT ATA GAT CGA ATT GAA TTT ATA CCG GTT ACT GCA ACA
  Tyr Ile Asp Arg Ile Glu Phe Ile Pro Val Thr Ala Thr
  ---------------------------------------------------->
        2051        2060        2069        2078
  TTT GAG GCA GAA TAT GAT TTA GAA AGA GCG CAA AAG GTG
  Phe Glu Ala Glu Tyr Asp Leu Glu Arg Ala Gln Lys Val 2087        2096        2105        2114        2123
  GTG AAT GCC CTG TTT ACG TCT ACA AAC CAA CTA GGG CTA
  Val Asn Ala Leu Phe Thr Ser Thr Asn Gln Leu Gly Leu 2132        2141        2150        2159
  AAA ACA GAT GTG ACG GAT TAT CAT ATT GAT CAG GTA TCC
  Lys Thr Asp Val Thr Asp Tyr His Ile Asp Gln Val Ser
```

FIG. 13I

```
      2168        2177        2186         2195
AAT CTA GTT GCG TGT TTA TCG GAT GAA TTT TGT CTG GAT
Asn Leu Val Ala Cys Leu Ser Asp Glu Phe Cys Leu Asp 2204        2213        2222        2231         2240
GAA AAG AGA GAA TTG TCC GAG AAA GTT AAA CAT GCA AAG
Glu Lys Arg Glu Leu Ser Glu Lys Val Lys His Ala Lys 2249        2258        2267         2276
CGA CTC AGT GAT GAG CGG AAT TTA CTT CAA GAT CCA AAC
Arg Leu Ser Asp Glu Arg Asn Leu Leu Gln Asp Pro Asn 2285        2294        2303         2312
TTC AGA GGG ATC AAT AGG CAA CCA GAC CGT GGC TGG AGA
Phe Arg Gly Ile Asn Arg Gln Pro Asp Arg Gly Trp Arg 2321        2330        2339        2348         2357
GGA AGT ACG GAT ATT ACT ATC CAA GGA GGA GAT GAC GTA
Gly Ser Thr Asp Ile Thr Ile Gln Gly Gly Asp Asp Val 2366        2375        2384         2393
TTC AAA GAG AAT TAC GTT ACG CTA CCG GGT ACC TTT GAT
Phe Lys Glu Asn Tyr Val Thr Leu Pro Gly Thr Phe Asp
```

FIG. 13J

```
         2402          2411          2420          2429
      GAG TGC TAT CCA ACG TAT TTA TAT CAA AAA ATA GAT GAG
      Glu Cys Tyr Pro Thr Tyr Leu Tyr Gln Lys Ile Asp Glu 2438         2447          2456          2465          2474
      TCG AAA TTA AAA GCC TAT ACC CGT TAT CAA TTA AGA GGG
      Ser Lys Leu Lys Ala Tyr Thr Arg Tyr Gln Leu Arg Gly 2483          2492          2501          2510
      TAT ATC GAA GAT AGT CAA GAC TTA GAA ATC TAT TTA ATT
      Tyr Ile Glu Asp Ser Gln Asp Leu Glu Ile Tyr Leu Ile 2519          2528          2537          2546
      CGT TAC AAT GCA AAA CAC GAA ATA GTA AAT GTA CCA GGT
      Arg Tyr Asn Ala Lys His Glu Ile Val Asn Val Pro Gly 2555         2564          2573          2582          2591
      ACA GGA AGT TTA TGG CCT CTT TCT GTA GAA AAT CAA ATT
      Thr Gly Ser Leu Trp Pro Leu Ser Val Glu Asn Gln Ile 2600          2609          2618          2627
      GGA CCT TGT GGA GAA CCG AAT CGA TGC GCG CCA CAC CTT
      Gly Pro Cys Gly Glu Pro Asn Arg Cys Ala Pro His Leu
```

FIG. 13K

```
      2636        2645        2654        2663
 GAA TGG AAT CCT GAT TTA CAC TGT TCC TGC AGA GAC GGG
 Glu Trp Asn Pro Asp Leu His Cys Ser Cys Arg Asp Gly 2672        2681        2690        2699        2708
 GAA AAA TGT GCA CAT CAT TCT CAT CAT TTC TCT TTG GAC
 Glu Lys Cys Ala His His Ser His His Phe Ser Leu Asp 2717        2726        2735        2744
 ATT GAT GTT GGA TGT ACA GAC TTA AAT GAG GAC TTA GGT
 Ile Asp Val Gly Cys Thr Asp Leu Asn Glu Asp Leu Gly 2753        2762        2771        2780
 GTA TGG GTG ATA TTC AAG ATT AAG ACG CAA GAT GGC CAC
 Val Trp Val Ile Phe Lys Ile Lys Thr Gln Asp Gly His 2789        2798        2807        2816        2825
 GCA CGA CTA GGG AAT CTA GAG TTT CTC GAA GAG AAA CCA
 Ala Arg Leu Gly Asn Leu Glu Phe Leu Glu Glu Lys Pro 2834        2843        2852        2861
 TTA TTA GGA GAA GCA CTA GCT CGT GTG AAA AGA GCG GAG
 Leu Leu Gly Glu Ala Leu Ala Arg Val Lys Arg Ala Glu
```

FIG. 13L

```
              2870        2879        2888        2897
            AAA AAA TGG AGA GAC AAA CGC GAA ACA TTA CAA TTG GAA
            Lys Lys Trp Arg Asp Lys Arg Glu Thr Leu Gln Leu Glu 2906        2915        2924        2933        2942
   ACA ACT ATC GTT TAT AAA GAG GCA AAA GAA TCT GTA GAT
   Thr Thr Ile Val Tyr Lys Glu Ala Lys Glu Ser Val Asp 2951        2960        2969        2978
            GCT TTA TTT GTA AAC TCT CAA TAT GAT AGA TTA CAA GCG
            Ala Leu Phe Val Asn Ser Gln Tyr Asp Arg Leu Gln Ala 2987        2996        3005        3014
            GAT ACG AAC ATC GCG ATG ATT CAT GCG GCA GAT AAA CGC
            Asp Thr Asn Ile Ala MET Ile His Ala Ala Asp Lys Arg 3023        3032        3041        3050        3059
   GTT CAT AGA ATT CGA GAA GCG TAT CTG CCG GAG CTG TCT
   Val His Arg Ile Arg Glu Ala Tyr Leu Pro Glu Leu Ser 3068        3077        3086        3095
            GTG ATT CCG GGT GTC AAT GCG GCT ATT TTT GAA GAA TTA
            Val Ile Pro Gly Val Asn Ala Ala Ile Phe Glu Glu Leu
```

FIG. 13M

```
                3104         3113         3122         3131
        GAA GAG CGT ATT TTC ACT GCA TTT TCC CTA TAT GAT GCG
        Glu Glu Arg Ile Phe Thr Ala Phe Ser Leu Tyr Asp Ala 3140         3149         3158         3167         3176
        AGA AAT ATT ATT AAA AAT GGC GAT TTC AAT AAT GGC TTA
        Arg Asn Ile Ile Lys Asn Gly Asp Phe Asn Asn Gly Leu 3185         3194         3203         3212
        TTA TGC TGG AAC GTG AAA GGG CAT GTA GAG GTA GAA GAA
        Leu Cys Trp Asn Val Lys Gly His Val Glu Val Glu Glu 3221         3230         3239         3248
        CAA AAC AAT CAC CGT TCA GTC CTG GTT ATC CCA GAA TGG
        Gln Asn Asn His Arg Ser Val Leu Val Ile Pro Glu Trp 3257         3266         3275         3284         3293
        GAG GCA GAA GTG TCA CAA GAG GTT CGT GTC TGT CCA GGT
        Glu Ala Glu Val Ser Gln Glu Val Arg Val Cys Pro Gly 3302         3311         3320         3329
        CGT GGC TAT ATC CTT CGT GTT ACA GCG TAC AAA GAG GGA
        Arg Gly Tyr Ile Leu Arg Val Thr Ala Tyr Lys Glu Gly
```

FIG. 13N

```
       3338        3347        3356        3365
 TAT GGA GAA GGT TGC GTA ACG ATC CAT GAG ATC GAG AAC
 Tyr Gly Glu Gly Cys Val Thr Ile His Glu Ile Glu Asn 3374        3383        3392        3401        3410
 AAT ACA GAC GAA CTG AAA TTC AAC AAC TGT GTA GAA GAG
 Asn Thr Asp Glu Leu Lys Phe Asn Asn Cys Val Glu Glu 3419        3428        3437        3446
     GAA GTA TAT CCA AAC AAC ACG GTA ACG TGT ATT AAT TAT
     Glu Val Tyr Pro Asn Asn Thr Val Thr Cys Ile Asn Tyr 3455        3464        3473        3482
 ACT GCG ACT CAA GAA GAA TAT GAG GGT ACG TAC ACT TCT
 Thr Ala Thr Gln Glu Glu Tyr Glu Gly Thr Tyr Thr Ser 3491        3500        3509        3518        3527
 CGT AAT CGA GGA TAT GAC GAA GCC TAT GGT AAT AAC CCT
 Arg Asn Arg Gly Tyr Asp Glu Ala Tyr Gly Asn Asn Pro 3536        3545        3554        3563
 TCC GTA CCA GCT GAT TAT GCG TCA GTC TAT GAA GAA AAA
 Ser Val Pro Ala Asp Tyr Ala Ser Val Tyr Glu Glu Lys
```

FIG. 13O

```
       3572          3581          3590          3599
  TCG TAT ACA GAT AGA CGA AGA GAG AAT CCT TGT GAA TCT
  Ser Tyr Thr Asp Arg Arg Arg Glu Asn Pro Cys Glu Ser 3608          3617          3626          3635          3644
  AAC AGA GGA TAT GGA GAT TAC ACA CCA CTA CCA GCT GGT
  Asn Arg Gly Tyr Gly Asp Tyr Thr Pro Leu Pro Ala Gly 3653          3662          3671          3680
  TAT GTA ACA AAG GAA TTA GAG TAC TTC CCA GAG ACC GAT
  Tyr Val Thr Lys Glu Leu Glu Tyr Phe Pro Glu Thr Asp 3689          3698          3707          3716
  AAG GTA TGG ATT GAG ATT GGA GAA ACA GAA GGA ACA TTC
  Lys Val Trp Ile Glu Ile Gly Glu Thr Glu Gly Thr Phe 3725          3734          3743          3752          3761
  ATC GTG GAC AGC GTG GAA TTA CTC CTT ATG GAG GAA TAG
  Ile Val Asp Ser Val Glu Leu Leu Leu MET Glu Glu
```

FIG. 13P

```
        3771       3781       3791       3801       3811
   GACCATCCGA GTATAGCAGT TTAATAAATA TTAATTAAAA TAGTAGTCTA 3821       3831       3841       3851       3861
   ACTTCCGTTC CAATTAAATA AGTAAATTAC AGTTGTAAAA AAAAACGAAC 3871       3881       3891       3901
   ATTACTCTTC AAAGAGCGAT GTCCGTTTTT TATATGGTGT GT
```

FIG. 13Q

```
           10         20         30         40         50
AATAGAATCT CAAATCTCGA TGACTGCTTA GTCTTTTTAA TACTGTCTAC 60         70         80         90        100
TTGACAGGGG TAGGAACATA ATCGGTCAAT TTTAAATATG GGCATATAT 110        120        130        140        150
TGATATTTTA TAAAATTTGT TACGTTTTTT GTATTTTTTC ATAAGATGTG 160        170        180        190        200
TCATATGTAT TAAATCGTGG TAATGAAAAA CAGTATCAAA CTATCAGAAC 210        220        230    239
TTTGGTAGTT TAATAAAAAA ACGGAGGTAT TTT ATG GAG GAA
                                  ----- MET Glu Glu 248         257         266         275
AAT AAT CAA AAT CAA TGC ATA CCT TAC AAT TGT TTA AGT
Asn Asn Gln Asn Gln Cys Ile Pro Tyr Asn Cys Leu Ser 284         293         302         311         320
AAT CCT GAA GAA GTA CTT TTG GAT GGA GAA CGG ATA TCA
Asn Pro Glu Glu Val Leu Leu Asp Gly Glu Arg Ile Ser
```

FIG. 14A

```
      329         338         347         356
ACT GGT AAT TCA TCA ATT GAT ATT TCT CTG TCA CTT GTT
Thr Gly Asn Ser Ser Ile Asp Ile Ser Leu Ser Leu Val 365         374         383         392
CAG TTT CTG GTA TCT AAC TTT GTA CCA GGG GGA GGA TTT
Gln Phe Leu Val Ser Asn Phe Val Pro Gly Gly Gly Phe 401         410         419         428         437
TTA GTT GGA TTA ATA GAT TTT GTA TGG GGA ATA GTT GGC
Leu Val Gly Leu Ile Asp Phe Val Trp Gly Ile Val Gly 446         455         464         473
CCT TCT CAA TGG GAT GCA TTT CTA GTA CAA ATT GAA CAA
Pro Ser Gln Trp Asp Ala Phe Leu Val Gln Ile Glu Gln 482         491         500         509
TTA ATT AAT GAA AGA ATA GCT GAA TTT GCT AGG AAT GCT
Leu Ile Asn Glu Arg Ile Ala Glu Phe Ala Arg Asn Ala 518         527         536         545         554
GCT ATT GCT AAT TTA GAA GGA TTA GGA AAC AAT TTC AAT
Ala Ile Ala Asn Leu Glu Gly Leu Gly Asn Asn Phe Asn
```

FIG. 14B

```
       563         572         581         590
ATA TAT GTG GAA GCA TTT AAA GAA TGG GAA GAA GAT CCT
Ile Tyr Val Glu Ala Phe Lys Glu Trp Glu Glu Asp Pro 599         608         617         626
AAT AAT CCA GAA ACC AGG ACC AGA GTA ATT GAT CGC TTT
Asn Asn Pro Glu Thr Arg Thr Arg Val Ile Asp Arg-Phe 635         644         653         662         671
CGT ATA CTT GAT GGG CTA CTT GAA AGG GAC ATT CCT TCG
Arg Ile Leu Asp Gly Leu Leu Glu Arg Asp Ile Pro Ser 680         689         698         707
TTT CGA ATT TCT GGA TTT GAA GTA CCC CTT TTA TCC GTT
Phe Arg Ile Ser Gly Phe Glu Val Pro Leu Leu Ser Val 716         725         734         743
TAT GCT CAA GCG GCC AAT CTG CAT CTA GCT ATA TTA AGA
Tyr Ala Gln Ala Ala Asn Leu His Leu Ala Ile Leu Arg 752         761         770         779         788
GAT TCT GTA ATT TTT GGA GAA AGA TGG GGA TTG ACA ACG
Asp Ser Val Ile Phe Gly Glu Arg Trp Gly Leu Thr Thr
```

FIG. 14C

```
        797              806              815              824
ATA AAT GTC AAT GAA AAC TAT AAT AGA CTA ATT AGG CAT
Ile Asn Val Asn Glu Asn Tyr Asn Arg Leu Ile Arg His 833              842              851              860
ATT GAT GAA TAT GCT GAT CAC TGT GCA AAT ACG TAT AAT
Ile Asp Glu Tyr Ala Asp His Cys Ala Asn Thr Tyr Asn 869              878              887              896              905
CGG GGA TTA AAT AAT TTA CCG AAA TCT ACG TAT CAA GAT
Arg Gly Leu Asn Asn Leu Pro Lys Ser Thr Tyr Gln Asp 914              923              932              941
TGG ATA ACA TAT AAT CGA TTA CGG AGA GAC TTA ACA TTG
Trp Ile Thr Tyr Asn Arg Leu Arg Arg Asp Leu Thr Leu 950              959              968              977
ACT GTA TTA GAT ATC GCC GCT TTC TTT CCA AAC TAT GAC
Thr Val Leu Asp Ile Ala Ala Phe Phe Pro Asn Tyr Asp 986              995              1004             1013             1022
AAT AGG AGA TAT CCA ATT CAG CCA GTT GGT CAA CTA ACA
Asn Arg Arg Tyr Pro Ile Gln Pro Val Gly Gln Leu Thr
```

FIG. 14D

```
      1031        1040        1049        1058
   AGG GAA GTT TAT ACG GAC CCA TTA ATT AAT TTT AAT CCA
   Arg Glu Val Tyr Thr Asp Pro Leu Ile Asn Phe Asn Pro 1067        1076        1085        1094
   CAG TTA CAG TCT GTA GCT CAA TTA CCT ACT TTT AAC GTT
   Gln Leu Gln Ser Val Ala Gln Leu Pro Thr Phe Asn Val 1103       1112        1121        1130        1139
   ATG GAG AGC AGC GCA ATT AGA AAT CCT CAT TTA TTT GAT
   MET Glu Ser Ser Ala Ile Arg Asn Pro His Leu Phe Asp 1148        1157        1166        1175
   ATA TTG AAT AAT CTT ACA ATC TTT ACG GAT TGG TTT AGT
   Ile Leu Asn Asn Leu Thr Ile Phe Thr Asp Trp Phe Ser 1184        1193        1202        1211
   GTT GGA CGC AAT TTT TAT TGG GGA GGA CAT CGA GTA ATA
   Val Gly Arg Asn Phe Tyr Trp Gly Gly His Arg Val Ile 1220       1229        1238        1247        1256

TCT AGC CTT ATA GGA GGT GGT AAC ATA ACA TCT CCT ATA
   Ser Ser Leu Ile Gly Gly Gly Asn Ile Thr Ser Pro Ile
```

FIG. 14E

```
           1265           1274           1283           1292
     TAT GGA AGA GAG GCG AAC CAG GAG CCT CCA AGA TCC TTT
     Tyr Gly Arg Glu Ala Asn Gln Glu Pro Pro Arg Ser Phe 1301           1310           1319           1328
     ACT TTT AAT GGA CCG GTA TTT AGG ACT TTA TCA AAT CCT
     Thr Phe Asn Gly Pro Val Phe Arg Thr Leu Ser Asn Pro 1337           1346           1355           1364           1373
     ACT TTA CGA TTA TTA CAG CAA CCT TGG CCA GCG CCA CCA
     Thr Leu Arg Leu Leu Gln Gln Pro Trp Pro Ala Pro Pro 1382           1391           1400           1409
     TTT AAT TTA CGT GGT GTT GAA GGA GTA GAA TTT TCT ACA
     Phe Asn Leu Arg Gly Val Glu Gly Val Glu Phe Ser Thr 1418           1427           1436           1445
     CCT ACA AAT AGC TTT ACG TAT CGA GGA AGA GGT ACG GTT
     Pro Thr Asn Ser Phe Thr Tyr Arg Gly Arg Gly Thr Val 1454           1463           1472           1481           1490
     GAT TCT TTA ACT GAA TTA CCG CCT GAG GAT AAT AGT GTG
     Asp Ser Leu Thr Glu Leu Pro Pro Glu Asp Asn Ser Val
```

FIG. 14F

```
      1499        1508        1517        1526
CCA CCT CGC GAA GGA TAT AGT CAT CGT TTA TGT CAT GCA
Pro Pro Arg Glu Gly Tyr Ser His Arg Leu Cys His Ala 1535        1544        1553        1562
ACT TTT GTT CAA AGA TCT GGA ACA CCT TTT TTA ACA ACT
Thr Phe Val Gln Arg Ser Gly Thr Pro Phe Leu Thr Thr 1571        1580        1589        1598        1607
GGT GTA GTA TTT TCT TGG ACG CAT CGT AGT GCA ACT CTT
Gly Val Val Phe Ser Trp Thr His Arg Ser Ala Thr Leu 1616        1625        1634        1643
ACA AAT ACA ATT GAT CCA GAG AGA ATT AAT CAA ATA CCT
Thr Asn Thr Ile Asp Pro Glu Arg Ile Asn Gln Ile Pro 1652        1661        1670        1679
TTA GTG AAA GGA TTT AGA GTT TGG GGG GGC ACC TCT GTC
Leu Val Lys Gly Phe Arg Val Trp Gly Gly Thr Ser Val 1688        1697        1706        1715        1724
ATT ACA GGA CCA GGA TTT ACA GGA GGG GAT ATC CTT CGA
Ile Thr Gly Pro Gly Phe Thr Gly Gly Asp Ile Leu Arg
```

FIG. 14G

```
        1733        1742          1751         1760
AGA AAT ACC TTT GGT GAT TTT GTA TCT CTA CAA GTC AAT
Arg Asn Thr Phe Gly Asp Phe Val Ser Leu Gln Val Asn 1769        1778          1787         1796
ATT AAT TCA CCA ATT ACC CAA AGA TAC CGT TTA AGA TTT
Ile Asn Ser Pro Ile Thr Gln Arg Tyr Arg Leu Arg Phe 1805        1814          1823         1832         1841
CGT TAC GCT TCC AGT AGG GAT GCA CGA GTT ATA GTA TTA
Arg Tyr Ala Ser Ser Arg Asp Ala Arg Val Ile Val Leu 1850          1859         1868         1877
ACA GGA GCG GCA TCC ACA GGA GTG GGA GGC CAA GTT AGT
Thr Gly Ala Ala Ser Thr Gly Val Gly Gly Gln Val Ser 1886          1895         1904         1913
GTA AAT ATG CCT CTT CAG AAA ACT ATG GAA ATA GGG GAG
Val Asn MET Pro Leu Gln Lys Thr MET Glu Ile Gly Glu 1922         1931          1940         1949         1958
AAC TTA ACA TCT AGA ACA TTT AGA TAT ACC GAT TTT AGT
Asn Leu Thr Ser Arg Thr Phe Arg Tyr Thr Asp Phe Ser
```

FIG. 14H

```
                1967        1976        1985        1994
        AAT CCT TTT TCA TTT AGA GCT AAT CCA GAT ATA ATT GGG
        Asn Pro Phe Ser Phe Arg Ala Asn Pro Asp Ile Ile Gly 2003        2012        2021        2030
        ATA AGT GAA CAA CCT CTA TTT GGT GCA GGT TCT ATT AGT
        Ile Ser Glu Gln Pro Leu Phe Gly Ala Gly Ser Ile Ser 2039        2048        2057        2066        2075
    AGC GGT GAA CTT TAT ATA GAT AAA ATT GAA ATT ATT CTA
    Ser Gly Glu Leu Tyr Ile Asp Lys Ile Glu Ile Ile Leu 2084        2093        2102        2111
        GCA GAT GCA ACA TTT GAA GCA GAA TCT GAT TTA GAA AGA
        Ala Asp Ala Thr Phe Glu Ala Glu Ser Asp Leu Glu Arg 2120        2129        2138        2147
        GCA CAA AAG GCG GTG AAT GCC CTG TTT ACT TCT TCC AAT
        Ala Gln Lys Ala Val Asn Ala Leu Phe Thr Ser Ser Asn 2156        2165        2174        2183        2192
    CAA ATC GGG TTA AAA ACC GAT GTG ACG GAT TAT CAT ATT
    Gln Ile Gly Leu Lys Thr Asp Val Thr Asp Tyr His Ile
```

FIG. 14I

```
2201        2210        2219        2228
GAT CAA GTA TCC AAT TTA GTG GAT TGT TTA TCA GAT GAA
Asp Gln Val Ser Asn Leu Val Asp Cys Leu Ser Asp Glu 2237        2246        2255        2264
TTT TGT CTG GAT GAA AAG CGA GAA TTG TCC GAG AAA GTC
Phe Cys Leu Asp Glu Lys Arg Glu Leu Ser Glu Lys Val 2273        2282        2291        2300        2309
AAA CAT GCG AAG CGA CTC AGT GAT GAG CGG AAT TTA CTT
Lys His Ala Lys Arg Leu Ser Asp Glu Arg Asn Leu Leu 2318        2327        2336        2345
CAA GAT CCA AAC TTC AGA GGG ATC AAT AGA CAA CCA GAC
Gln Asp Pro Asn Phe Arg Gly Ile Asn Arg Gln Pro Asp 2354        2363        2372        2381
CGT GGC TGG AGA GGA AGT ACA GAT ATT ACC ATC CAA GGA
Arg Gly Trp Arg Gly Ser Thr Asp Ile Thr Ile Gln Gly 2390        2399        2408        2417        2426
GGA GAT GAC GTA TTC AAA GAG AAT TAC GTC ACA CTA CCG
Gly Asp Asp Val Phe Lys Glu Asn Tyr Val Thr Leu Pro
```

FIG. 14J

```
     2435          2444          2453          2462
GGT ACC GTT GAT GAG TGC TAT CCA ACG TAT TTA TAT CAG
Gly Thr Val Asp Glu Cys Tyr Pro Thr Tyr Leu Tyr Gln 2471          2480          2489          2498
AAA ATA GAT GAG TCG AAA TTA AAA GCT TAT ACC CGT TAT
Lys Ile Asp Glu Ser Lys Leu Lys Ala Tyr Thr Arg Tyr 2507          2516          2525          2534          2543
GAA TTA AGA GGG TAT ATC GAA GAT AGT CAA GAC TTA GAA
Glu Leu Arg Gly Tyr Ile Glu Asp Ser Gln Asp Leu Glu 2552          2561          2570          2579
     ATC TAT TTG ATC CGT TAC AAT GCA AAA CAC GAA ATA GTA
     Ile Tyr Leu Ile Arg Tyr Asn Ala Lys His Glu Ile Val 2588          2597          2606          2615
AAT GTG CCA GGC ACG GGT TCC TTA TGG CCG CTT TCA GCC
Asn Val Pro Gly Thr Gly Ser Leu Trp Pro Leu Ser Ala 2624          2633          2642          2651          2660
CAA AGT CCA ATC GGA AAG TGT GGA GAA CCG AAT CGA TGC
Gln Ser Pro Ile Gly Lys Cys Gly Glu Pro Asn Arg Cys
```

FIG. 14K

```
       2669           2678           2687           2696
     GCG CCA CAC CTT GAA TGG AAT CCT GAT CTA GAT TGT TCC
     Ala Pro His Leu Glu Trp Asn Pro Asp Leu Asp Cys Ser 2705           2714           2723           2732
     TGC AGA GAC GGG GAA AAA TGT GCA CAT CAT TCC CAT CAT
     Cys Arg Asp Gly Glu Lys Cys Ala His His Ser His His 2741           2750           2759           2768           2777
  TTC ACC TTG GAT ATT GAT GTT GGA TGT ACA GAC TTA AAT
  Phe Thr Leu Asp Ile Asp Val Gly Cys Thr Asp Leu Asn 2786           2795           2804           2813
     GAG GAC TTA GGT GTA TGG GTG ATA TTC AAG ATT AAG ACG
     Glu Asp Leu Gly Val Trp Val Ile Phe Lys Ile Lys Thr 2822           2831           2840           2849
     CAA GAT GGC CAT GCA AGA CTA GGG AAT CTA GAG TTT CTC
     Gln Asp Gly His Ala Arg Leu Gly Asn Leu Glu Phe Leu 2858           2867           2876           2885           2894
  GAA GAG AAA CCA TTA TTA GGG GAA GCA CTA GCT CGT GTG
  Glu Glu Lys Pro Leu Leu Gly Glu Ala Leu Ala Arg Val
```

FIG. 14L

```
         2903        2912        2921        2930
       AAA AGA GCG GAG AAG AAG TGG AGA GAC AAA CGA GAG AAA
       Lys Arg Ala Glu Lys Lys Trp Arg Asp Lys Arg Glu Lys 2939        2948        2957        2966
       CTG CAG TTG GAA ACA AAT ATT GTT TAT AAA GAG GCA AAA
       Leu Gln Leu Glu Thr Asn Ile Val Tyr Lys Glu Ala Lys 2975        2984        2993        3002        3011
   GAA TCT GTA GAT GCT TTA TTT GTA AAC TCT CAA TAT GAT
   Glu Ser Val Asp Ala Leu Phe Val Asn Ser Gln Tyr Asp 3020        3029        3038        3047
       AGA TTA CAA GTG GAT ACG AAC ATC GCG ATG ATT CAT GCG
       Arg Leu Gln Val Asp Thr Asn Ile Ala MET Ile His Ala 3056        3065        3074        3083
       GCA GAT AAA CGC GTT CAT AGA ATC CGG GAA GCG TAT CTG
       Ala Asp Lys Arg Val His Arg Ile Arg Glu Ala Tyr Leu 3092        3101        3110        3119        3128
   CCA GAG TTG TCT GTG ATT CCA GGT GTC AAT GCG GCC ATT
   Pro Glu Leu Ser Val Ile Pro Gly Val Asn Ala Ala Ile
```

FIG. 14M

```
      3137           3146           3155           3164
  TTC GAA GAA TTA GAG GGA CGT ATT TTT ACA GCG TAT TCC
  Phe Glu Glu Leu Glu Gly Arg Ile Phe Thr Ala Tyr Ser 3173           3182           3191           3200
  TTA TAT GAT GCG AGA AAT GTC ATT AAA AAT GGC GAT TTC
  Leu Tyr Asp Ala Arg Asn Val Ile Lys Asn Gly Asp Phe 3209           3218           3227           3236           3245
  AAT AAT GGC TTA TTA TGC TGG AAC GTG AAA GGT CAT GTA
  Asn Asn Gly Leu Leu Cys Trp Asn Val Lys Gly His Val 3254           3263           3272           3281
  GAT GTA GAA GAG CAA AAC AAC CAC CGT TCG GTC CTT GTT
  Asp Val Glu Glu Gln Asn Asn His Arg Ser Val Leu Val 3290           3299           3308           3317
  ATC CCA GAA TGG GAG GCA GAA GTG TCA CAA GAG GTT CGT
  Ile Pro Glu Trp Glu Ala Glu Val Ser Gln Glu Val Arg 3326           3335           3344           3353           3362
  GTC TGT CCA GGT CGT GGC TAT ATC CTT CGT GTC ACA GCA
  Val Cys Pro Gly Arg Gly Tyr Ile Leu Arg Val Thr Ala
```

FIG. 14N

```
      3371        3380        3389        3398
TAT AAA GAG GGA TAT GGA GAG GGC TGC GTA ACG ATC CAT
Tyr Lys Glu Gly Tyr Gly Glu Gly Cys Val Thr Ile His 3407        3416        3425        3434
GAG ATC GAA GAC AAT ACA GAC GAA CTG AAA TTC AGC AAC
Glu Ile Glu Asp Asn Thr Asp Glu Leu Lys Phe Ser Asn 3443        3452        3461        3470        3479
TGT GTA GAA GAG GAA GTA TAT CCA AAC AAC ACA GTA ACG
Cys Val Glu Glu Glu Val Tyr Pro Asn Asn Thr Val Thr 3488        3497        3506        3515
TGT AAT AAT TAT ACT GGG ACT CAA GAA GAA TAT GAG GGT
Cys Asn Asn Tyr Thr Gly Thr Gln Glu Glu Tyr Glu Gly 3524        3533        3542        3551
ACG TAC ACT TCT CGT AAT CAA GGA TAT GAC GAA GCC TAT
Thr Tyr Thr Ser Arg Asn Gln Gly Tyr Asp Glu Ala Tyr 3560        3569        3578        3587        3596
GGT AAT AAC CCT TCC GTA CCA GCT GAT TAC GCT TCA GTC
Gly Asn Asn Pro Ser Val Pro Ala Asp Tyr Ala Ser Val
```

FIG. 14O

```
      3605        3614        3623        3632
TAT GAA GAA AAA TCG TAT ACA GAT GGA CGA AGA GAG AAT
Tyr Glu Glu Lys Ser Tyr Thr Asp Gly Arg Arg Glu Asn 3641        3650        3659        3668
CCT TGT GAA TCT AAC AGA GGC TAT GGG GAT TAC ACA CCA
Pro Cys Glu Ser Asn Arg Gly Tyr Gly Asp Tyr Thr Pro 3677       3686        3695        3704        3713
CTA CCG GCT GGT TAT GTA ACA AAG GAT TTA GAG TAC TTC
Leu Pro Ala Gly Tyr Val Thr Lys Asp Leu Glu Tyr Phe 3722        3731        3740        3749
    CCA GAG ACC GAT AAG GTA TGG ATT GAG ATC GGA GAA ACA
    Pro Glu Thr Asp Lys Val Trp Ile Glu Ile Gly Glu Thr 3758        3767        3776        3785
    GAA GGA ACA TTC ATC GTG GAT AGC GTG GAA TTA CTC CTT
    Glu Gly Thr Phe Ile Val Asp Ser Val Glu Leu Leu Leu 3794        3803        3813        3823        3833
ATG GAG GAA TAA GATACGTTAT AAAATGTAAC GTATGCAAAT
MET Glu Glu
```

FIG. 14P

```
      3843       3853       3863       3873       3883
AAAGAATGAT TACTGACCTA TATTAACAGA TAAATAAGAA AATTTTTATA 3893       3903       3913       3923
CGAATAAAAA ACGGACATCA CTCTTAAGAG AATGATGTCC
```

FIG. 14Q

RECOMBINANT PLANT EXPRESSING NON-COMPETITIVELY BINDING BT INSECTICIDAL CRYSTAL PROTEINS

This application is a divisional of application Ser. No. 08/173,274, filed Dec. 23, 1993, now abandoned which is a continuation of application Ser. No. 07/640,400, filed on Jan. 22, 1991, now abandoned, which is a 371 of PCT/EP90/00905, filed May 30, 1990.

This invention relates to plant cells and plants, the genomes of which are transformed to contain at least two genes, each coding for a different non-competitively binding *Bacillus thuringiensis* ("*B. thuringiensis*" or "Bt") insecticidal crystal protein ("ICP") for a specific target insect species, preferably belonging to the order of Lepidoptera or Coleoptera. Such transformed plants have advantages over plants transformed with a single *B. thuringiensis* ICP gene, especially with respect to the prevention of resistance development in the target insect species against the at least two *B. thuringiensis* ICPs, expressed in such plants.

This invention also relates to a process for the production of such transgenic plants, taking into account the competitive and non-competitive binding properties of the at least two *B. thuringiensis* ICPs in the target insect species' midgut. Simultaneous expression in plants of the at least two genes, each coding for a different non-competitively binding *B. thuringiensis* ICP in plants, is particularly useful to prevent or delay resistance development of insects against the at least two *B. thuringiensis* ICPs expressed in the plants.

This invention further relates to a process for the construction of novel plant expression vectors and to the novel plant expression vectors themselves, which contain the at least two *B. thuringiensis* ICP genes encoding the at least two non-competitively binding *B. thuringiensis* ICPs. Such vectors allow integration and coordinate expression of the at least two *B. thuringiensis* ICP genes in plants.

BACKGROUND OF THE INVENTION

Since the development and the widespread use of chemical insecticides, the occurrence of resistant insect strains has been an important problem. Development of insecticide resistance is a phenomenon dependent on biochemical, physiological, genetic and ecological mechanisms. Currently, insect resistance has been reported against all major classes of chemical insecticides including chlorinated hydrocarbons, organophosphates, carbamates, and pyrethroid compounds (Brattsten et al., 1986).

In contrast to the rapid development of insect resistance to synthetic insecticides, development of insect resistance to bacterial insecticides such as *B. thuringiensis* sprays has evolved slowly despite many years of use (Brattsten et al., 1986). The spore forming gram-positive bacterium *B. thuringiensis* produces a parasporal crystal which is composed of crystal proteins (ICPs) having insecticidal activity. Important factors decreasing the probability of emergence of resistant insect strains in the field against *B. thuringiensis* sprays are: firstly the short half-life of *B. thuringiensis* sprays after foliar application; secondly the fact that commercial *B. thuringiensis* preparations often consist of a mixture of several insecticidal factors including spores, ICPs and eventually beta-exotoxins (Shields, 1987); and thirdly the transitory nature of plant-pest interactions. Many successful field trials have shown that commercial preparations of a *B. thuringiensis* containing its spore-crystal complex, effectively control lepidopterous pests in agriculture and forestry (Krieg and Langenbruch, 1981). *B. thuringiensis* is at present the most widely used pathogen for microbial control of insect pests.

Various laboratory studies, in which selection against *B. thuringiensis* was applied over several generations of insects, have confirmed that resistance against *B. thuringiensis* is seldom obtained. However, it should be emphasized that the laboratory conditions represented rather low selection pressure conditions.

For example, Goldman et al. (1986) have applied selection with *B. thuringiensis israelensis* toxin over 14 generations of *Aedes aegypti* and found only a marginal decrease in sensitivity. The lack of any observable trend toward decreasing susceptibility in the selected strains may be a reflection of the low selection pressure ($LC_{50}$) carried out over a limited number of generations. However, it should be pointed out that Georghiou et al. (In: Insecticide Resistance in Mosquitoes: Research on new chemicals and techniques for management. In "Mosquito Control Research, Annual Report 1983, University of California.") with *Culex quinquefasciatus* obtained an 11-fold increase in resistance to *B. thuringiensis israelensis* after 32 generations at $LC_{95}$ selection presssure.

McGaughey (1985) reported that the grain storage pest *Plodia interpunctella* developed resistance to the spore-crystal complex of *B. thuringiensis*; after 15 generations of selection with the Indian meal moth, *Plodia interpunctella*, using a commercial *B. thuringiensis* HD-1 preparation ("Dipel", Abbott Laboratories, North Chicago, Ill. 60064, U.S.A.), a 100-fold decrease in *B. thuringiensis* sensitivity was reported. Each of the colonies was cultured for several generations on a diet treated with a constant *B. thuringiensis* dosage which was expected to produce 70–90% larval mortality. Under these high selection presssure conditions, insect resistance to *B. thuringiensis* increased rapidly. More recently, development of resistance against *B. thuringiensis* is also reported for the almond moth, *Cadra cautella* (McGaughey and Beeman, 1988). Resistance was stable when selection was discontinued and was inherited as a recessive trait (McGaughey and Beeman, 1988). The mechanism of insect resistance to *B. thuringiensis* toxins of *Plodia interpunctella* and *Cadra cautella* has not been elucidated.

The main cause of *B. thuringiensis* resistance development in both reported cases involving grain storage was the environmental conditions prevailing during the grain storage. Under the conditions in both cases, the environment was relatively stable, so *B. thuringiensis* degradation was slow and permitted successive generations of the pest to breed in the continuous presence of the microbial insecticide. The speed at which Plodia developed resistance to *B. thuringiensis* in one study suggests that it could do so within one single storage season in the bins of treated grain.

Although insect resistance development against *B. thuringiensis* has mostly been observed in laboratory and pilot scale studies, very recent indications of *B. thuringiensis* resistance development in *Plutella xylostella* populations in the (cabbage) field have been reported (Kirsch and Schmutterer, 1988). A number of factors have led to a continuous exposure of *P. xylostella* to *B. thuringiensis* in a relatively small geographic area. This and the short generation cycle of *P. xylostella* have seemingly led to an enormous selection pressure resulting in decreased susceptibility and increased resistance to *B. thuringiensis*.

A procedure for expressing a *B. thuringiensis* ICP gene in plants in order to render the plants insect-resistant (European patent publication ("EP") 0193259 [which is incorporated herein by reference]; Vaeck et al., 1987; Barton et al., 1987; Fischhoff et al., 1987) provides an entirely new approach to insect control in agriculture which is at the same time safe, environmentally attractive and cost-effective. An important determinant for the success of this approach will be whether insects will be able to develop resistance to *B. thuringiensis* ICPs expressed in transgenic plants (Vaeck et al., 1987; Barton et al., 1987; Fischhoff et al., 1987). In contrast with a foliar application, after which *B. thuringiensis* ICPs are rapidly degraded, the transgenic plants will exert a continuous selection pressure. It is clear from laboratory selection experiments that a continuous selection pressure has led to adaptation to *B. thuringiensis* and its components in several insect species. In this regard, it should be pointed out that the conditions in the laboratory which resulted in the development of insect-resistance to *B. thuringiensis* are very similar to the situation with transgenic plants which produce *B. thuringiensis* ICPs and provide a continuous selection pressure on insect populations feeding on the plants. Mathematical models of selection pressure predict that, if engineered insect-resistant plants become a permanent part of their environment, resistance development in insects will emerge rapidly (Gould, 1988). Thus, the chances for the development of insect resistance to *B. thuringiensis* in transgenic plants may be considerably increased as compared to the field application of *B. thuringiensis* sprays. A *Heliothis virescens* strain has been reported that is 20 times more resistant to *B. thuringiensis* HD-1 ICP produced by transgenic *Pseudomonas fluorescens* and 6 times more resistant to the pure ICP (Stone et al., 1989). Furthermore, the monetary and human costs of resistance are difficult to assess, but loss of pesticide effectiveness invariably entails increased application frequencies and dosages and, finally, more expensive replacement compounds as new pesticides become more difficult to discover and develop.

Therefore, it would be desirable to develop means for delaying or even preventing the evolution of resistance to *B. thuringiensis*.

*B. thuringiensis* strains, active against Lepidoptera (Dulmage et al., 1981), Diptera (Goldberg and Margalit, 1977) and Coleoptera (Krieg et al., 1983), have been described. It has become clear that there is a substantial heterogeneity among ICPs from different strains active against Lepidoptera, as well as among ICPs from strains active against Coleoptera (Hofte and Whiteley, 1989). An overview of the different *B. thuringiensis* ICP genes, that have been characterized, is given in Table 2 (which follows the Examples herein).

Most of the anti-Lepidopteran *B. thuringiensis* (e.g., Bt3, Bt2, Bt73, Bt14, Bt15, Bt4, Bt18) ICP genes encode 130 to 140 kDa protoxins which dissolve in the alkaline environment of an insect's midgut and are proteolytically activated into an active toxin of 60–65 kDa. These ICPs are related and can be recognized as members of the same family based on sequence homologies. The sequence divergence however is substantial, and the insecticidal spectrum, among the order Lepidoptera, may be substantially different (Höfte et al., 1988).

The P2 toxin gene and the cry B2 gene are different from the above-mentioned genes in that they do not encode high molecular weight protoxins but rather toxins of around 70 kDa (Donovan et al., 1988 and Widner and Whiteley, 1989, respectively).

It has recently become clear that heterogeneity exists also in the anti-Coleopteran toxin gene family. Whereas several previously reported toxin gene sequences from different *B. thuringiensis* isolates with anti-Coleopteran activity were identical (EP 0149162 and 0202739), the sequences and structure of bt21 and bt22 are substantially divergent (European patent application ("EPA") 89400428.2).

While the insecticidal spectra of *B. thuringiensis* ICPs are different, the major pathway of their toxic action is believed to be common. All *B. thuringiensis* ICPs, for which the mechanism of action has been studied in any detail, interact with the midgut epithelium of sensitive species and cause lysis of the epithelial cells (Knowles and Ellar, 1986) due to the fact that the permeability characteristics of the brush border membrane and the osmotic balance over this membrane are perturbed. In the pathway of toxic action of *B. thuringiensis* ICPs, the binding of the toxin to receptor sites on the brush border membrane of these cells is an important feature (Hofmann et al., 1988b). The toxin binding sites in the midgut can be regarded as an ICP-receptor since toxin is bound in a saturable way and with high affinity (Hofmann et al., 1988a).

Although this outline of the mode of action of *B. thuringiensis* ICPs is generally accepted, it remains a matter of discussion what the essential determinant(s) are for the differences in their insecticidal spectra. Haider et al. (1986) emphasize the importance of specific proteases in the insect midgut. Hofmann et al. (1988b) indicate that receptor binding is a prerequisite for toxic activity and describe that *Pieris brassicae* has two distinct receptor populations for two toxins. Other authors have suggested that differences in the environment of the midgut (e.g., pH of the midgut) might be crucial.

SUMMARY OF THE INVENTION

In accordance with this invention, a plant is provided having, stably integrated into its genome, at least two *B. thuringiensis* ICP genes encoding at least two non-competitively binding insecticidal *B. thuringiensis* ICPs, preferably the active toxins thereof, against a specific target insect, preferably against a Lepidoptera or Coleoptera. Such a plant is characterized by the simultaneous expression of the at least two non-competitively binding *B. thuringiensis* ICPs.

Also in accordance with this invention, at least two ICP genes, particularly two genes or parts thereof coding for two non-competitively binding anti-Lepidopteran or anti-Coleopteran *B. thuringiensis* ICPs, are cloned into a plant expression vector. Plant cells transformed with this vector are characterized by the simultaneous expression of the at least two *B. thuringiensis* ICP genes. The resulting transformed plant cell can be used to produce a transformed plant in which the plant cells: 1. contain the at least two *B. thuringiensis* ICP genes or parts thereof encoding at least two non-competitively binding anti-Lepidopteran or anti-Coleopteran *B. thuringiensis* ICPs as a stable insert into their genome; and 2. express the genes simultaneously, thereby conferring on the plant improved resistance to at least one target species of insect, so as to prevent or delay development of resistance to *B. thuringiensis* of the at least one target species of insect feeding on the transformed plant.

Further in accordance with this invention, plant expression vectors are provided which allow integration and simultaneous expression of at least two *B. thuringiensis* ICP genes in a plant cell and which comprise one or more chimeric genes, each containing in the same transcriptional unit: a promoter which functions in the plant cell to direct the synthesis of mRNA encoded by one of the ICP genes; one or more different ICP genes, each encoding a non-competitively binding *B. thuringiensis* ICP; preferably a marker gene; a 3' non-translated DNA sequence which functions in the plant cell for 3' end formation and the addition of polyadenylate nucleotides to the 3' end of the mRNA; and optionally a DNA sequence encoding a protease-sensitive protein part between any two ICP genes.

BRIEF DESCRIPTION OF THE DRAWINGS

FIGS. 13A–13Q depict the nucleotide sequence and deduced amino acid sequence of the open reading frame of the bt4 gene extending from nucleotide 264 to nucleotide 3761.

FIGS. 14A–14Q depict the nucleotide sequence and deduced amino acid sequence of the open reading frame of the bt15 gene extending from nucleotide 234 to nucleotide 3803.

DETAILED DESCRIPTION OF THE INVENTION

Definitions

Figure 1:
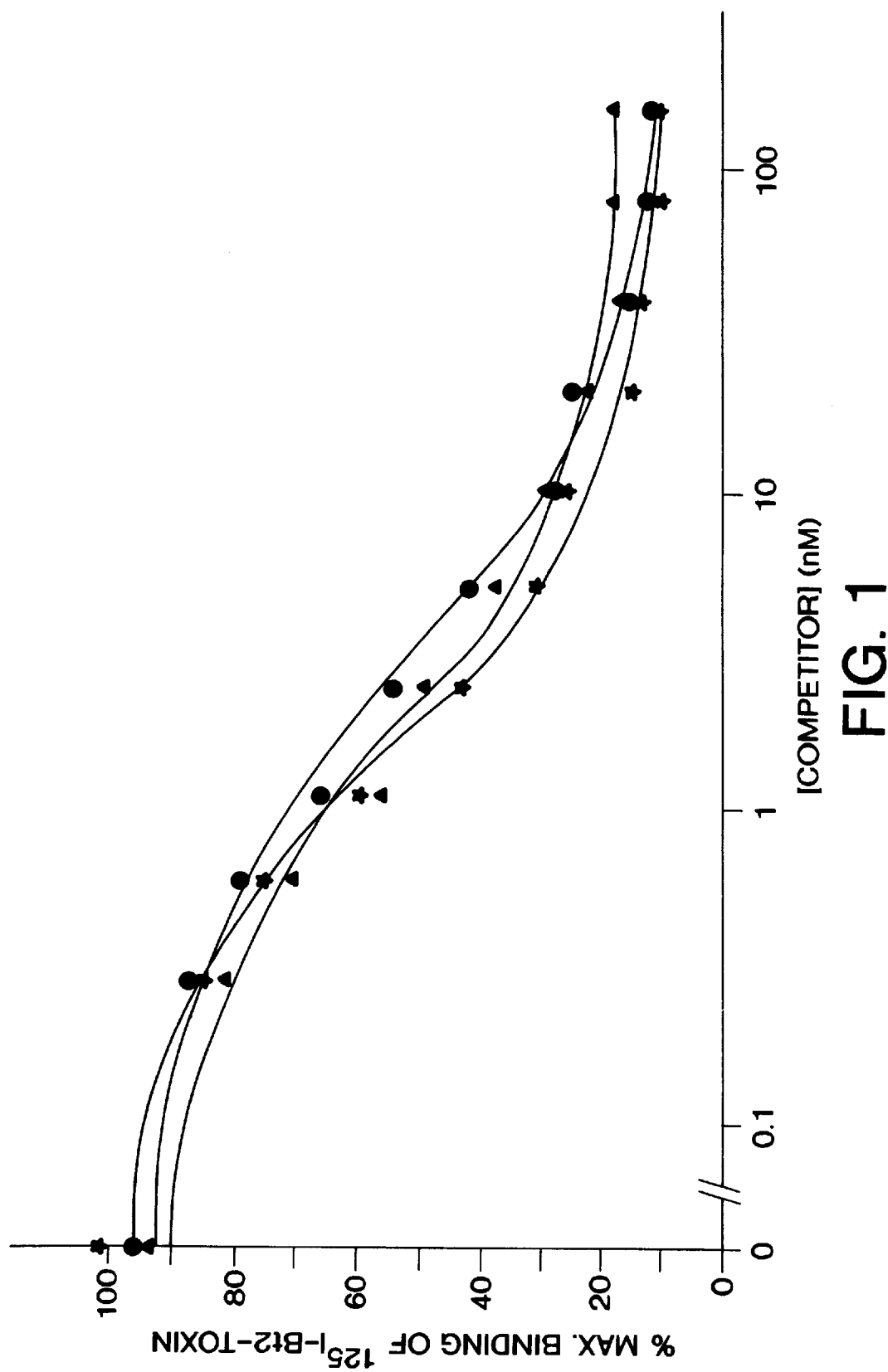
FIG. 1 is a graph showing the binding of $^{125}$I-labeled Bt2 toxin to *M. sexta* BBMV in the presence of increasing concentrations of Bt2 toxin (★), Bt3 toxin (●) or Bt73 toxin (▲).

As used herein, "*B. thuringiensis* ICP" (or "ICP") should be understood as an intact protein or a part thereof which has insecticidal activity and which can be produced in nature by *B. thuringiensis*. An ICP can be a protoxin, as well as an active toxin or another insecticidal truncated part of a protoxin which need not be crystalline and which need not be a naturally occurring protein. In this regard, an ICP can be a chimaeric toxin encoded by the combination of two variable regions of two different ICP genes as disclosed in EP 0228838.

As used herein, "protoxin" should be understood as the primary translation product of a full-length gene encoding an ICP.

As used herein, "toxin", "toxic core" or "active toxin" should all be understood as a part of a protoxin which can be obtained by protease (e.g., by trypsin) cleavage and has insecticidal activity.

As used herein, "gene" should be understood as a full-length DNA sequence encoding a protein (e.g., such as is found in nature), as well as a truncated fragment thereof encoding at least the active part (i.e., toxin) of the protein encoded by the full-length DNA sequence, preferably encoding just the active part of the protein encoded by the full-length DNA sequence. A gene can be naturally occurring or synthetic.

As used herein, "truncated *B. thuringiensis* gene" should be understood as a fragment of a full-length *B. thuringiensis* gene which still encodes at least the toxic part of the *B. thuringiensis* ICP, preferentially the toxin.

As used herein, "marker gene" should be understood as a gene encoding a selectable marker (e.g., encoding antibiotic resistance) or a screenable marker (e.g., encoding a gene product which allows the quantitative analysis of transgenic plants).

Two ICPs are said to be "competitively binding ICPs" for a target insect species when one ICP competes for all ICP receptors of the other ICP, which receptors are present in the brush border membrane of the midgut of the target insect species.

Two ICPs are said to be "non-competitively binding ICPs" when, for at least one target insect species, the first ICP has at least one receptor for which the second ICP does not compete and the second ICP has at least one receptor for which the first ICP does not compete, which receptors are present in the brush border membrane of the midgut of the target insect species.

A "receptor" should be understood as a molecule, to which a ligand (here a *B. thuringiensis* ICP, preferably a toxin) can bind with high affinity (typically a dissociation constant (Kd) between $10^{-11}$ and $10^{-6}$M) and saturability. A determinaetion of whether two ICPs are competitively or non-competitively binding ICPs can be made by determining whether: 1. a first ICP competes for all of the receptors of a second ICP when all the binding sites of the second ICP with an affinity in the range of about $10^{-11}$ to $10^{-6}$M can be saturated with the first ICP in concentrations of the first ICP of about $10^{-5}$M or less (e.g., down to about $10^{-11}$M); and 2. the second ICP competes for the all of the receptors of the first ICP when all the binding sites of the first ICP with an affinity in the range of about $10^{-11}$ to $10^{-6}$M can be saturated with the second ICP in concentrations of the second ICP of about $10^{-5}$M or less.

General Procedures

This section describes in broad terms general procedures for the evaluation and exploitation of at least two *B. thuringiensis* ICP genes for prevention of the development, in a target insect, of a resistance to the *B. thuringiensis* ICPs expressed in transgenic plants of this invention. A non-exhaustive list of consecutive steps in the general procedure follows, after which are described particular Examples that are based on this methodology and that illustrate this invention.

In accordance with this invention, specific *B. thuringiensis* ICPs can be isolated in a conventional manner from the respective strains such as are listed in Table 2 (which follows the Examples). The ICPs can be used to prepare monoclonal or polyclonal antibodies specific for these ICPs in a conventional manner (Höfte et al., 1988).

The ICP genes can each be isolated from their respective strains in a conventional manner. Preferably, the ICP genes are each identified by: digesting total DNA from their respective strains with suitable restriction enzyme(s); size fractionating the DNA fragments, so produced, into DNA fractions of 5 to 10 Kb; ligating such fractions to suitable cloning vectors (e.g., pEcoR251, deposited at the Deutsche Sammlung von Mikroorganismen und Zellculturen ("DSM"), Braunschweig, Federal Republic of Germany, under accession number no. 4711 on Jul. 13, 1988); transforming *E. coli* with the cloning vectors; and screening the clones with a suitable DNA probe. The DNA probe can be constructed from a highly conserved region which is commonly present in different *B. thuringiensis* genes which encode crystal protoxins against Coleoptera or Lepidoptera, such as on the basis of an N-terminal amino acid sequence determined by gas-phase sequencing of the purified proteins (EPA 88402115.5).

Alternatively, the desired fragments, prepared from total DNA of the respective strains, can be ligated in suitable expression vectors ( e.g., a pUC vector (Yanisch-Perron et al., 1985) with the insert under the control of the lac promoter) and transformed in *E. coli*, and the clones can then be screened by conventional colony immunoprobing methods (French et al., 1986) for expression of the toxins with monoclonal or polyclonal antibodies raised against the toxins produced by the strains.

The isolated *B. thuringiensis* ICP genes can then be sequenced in a conventional manner using well-known procedures (e.g., Maxam and Gilbert, 1980).

At present, several ICP genes have been cloned from different subspecies of *B. thuringiensis* (Table 2). The nucleotide sequences from several of these *B. thuringiensis* ICP genes have been reported. Whereas several sequences are identical or nearly identical and represent the same gene or slight variants of the same gene, several sequences display substantial heterogeneity and show the existence of different *B. thuringiensis* ICP gene classes. Several lines of evidence suggest that all these genes specify a family of related insecticidal proteins. Analysis of the distribution of *B. thuringiensis* ICPs in different *B. thuringiensis* strains by determining the protein composition of their crystals, by immunodetection using polyclonal antisera or monoclonals against purified crystals, or by using gene-specific probes, shows that subspecies of *B. thuringiensis* might contain up to three related *B. thuringiensis* ICP genes belonging to different classes (Kronstad et al., 1983).

To express the isolated and characterized gene in a heterologous host for purification and characterization of the recombinant protein, the preferred organism is *Escherichia coli*. A number of expression vectors for enhanced expression of heterologous genes in *E. coli* have been described (e.g., Remaut et al., 1981). Usually the gene is cloned under control of a strong regulatable promoter, such as the lambda pL or pR promoters (e.g., Botterman and Zabeau, 1987), the lac promoter (e.g., Fuller, 1982) or the tac promoter (e.g., De Boer et al., 1983), and provided with suitable translation initiation sites (e.g., Stanssens et al, 1985 and 1987). Gene cassettes of the *B. thuringiensis* ICP genes can be generated by site-directed mutagenesis, for example-according to the procedure described by Stanssens et al. (1985 and 1987). This allows cassettes to be made comprising, for example, a truncated ICP gene fragment encoding the toxic core (i.e., toxin) of an ICP or a hybrid gene encoding the toxic core and a selectable marker according to the procedures described in EPA 88402241.9.

The cells of an *E. coli* culture, which has been induced to produce a recombinant ICP, are harvested. The method used to induce the cells to produce the recombinant ICP depends on the choice of the promoter. For example, the lac promoter (Fuller, 1982) is induced by isopropyl-B-D-thiogalacto-pyranoside ("IPTG"); the pL promoter is induced by temperature shock (Bernard et al., 1979). The recombinant ICP is usually deposited in the cells as insoluble inclusions (Hsuing and Becker, 1988). The cells are lysed to liberate the inclusions. The bulk of *E. coli* proteins is removed in subsequent washing steps. A semi-purified protoxin pellet is obtained, from which the protoxin can be dissolved in alkaline buffer (e.g., $Na_2CO_3$, pH 10). The procedure for the ICP Bt2, which is also applicable to other recombinant toxins, has been described by Höfte et al., 1986.

In accordance with this invention, the binding of various ICPs to ICP receptors on the brush border membrane of the columnar midgut epithelial cells of various insect species has been investigated. The brush border membrane is the primary target of each ICP, and membrane vesicles, preferentially derived from the brush border membrane, can be obtained according to Wolfersberger et al., 1987.

The binding to ICP receptors of one or more ICPs (e.g., ICP A, ICP B, etc.) can be characterized by the following steps (Hofmann et al, 1988b):

1. ICP A is labelled with a suitable marker (usually a radioisotope such as $^{125}I$).
2. Brush border membranes are incubated with a small amount (preferably less than $10^{31\ 10}M$) of labelled ICP A together with different concentrations of non-labelled ICP A (preferably from less than $10^{-11}$ to $10^{-5}M$).
3. For all concentrations tested the amount of labelled ICP A bound to the brush border membranes is measured.
4. Mathematical analysis of these data allows one to calculate various characteristics of the ICP receptor such as the magnitude of the population of binding sites (Scatchard, 1949).
5. Competition by other toxins (e.g. ICP B) is preferably studied by incubating the same amount of labelled ICP A with brush border membranes in combination with different amounts of ICP B (preferentially from $10^{-11}$ to $10^{-6}M$; and subsequently, steps 3 and 4 are repeated.

By this procedure, it has been found, for example, that Bt3 toxin, Bt2 toxin and Bt73 toxin are competitively binding anti-Lepidopteran ICPs for *Manduca sexta* and *Heliothis virescens* (See example 6 which follows). Various other combinations of toxins have been found to be non-competitively binding anti-Lepidopteran or anti-Coleopteran toxins (example 6).

Although the concept of competitivity versus non-competitivity of ICP binding does not have any practical importance by itself, the observation of the non-competitivity of two *B. thuringiensis* ICPs, active against the same target insect, can be put to very significant practical use. This is because a combination of two non-competitively binding *B. thuringiensis* ICPs can be used to prevent development, by a target insect, of resistance against such *B. thuringienis* ICPs.

A selection experiment with *M. sexta*, using Bt2 toxin, Bt18 toxin, and a mixture of Bt2 and Bt18 toxins, has shown that Bt2 and Bt18 are two non-competitively binding anti-Lepidopteran toxins. After 20 generations of selection, a very pronounced reduction in ICP sensitivity was observed in the selection experiments with Bt2 or Bt18 alone (>100 times). The reduction in sensitivity in the selection experiment with a Bt2–Bt18 mixture was only marginal (3 times). This demonstrates the unexpected practical advantage of a simultaneous use of two non-competitively binding ICPs in a situation which models the high selection pressure which will exist with the use of transgenic plants transformed with ICP genes. In this regard, the two resistant strains showed a specific loss in receptor sites for either the Bt2 or Bt18 toxin. In each case, receptor sites for the toxin, which was not used for selection, were not affected or their concentration even increased. Thus, the Bt2 selected strain retained its Bt18 receptors, and the Bt18 selected strain developed an increased number of Bt2 receptors. Indeed, the Bt18 selected strain showed an increased sensitivity for Bt2 along with its increased Bt2 receptor concentration. No significant changes in receptor sites were found in the strain selected against the combined toxins. These findings are described in detail in Example 7 which follows.

A similar mechanism of resistance to Bt has been observed with respect to a strain of diamondback moth, *Plutella xylostella*. This strain had developed resistance in the field to Dipel which is a commercial formulation of the Bt HD-1 strain. Crystals of Dipel comprise a mixture of several BtICPs, similar to the Bt2, Bt3 and Bt73 proteins which are competitively-binding ICPs. As shown by both insect bioassays and competitive binding studies using Bt2 and Bt15, the Dipel-resistant diamondback moth strain is resistant to Bt2 protoxin and toxin but maintains full sensitivity to Bt15 protoxin and toxin. This finding is relevant to other combinations of non-competitively binding anti-Lepidopteran or Coleopteran ICPs which are expected to have the same beneficial effect against their common target insects.

Hence, a combination of non-competitively binding ICPs, when directly expressed in a transgenic plant, offers the substantial advantage of reducing the chances of development of insect resistance against the ICPs expressed in the plant. There may be additional benefits because the combined spectrum of two toxins may be broader than the spectrum of a single ICP expressed in a plant (See Examples 8, 9 and 10 which follow).

If, among two competitively binding ICPs, one has a larger binding site population than the other against a given target insect, it will be most advantageous to use the one with the larger population of binding sites to control the target pest in combination with the most suitable non-competitively binding *B. thuringiensis* ICP. For example, as seen from Example 6, it is preferred to use Bt73 against *Heliothis virescens*, rather than Bt2 or Bt3, and it is preferred to use Bt3 against *Manduca sexta* rather than Bt2 or Bt73. The selected gene can then be combined with the best suitable non-competitively binding ICP.

Previously, plant transformations involved the introduction of a marker gene together with a single ICP gene, within the same plasmid, in the plant genome (e.g., Vaeck et al., 1987; Fischoff et al., 1987). Such chimeric ICP genes usually comprised either all or part of an ICP gene, preferably a truncated ICP gene fragment encoding the toxic core, fused to a selectable marker gene, such as the neo gene coding for neomycin phosphotransferase. The chimeric ICP gene was placed between the T-DNA border repeats for Agrobacterium Ti-plasmid mediated transformation (EP 0193259).

This invention involves the combined expression of two or even more *B. thuringiensis* ICP genes in transgenic plants. The insecticidally effective *B. thuringiensis* ICP genes, encoding two non-competitively binding ICPs for a target insect species, preferably encoding the respective truncated ICP genes, are inserted in a plant cell genome, preferably in its nuclear genome, so that the inserted genes are downstream of, and under the control of, a promoter which can direct the expression of the genes in the plant cell. This is preferably accomplished by inserting, in the plant cell genome, one or more chimaeric genes, each containing in the same transcriptional unit: at least one ICP gene; preferably a marker gene; and optionally a DNA sequence encoding a protease (e.g., trypsin)-sensitive or -cleavable protein part intercalated in frame between any two ICP genes in the chimaeric gene. Each chimaeric gene also contains at least one promoter which can direct expression of its ICP gene in the plant cell.

The selection of suitable promoters for the chimaeric genes of this invention is not critical. Preferred promoters for such chimaeric genes include: the strong constitutive 35S promoter obtained from the cauliflower mosaic virus, isolates CM 1841 (Gardner et al., 1981), CabbB-S (Franck et al., 1980) and CabbB-JI (Hull and Howell, 1987); the promoter of the nopaline synthetase gene ("PNOS") of the Ti-plasmid (Herrera-Estrella, 1983); the promoter of the octopine synthase gene ("POCS" [De Greve et al., 1982]); and the wound-inducible TR1' promoter and the TR2' promoter which drive the expression of the 1' and 2' genes, respectively, of the T-DNA (Velten et al., 1984). Alternatively, a promoter can be utilized which is specific for one or more tissues or organs of the plant, whereby the inserted genes are expressed only in cells of the specific tissue(s) or organ(s). Examples of such promoters are a stem-specific promoter such as the AdoMet-synthetase promoter (Peleman et al., 1989), a tuber-specific promoter (Rocha-Sosa et al., 1989), and a seed-specific promoter such as the 2S promoter (Krebbers et al., 1988). The ICP genes could also be selectively expressed in the leaves of a plant (e.g., potato) by placing the genes under the control of a light-inducible promoter such as the promoter of the ribulose-1,5-bisphosphate carboxylase small subunit gene of the plant itself or of another plant such as pea as disclosed in EP 0193259. Another alternative is to use a promoter whose expression is inducible (e.g., by temperature or chemical factors).

A 3' non-translated DNA sequence, which functions in plant cells for 3' end formation and the polyadenylation of the 3' end of the mRNA sequence encoded by the at least one ICP gene in the plant cell, also forms part of each such chimeric gene. The selection of a suitable 3' non-translated DNA sequence is not critical. Examples are the 3' untranslated end of the octopine synthase gene, the nopaline synthase gene or the T-DNA gene 7 (Velten and Schell, 1985).

The selection of marker genes for the chimaeric genes of this invention also is not critical, and any conventional DNA sequence can be used which encodes a protein or polypeptide which renders plant cells, expressing the DNA sequence, readily distinguishable from plant cells not expressing the DNA sequence (EP 0344029). The marker gene can be under the control of its own promoter and have its own 3' non-translated DNA sequence as disclosed above, provided the marker gene is in the same genetic locus as the ICP gene(s) which it identifies. The marker gene can be, for example: a herbicide resistance gene such as the sfr or sfrv genes (EPA 87400141); a gene encoding a modified target enzyme for a herbicide having a lower affinity for the herbicide than the natural (non-modified) target enzyme, such as a modified 5-EPSP as a target for glyphosate (U.S. Pat. No. 4,535,060; EP 0218571) or a modified glutamine synthetase as a target for a glutamine synthetase inhibitor (EP 0240972); or an antibiotic resistance gene, such as a neo gene (PCT publication WO 84/02913; EP 0193259).

Using *A. tumefaciens* Ti vector-mediated plant transformation methodology, all chimeric genes of this invention can be inserted into plant cell genomes after the chimaeric genes have been placed between the T-DNA border repeats of suitable disarmed Ti-plasmid vectors (Deblaere et al., 1988). This transformation can be carried out in a conventional manner, for example as described in EP 0116718, PCT publication WO 84/02913 and EPA 87400544.0. The chimeric genes can also be in non-specific plasmid vectors which can be used for direct gene transfer (e.g., as described by Pazkowski et al., 1984; De La Pena et al., 1986). Different conventional procedures can be followed to obtain a combined expression of two *B. thuringiensis* ICP genes in transgenic plants as summarized below.

I Chimeric gene constructs whereby two or more ICP genes and a marker gene are transferred to the plant genome as a single piece of DNA and lead to the insertion in a single locus in the genome Ia The genes can be engineered in different transcriptional units each under control of a distinct promoter To express two or more ICP genes and a marker gene as separate transcriptional units, several promoter fragments directing expression in plant cells can be used as described above. All combinations of the promoters mentioned above in the chimaeric constructs for one ICP gene are possible. Examples of such individual chimeric constructs are described for the bt2 gene in EP 0193259, for the bt13 gene in EPA 88402115.5 and for the bt18 gene in EPA 88402241.9. The ICP gene in each chimeric gene of this invention can be the intact ICP gene or preferably an insecticidally-effective part of the intact ICP gene, especially a truncated gene fragment encoding the toxic core of the ICP. The individual chimeric genes are cloned in the same plasmid vector according to standard procedures (e.g., EP 0193259).

Ib Two genes (e.g., either an ICP and a marker gene or two ICP genes) or more can be combined in the same transcriptional unit To express two or more ICP genes in the same transcriptional unit, the following cases can be distinguished:

In a first case, hybrid genes in which the coding region of one gene is in frame fused with the coding region of another gene can be placed under the control of a single promoter. Fusions can be made between either an ICP and a marker gene or between two ICP genes. An example of an ICP gene-marker gene fusion has been described in EP 0193259 (i.e., a hybrid truncated bt2-neo gene encoding a Bt2 toxin-NPTII fusion protein).

Another possibility is the fusion of two ICP genes. Between each gene encoding an ICP which still is insecticidally active (i.e., a toxic part of the protoxin), a gene fragment encoding a protease (e.g., trypsin)-sensitive protein part should be included, such as a gene fragment encoding a part of the N-terminal or C-terminal amino acid sequence of one of the ICPs which is removed or cleaved upon activation by the midgut enzymes of the target insect species.

In a second case, the coding regions of the two respective ICP genes can be combined in dicistronic units placed under the control of a promoter. The coding regions of the two ICP genes are placed after each other with an intergenic sequence of defined length. A single messenger RNA molecule is generated, leading to the translation into two separate gene products. Based on a modified scanning model (Kozak, 1987), the concept of reinitiation of translation has been accepted provided that a termination codon in frame with the upstream ATG precedes the downstream ATG. Experimental data also demonstrated that the plant translational machinery is able to synthesize several polypeptides from a polycistronic mRNA (Angenon et al., 1989).

II Chimeric constructs with one or more ICP genes that are transferred to the genome of a plant already transformed with a one or more ICP genes Several genes can be introduced into a plant cell during sequential transformation steps (retransformation), provided that an alternative system to select transformants is available for the second round of transformation. This retransformation leads to the combined expression of ICP genes which are introduced at multiple loci in the genome. Preferably, two different selectable marker genes are used in the two consecutive transformation steps. The first marker is used for selection of transformed cells in the first transformation, while the second marker is used for selection of transformants in the second round of transformation. Sequential transformation steps using kanamycin and hygromycin have been described, for example by Sandler et al. (1988) and Delauney et al. (1988).

III Chimeric constructs with one or more ICP genes, that are separately transferred to the nuclear genome of separate plants in independent transformation events and are subsequently combined in a single plant genome through crosses.

The first plant should be a plant transformed with a first ICP gene or an F1 plant derived herefrom through selfing (preferably an F1 plant which is homozygous for the ICP gene). The second plant should be a plant transformed with a second ICP gene or an F1 plant derived herefrom through selfing (preferably an F1 plant which is homozygous for the second ICP gene). Selection methods can be applied to the plants obtained from this cross in order to select those plants having the two ICP genes present in their genome (e.g., Southern blotting) and expressing the two ICPs (e.g., separate ELISA detection of the immunologically different ICPs). This is a useful strategy to produce hybrid varieties from two parental lines, each transformed with a different ICP gene, as well as to produce inbred lines containing two different ICP genes through crossing of two independent transformants (or their F1 selfed offspring) from the same inbred line.

IV Chimeric constructs with one or more ICP genes separately transferred to the genome of a single plant in the same transformation experiment leading to the insertion of the respective chimeric genes at multiple loci.

Cotransformation involves the simultaneous transformation of a plant with two different expression vectors, one containing a first ICP gene, the second containing a second ICP gene. Along with each ICP gene, a different marker gene can be used, and selection can be made with the two markers simultaneously. Alternatively, a single marker can be used, and a sufficiently large number of selected plants can be screened in order to find those plants having the two ICP genes (e.g., by Southern blotting) and expressing the two proteins (e.g., by means of ELISA). Cotransformation with more than one T-DNA can be accomplished by using simultaneously two different strains of Agrobacterium, each with a different Ti-plasmid (Depicker et al., 1985) or with one strain of Agrobacterium containing two T-DNAs on separate plasmids (de Framond et al., 1986). Direct gene transfer, using a mixture of two plasmids, can also be employed to cotransform plant cells with a selectable and a non-selectable gene (Schocher et al., 1986).

The transgenic plant obtained can be used in further plant breeding schemes. The transformed plant can be selfed to obtain a plant which is homozygous for the inserted genes. If the plant is an inbred line, this homozygous plant can be used to produce seeds directly or as a parental line for a hybrid variety. The gene can also be crossed into open pollinated populations or other inbred lines of the same plant using conventional plant breeding approaches.

Of course other plant transformation methods can be used and are within the scope of the invention as long as they result is a plant which expresses two or more non-competitively binding ICPs. In this regard, this invention is not limited to the use of Agrobacterium Ti-plasmids for transforming plant cells with genes encoding non-competitively binding ICPs. Other known methods for plant cell transformations, such as electroporation or by the use of a vector system based on plant viruses or pollen, can be used for transforming monocotyledonous and dicotyledonous plants in order to obtain plants which express two non-competitively binding ICPs. Furthermore, DNA sequences encoding two non-competitively binding ICPs other than those disclosed herein can be used for transforming plants. Also, each of the ICP genes, described herein, can be encoded by equivalent DNA sequences, taking into consideration the degeneracy of the genetic code. Also, equivalent ICPs with only a few amino acids changed, such as would be obtained through mutations in the ICP gene, can also be used, provided they encode a protein with essentially the same characteristics (e.g., insecticidal activity and receptor binding).

The following Examples illustrate the invention. Those skilled in the art will, however, recognize that other combinations of two or more non-competitively binding *B. thuringiensis* ICP genes can be used to transform plants in accordance with this invention in order to prevent the development, in a target insect, of resistance to *B. thuringiensis* ICPs expressed in the transformed plants. Unless otherwise indicated, all procedures for making and manipulating DNA were carried out by the standardized procedures described in Maniatis et al, *Molecular Cloning—A Laboratory Manual*, Cold Spring Harbor Laboratory (1982).

EXAMPLE 1

Collection of genes

The collection of anti-Lepidopteran and anti-Coleopteran Bt genes encoding ICPs, which are the subject of the Examples, is described in Table 2 (following the Examples). References for the respective genes are indicated in Table 2. The origin, the isolation and characterization of the Bt genes, which have not been published, are described below. Bt strains, such as strains HD-1, HD-68, HD-110, and HD-73, are publicly available from the Agricultural Research Culture Collection, Northern Regional Research Laboratory, U.S. Dept. of Agriculture, Peoria, Ill. 61604, U.S.A.

bt3 gene: From *B. thuringiensis* var. kurstaki HD-1, the ICP was cloned. Characterization of this gene revealed an open reading frame of 3528 bp which encodes a protoxin of 133 kDa. This gene was identical to the one described by Schnepf et al. (1985).

bt73 gene: From *B. thuringiensis* var HD-73. The ICP gene was cloned as described by Adang et al. (1985).

bt4 gene: A genomic library was prepared from total DNA of strain *B. thuringiensis* aizawai HD-68. Using the 1.1 kb internal HindIII fragment of the bt2 gene as a probe, a gene designated bt4 was isolated. Characterization of this gene revealed an open reading frame of 3495 bp which encodes a protoxin of 132 kDa and a trypsin activated toxin fragment of 60 kDa. This (insect controlling protein) gene differs from previously identified genes and was also found in several other strains of subspecies aizawai and entomocidus including HD-110. FIG. 13 shows the nucleotide sequence and deduced amino acid sequence of the open reading frame ("ORF") of the bt4 gene extending from nucleotide 264 to nucleotide 3761.

bt14 and bt15 genes: A genomic library was prepared from total DNA of strain *B. thuringiensis* var. *entomocidus* HD-110 by partial Sau3A digest of the total DNA and cloning in the vector pEcoR251 (deposited at DSM under accession number 4711). Using monoclonal antibodies (Höfte et al., 1988), at least three structurally distinct ICPs were identified in crystals of *B. thuringiensis* entomocidus HD-110. These monoclonal antibodies were used to clone the three different ICP genes from this *B. thuringiensis* strain. One of these genes is the bt4 gene as described above.

The second gene was called "bt15". FIG. 14 shows the nucleotide sequence and deduced amino acid sequence of the ORF of the bt15 gene, isolated from HD-110, extending from nucleotide 234 to nucleotide 3803. The Shine and Dalgarno sequence, preceding the initiation codon is underlined. This gene has an open reading frame of 3567 bp which encodes a protoxin of 135 kDa and a 63 kDa toxin fragment. A similar gene has been described by Honee et al. 1988, isolated from *B. thuringiensis entomocidus* 60.5. The bt15 gene differs from the published sequence at three positions: an Ala codon (GCA) is present instead of an Arg codon (CGA) at position 925 and a consecution of a Thr-His codon (ACGCAT) is present instead of a Thr-Asp codon (ACCGAT) at position 1400. (The numbers of the positions are according to Honnee et al., 1988). Another similar gene has been described in EP 0295156, isolated from *B. thuringiensis aizawai* 7–29 and *entomocidus* 6-01. The bt15 gene is different from this published nucleotide sequence at three different places: 1) a Glu codon (GAA) instead of an Ala codon (GCA) at position 700; 2) the sequence TGG, CCA, GCG, CCA instead of TGC, CAG, CGC, CAC, CAT at position 1456 and 3) an Arg codon (CGT) instead of an Ala codon (GCG) at position 2654. (The numbers of the positions are according to EP 0295156).

The third gene isolated was called "bt14". It has an open reading frame of 3621 bp which encodes a 137 kDa protoxin and a 66 kDa activated toxin fragment. A similar gene has been cloned from *B. thuringiensis* HD-2 (Brizzard and Whiteley, 1988). The bt14 gene differs from the published nucleotide sequence by two nucleotide substitutions: a T instead of a C at position 126, and a C instead of a T at position 448 (the numbers of the positions are according to Brizzard and Whiteley, 1988). In the first case, the Ile codon (ATT or ATC) is conserved whereas in the second case the Tyr codon (TAT) is converted to a His codon (CAC).

bt2 gene: The bt2 gene was cloned as described in EP 0193259.

bt18 gene: Cloning of the bt18 gene was performed as described in EPA 88402241.9.

bt13 gene: The bt13 gene was cloned as described in EPA 88402115.5.

bt21 and bt22 genes: These genes, encoding Coleopteran-active ICPs, were cloned as described in EPA 89400428.2.

EXAMPLE 2

Construction of gene cassettes and expression of Bt genes in *E. coli*

1) bt2, bt18: the construction of bt2 and bt18 gene cassettes has been previously described in EPA 86300291.1 and 88402241.9, respectively. Basically, they comprise a truncated gene encoding the toxic core and a hybrid gene comprising the truncated gene fused in frame to the N-terminus of the neo gene. The gene cassettes are used to transform *E. coli* to express the Bt2 and Bt18 ICP toxins.

2) bt14, bt15: as described in EPA 88402241.9, gene cassettes for the bt14 and bt15 genes were constructed in order to express the genes in *E. coli* and in plants.

First, a NcoI site was introduced at the N-terminus of the genes by site-directed mutagenesis.

In the case of the bt15 gene, the conversion of the TT nucleotides, immediately in front of the ATG codon, into CC yielded a NcoI site overlapping with the ATG initiation codon. This site was introduced using the pMa/c vectors for site-directed mutagenesis (Stanssens et al., 1987) and a 28-mer oligonucleotide with the following sequence:

5'-CGGAGGTATTCCATGGAGGAAAATAATC-3'.

This yielded the plasmid pVE29 carrying the N-terminal fragment of the bt15 gene with a NcoI site at the ATG initiation codon.

According to Brizzard and Whiteley (1988), the initiation codon of the bt14 gene is a TTG codon. Thus, a NcoI site was created in a like manner at this codon for site directed mutagenesis using a 34-mer oligonucleotide with the following sequence

5'-CCTATTTGAAGCCATGGTAACTCCTCCTTTTATG-35'.

In this case the sequence of the intitiation codon was converted from ATATTGA to ACCATGG. This yielded the plasmid pHW44 carrying the N-terminal fragment of the bt14 gene with a NcoI site at the initiation codon.

In a second step, the genes were reconstructed by ligating the N-terminal gene fragments with a suitable C-terminal gene fragment, yielding a bt15 gene and bt14 gene with a NcoI site at the ATG initiation codon.

To express the bt14 and bt15 genes encoding the protoxin in *E. coli*, the following constructs were made: pOH50 containing the bt15 gene under the control of the lac promoter; and pHW67 containing the bt14 gene under the control of the tac promoter. Induction of a culture of the *E. coli* strain WK6 carrying the respective plasmids with IPTG yielded an overproduced protein (Fuller, 1982).

The active toxic fragments of the Bt15 and Bt14 protoxins comprise 63 and 60 kDa trypsin digest products respectively. Instead of expressing the whole bt15 or bt14 gene, it is also possible to express a toxin-encoding gene fragment or derivative thereof in plants. To this end, truncated bt14 and bt15 gene fragments were constructed. In order to be able to select transgenic plants producing the ICP gene products, hybrid genes of the truncated gene fragments were also made with the neo gene encoding a selectable marker as described in EP 0193259.

By comparison of the nucleotide sequence of the bt4, bt14 and bt15 genes, respectively, with the bt2 and bt18 genes, respectively, the BclI site could be identified as a suitable site localized downstream of the coding sequence encoding the toxin gene fragment. To construct a truncated gene fragment and a hybrid gene of the truncated gene fragment with the neo gene, the filled BclI site was ligated to the filled EcoRI site of pLKM91 (Höfte et al., 1986) and the filled HindIII site of pLK94 respectively (Botterman and Zabeau, 1987). pLKM91carries a 5' truncated neo gene fragment which codes for an enzymatically active C-terminal gene fragment of the neo gene, and pLK94 contains translation stop codons in three reading frames. This yielded the following plasmids which are then used to transform *E. coli* to express the ICP genes: pHW71 carrying a truncated bt14-neo hybrid gene; pHW72 carrying a truncated bt14 gene; pVE34 carrying a truncated bt15-neo hybrid gene; and pVE35 carrying a truncated bt15 gene.

In a similar way as described for the bt14 and bt15 genes, gene cassettes are constructed for the bt3 and bt4 genes which are then expressed in *E. coli.*

EXAMPLE 3

Purification of recombinant ICPs

The ICPs expressed in *E. coli* in Example 2 are purified by the method (described for recombinant Bt2 protoxin) by Höfte et al. (1986).

EXAMPLE 4

Purification of toxins

Solubilized protoxins of Bt2, Bt3, Bt73, Bt4, Bt14, Bt15, Bt18, Bt13, Bt21 and Bt22 (in $Na_2CO_3$ 50 mM, DTT 10 mM pH=10) are dialyzed against 0.5% $(NH_4)_2CO_3$ at pH 8 and treated with trypsin (trypsin/protoxin=1/20 w/w) for 2 h at 37° C. The activated toxin is chromatographically purified (Mono-Q column on FPLC) as described by Hofmann et al.(1988b).

EXAMPLE 5

Determination of the insecticidal spectrum

The ICP protoxins and toxins of Examples 3 and 4 are evaluated for their insecticidal activity. Each protoxin is dissolved in alkaline buffer containing a reducing agent ($Na_2CO_3$ 50 mM, DTT 10 mM pH=10), and each toxin is used as soluble protein directly from FPLC. Protein concentrations are determined. Subsequently, dilutions of the resulting protoxin or toxin solution are prepared in PBS buffer pH=7.4 containing 0.15M NaCl and 0.1% bovine serum albumin ("BSA").

The artificial medium for insect culture, described by Bell and Joachim (1976) *for Manduca sexta*, is poured in appropriate receptacles and allowed to solidify. Subsequently a quantity of the (pro)toxin dilutions is applied on this medium, and the water is allowed to evaporate under a laminar flow. This results in a medium with a certain quantity (in the range of 0.1 to 10000 ng/cm2) of toxin coated on its surface. For example, for the Bt2 toxin, typical dilutions for a toxicity test on *Manduca sexta* are 1, 5, 25, 125 and 625 ng/cm2. First instar larvae of *Manduca sexta* are then applied on the coated medium, and growth and mortality are assessed after 6 days. Mortality increases with dosage. Dose response data is analysed in probit analysis (Finney, 1962), and the data are best summarized by an $LD_{50}$ value which is the amount of toxin which kills 50% of the insects. The $LD_{50}$ for Bt2 toxin against *Manduca sexta* is around 20 ng/cm2.

Figure 3:
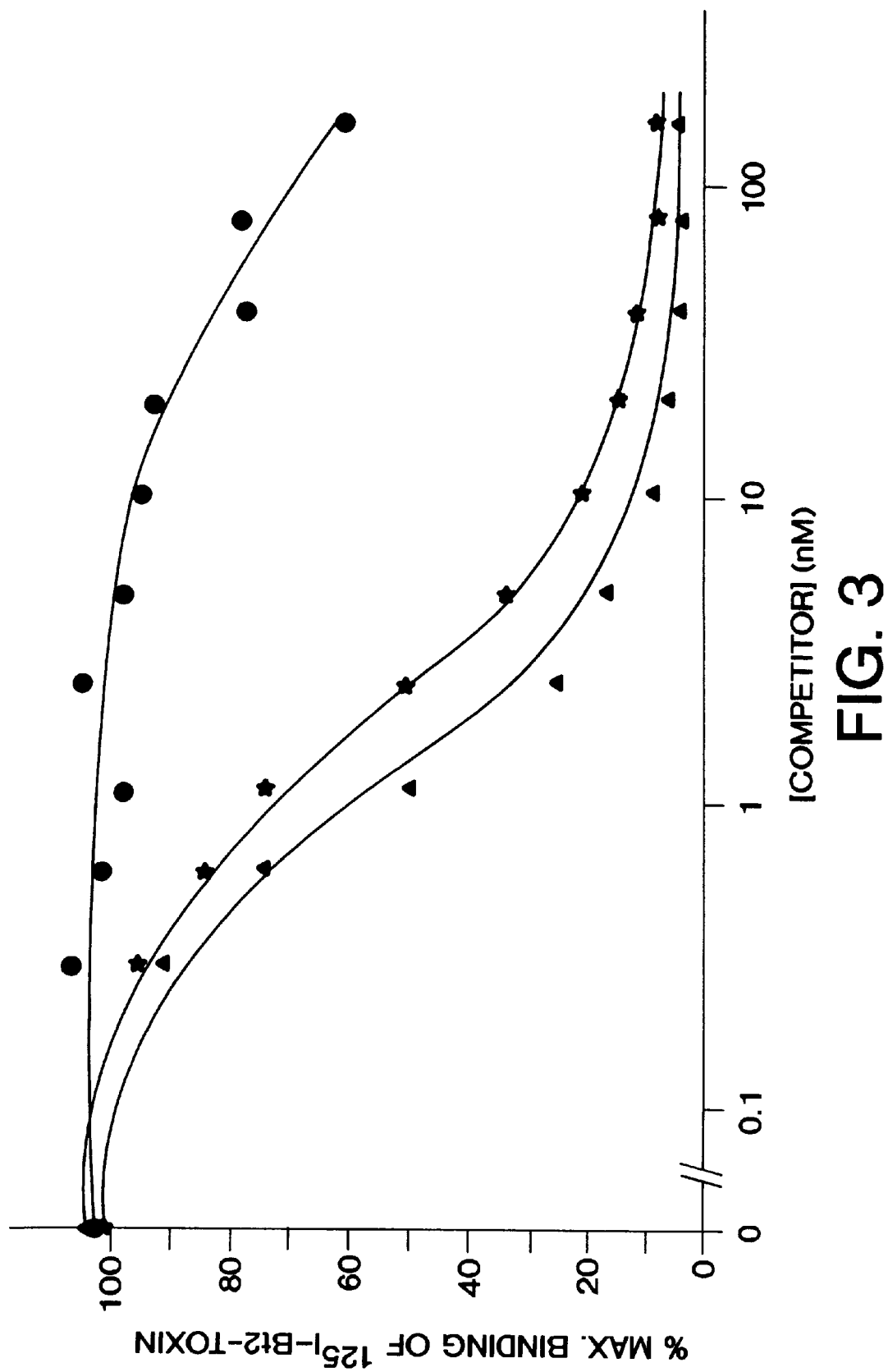
FIG. 3 is a graph showing the binding of $^{125}$I-labeled Bt73 toxin to *M. sexta* BBMV in the presence of increasing concentrations of Bt2 toxin (★), Bt3 toxin (●) or Bt73 toxin (▲).
Figure 4:
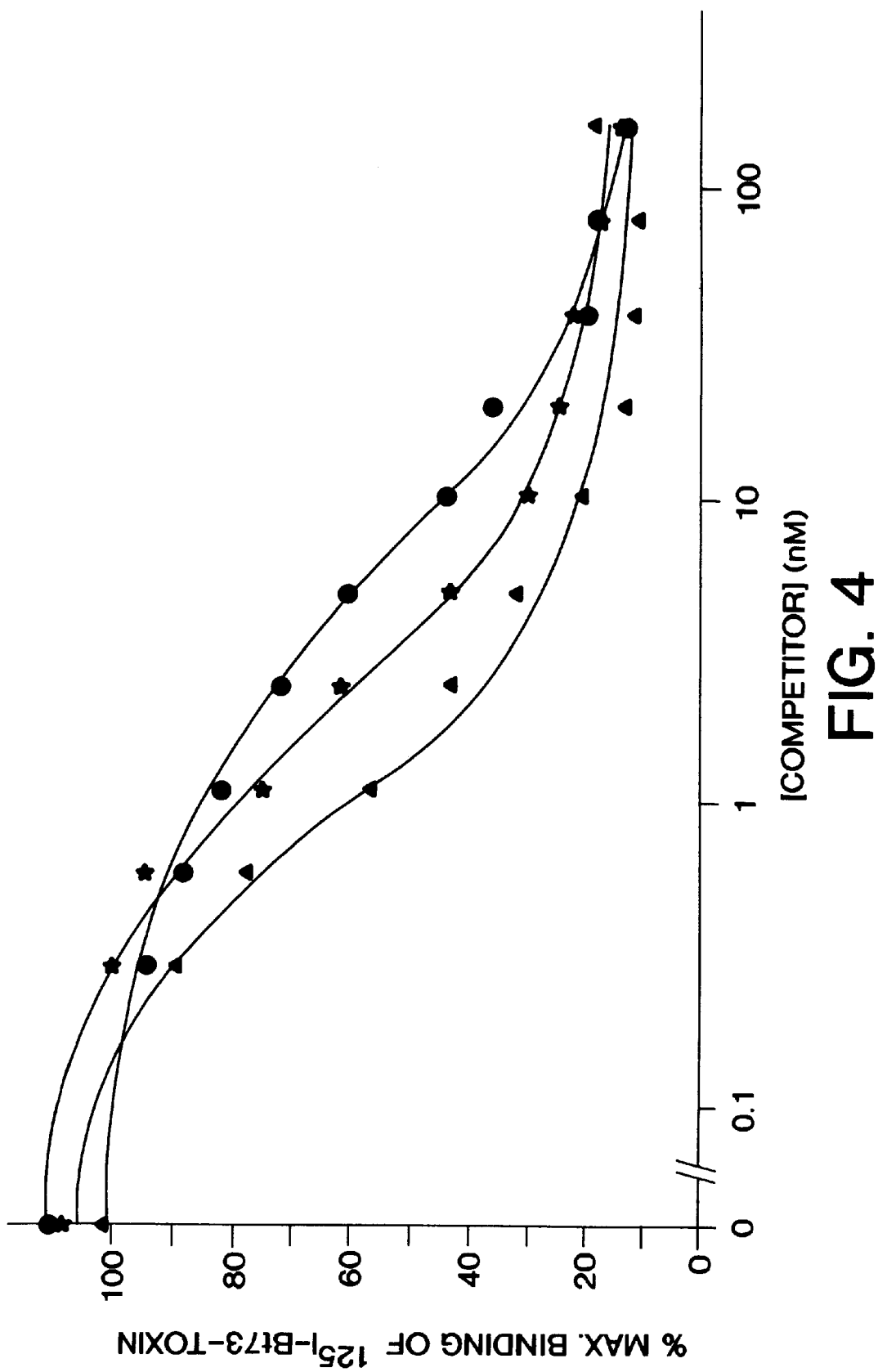
FIG. 4 is a graph showing the binding of $^{125}$I-labeled Bt2 toxin to *H. virescens* BBMV in the presence of increasing concentrations of Bt2 toxin (★), Bt3 toxin (●) or Bt73 toxin (▲).

Similar assays are carried out for other insect species using a suitable diet or by applying the ICPs on leaves for insects, for which no artificial diet is used.

EXAMPLE 6

Binding studies

Toxins

All protoxins and their toxic fragments were purified according to the methods described for the Bt2 protoxin and toxin in Höfte et al. (1986) and EP 0193259. The activated and purified toxins are further referred to as the Bt2, Bt3, Bt73, Bt4, Bt14, Bt15, Bt18, Bt13, Bt21 and Bt22 toxins.

By way of example for the Bt73 toxin, it has been shown that *B. thuringiensis* var. *kurstaki* HD73 produces a protein of 133 kDa encoded by a 6.6 kb type gene. A culture of this strain was grown as described by Mahillon and Delcour (1984). The autolysed culture was spun down (20 minutes at 4500 rpm in a HB4 rotor) and washed with a buffer containing 20 mM Tris, 100 mM NaCl and 0.05% Triton X-100, pH 8. The final pellet was resuspended in this buffer (4 ml buffer for 100 ml culture). This solution was then layered onto a linear Urograffin gradient (60–70%) which was centrifuged in a SW 28 rotor for 90 minutes at 18000 rpm. Crystals were collected and stored at −20° C. until further use. Activation was performed according to Höfte et al. (1986). The purified toxin is further referred to as the Bt73 toxin.

Iodination of ICPs

Iodination of Bt2, Bt3, and Bt73 toxins was performed using the Chloramin-T method (Hunter and Greenwood, 1962). 1 mCi $^{125}$I-NaI and 20 to 37.5 ug Chloramin-T in $NaCl/P_i$ were added to 50 ug of purified toxin. After gentle shaking for 60 seconds, the reaction was stopped by adding 53 ug of potassium metabisulfite in $H_2O$. The whole mixture was loaded on a PD 10 Sephadex G-25M gelfiltration column to remove free iodine. A subsequent run on a Biogel P-60 column was carried out in order to increase the purity.

Alternatively, toxins were labeled using the Iodogen method. Iodogen (Pierce) was dissolved in chloroform at 0.1 mg/ml. 100 ul of this solution was pipetted into a disposable glass vessel and dried under a stream of nitrogen gas. The vessel was rinsed with Tris buffer (20 mM Tris, pH 8.65 with 0.15M NaCl). 50 ug of toxin (in Tris buffer) was incubated with 1 mCi of $^{125}$I-NaI in the tube for 10 minutes. The reaction was then stopped by the addition of 1M NaI (one fourth of the sample volume). The sample was immediately loaded onto a PD10 Sephadex G-25M column and later on a Biogel P-60 column to remove free iodine and possible degradation products.

Other toxins were iodinated using one of the above mentioned procedures.

Determination of specific activity of iodinated toxin

Specific activity of iodinated Bt2, Bt3, and Bt73 toxin samples was determined using a "sandwich" ELISA technique according to Voller, Bidwell and Barlett (1976). Primary antibody was a polyclonal antiserum raised against Bt2 toxin, and the secondary antibody was a monoclonal antibody 4D6.

The conjugate used was alkaline phosphatase coupled to anti-mouse IgG. The reaction intensity of a standard dilution series of unlabeled toxin and dilutions of the iodinated toxin sample (in $NaCl/P_i$-0.1% BSA) was measured. Linear regression calculations yielded the protein content of the radioactive toxin sample. The samples with the highest specific activities were used in the binding assays. Specific activities were 59400, 33000 and 19800 Ci/mole (on reference date) for Bt73 toxin (labeled according to Iodogen procedure), Bt2 toxin (Chloramin-T method) and Bt3 toxin (Iodogen method) respectively.

Specific activities of other toxins were determined using a similar approach. Specific monoclonal and polyclonal antibodies for each of these toxins were raised and applied in ELISA.

Preparation of brush border membrane vesicles

Brush border membrane vesicles ("BBMV") from *Manduca sexta, Heliothis virescens, Plutella xylostella, Phthorimaea operculella, Spodoptera exigua, Spodoptera littoralis, Plodia interpunctella, Mamestra brassicae, Pieris brassicae* and *Leptinotarsa decemlineata* were prepared according to the method of Wolfersberger et al. (1987). This is a differential centrifugation method that makes use of the higher density of negative electrostatic charges on luminal than on basolateral membranes to separate these fractions.

Binding assay

Duplicate samples of $^{125}$I-labeled toxin, either alone or in combination with varying amounts of unlabeled toxin, were incubated at the appropriate temperature with brush border membrane vesicles in a total volume of 100 ul of Tris buffer (Tris 10 mM, 150 mM NaCl, pH 7.4). All buffers contained 0.1% BSA. The incubation temperature was 20° C. Ultrafiltration through Whatman GF/F glass fiber filters was used to separate bound from free toxin. Each filter was rapidly washed with 5 ml of ice-cold buffer ($NaCl/P_i$-0.1% BSA). The radioactivity of the filter was measured in a gamma-counter (1275 Minigamma, LKB). Binding data were analyzed using the LIGAND computer program. This program calculates the bound concentration of ligand as a function of the total concentration of ligand, given the affinity (Ka or its inverse Kd=1/Ka, the dissociation constant) and the total concentration of receptors or binding site concentration ($R_t$).

Determination of protein concentration

Protein concentrations of purified Bt2, Bt3, Bt73 and Bt15 toxins were calculated from the OD at 280 nm (measured with a Uvikon 810 P, Kontron Instruments spectrofotometer). The protein content of solutions of other toxins and of brush border membrane vesicles (BBMV) as measured according to Bradford (1976).

Binding of Bt2, Bt3 and Bt73 toxins to BBMV of *Manduca sexta* and *Heliothis virescens*: an example of 3 competitively binding Lepidopteran ICPs.

Bt2, Bt3 and Bt73 toxins are toxic to both *Manduca sexta* and *Heliothis virescens*: LC50values for *Manduca sexta* are respectively 17.70, 20.20 and 9.00 ng/cm2; for *Heliothis virescens* the LC50's are 7.16, 90.00 and 1.60 ng/cm2.

Labelled toxin, either Bt3 (0.8 nM) or Bt2 (1.05 nM) or Bt73 (1.05 nM), was incubated with BBMV in a volume of 0.1 ml. BBMV protein concentrations were 100 ug/ml for *M. sexta* and for Bt2-*H. virescens*, for Bt3-*H. virescens* 150 and for Bt73-*H. virescens* 50 ug/ml. The labelled toxin was combined with varying amounts of an unlabeled toxin (competitor). After a 30 min. incubation, bound and free toxins were separated through filtration.

FIGS. 1–3 show the percentages binding of respectively labelled Bt2, Bt3 and Bt73 toxins as a function of the concentration of competitor for *Manduca sexta*. FIGS. 4–6 show these data for *Heliothis virescens*. The amount bound in the absence of competitor is always taken as 100% binding. FIGS. 1–6 show the binding of $^{125}$I-labeled toxins to *M. sexta* (in FIGS. 1, 2 and 3) and *H. virescens* (in FIGS. 4, 5 and 6) brush border membrane vesicles. Vesicles were incubated with labeled toxin [in FIGS. 1 and 4: $^{125}$I-Bt2-toxin (1.05 nM); in FIGS. 2 and 5: $^{125}$I-Bt3-toxin (0.8 nM); in FIGS. 3 and 6: $^{125}$I-Bt73-toxin (1.05 nM)] in the presence of increasing concentrations of Bt2 toxin (★), Bt3 toxin (●) or Bt73 toxin (▲). Binding is expressed as percentage of the amount bound upon incubation with labeled toxin alone. On *M. sexta* vesicles, these amounts were 1820, 601 and 2383 cpm, and on *H. virescens* vesicles 1775, 472 and 6608 cpm for $^{125}$I-Bt2-, Bt3- and Bt73-toxin, respectively. Non-specific binding was not substracted. Data were analyzed with the LIGAND computer program. Each point is the mean of a duplicate sample.

FIG. 1: shows the binding of $^{125}$I Bt2 toxin to *M. sexta* BBMV

Figure 2:
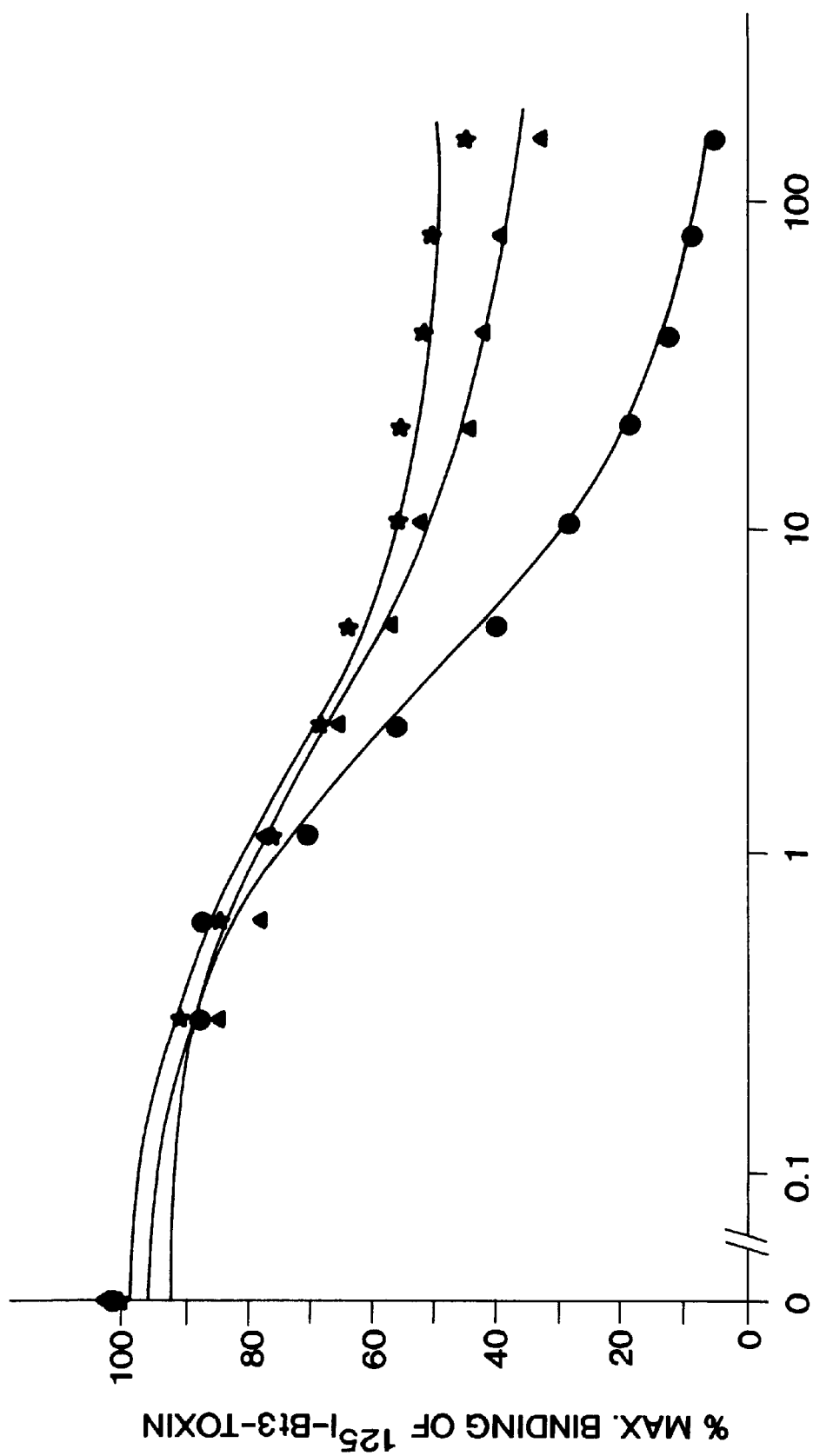
FIG. 2 is a graph showing the binding of $^{125}$I-labeled Bt3 toxin to *M. sexta* BBMV in the presence of increasing concentrations of Bt2 toxin (★), Bt3 toxin (●) or Bt73 toxin (▲).

FIG. 2: shows the binding of $^{125}$I Bt3 toxin to *M. sexta* BBMV

FIG. 3: shows the binding of $^{125}$I Bt73 toxin to *M. sexta* BBMV

FIG. 4: shows the binding of $^{125}$I Bt2 toxin to *H. virescens* BBMV

Figure 5:
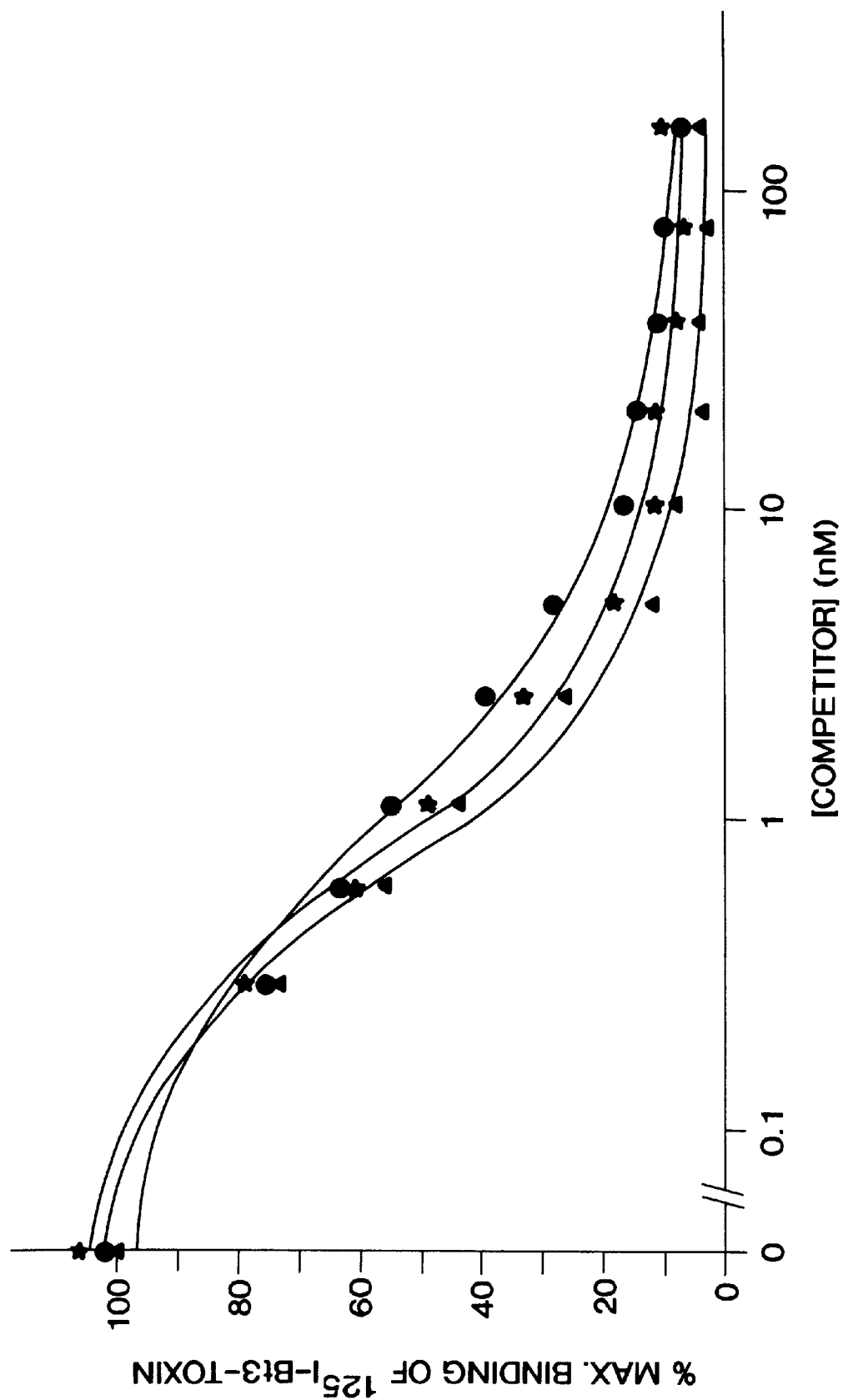
FIG. 5 is a graph showing the binding of $^{125}$I-labeled Bt3 toxin to *H. virescens* BBMV in the presence of increasing concentrations of Bt2 toxin (★), Bt3 toxin (●) or Bt73 toxin (▲).

FIG. 5: shows the binding of $^{125}$I Bt3 toxin to *H.virescens* BBMV

Figure 6:
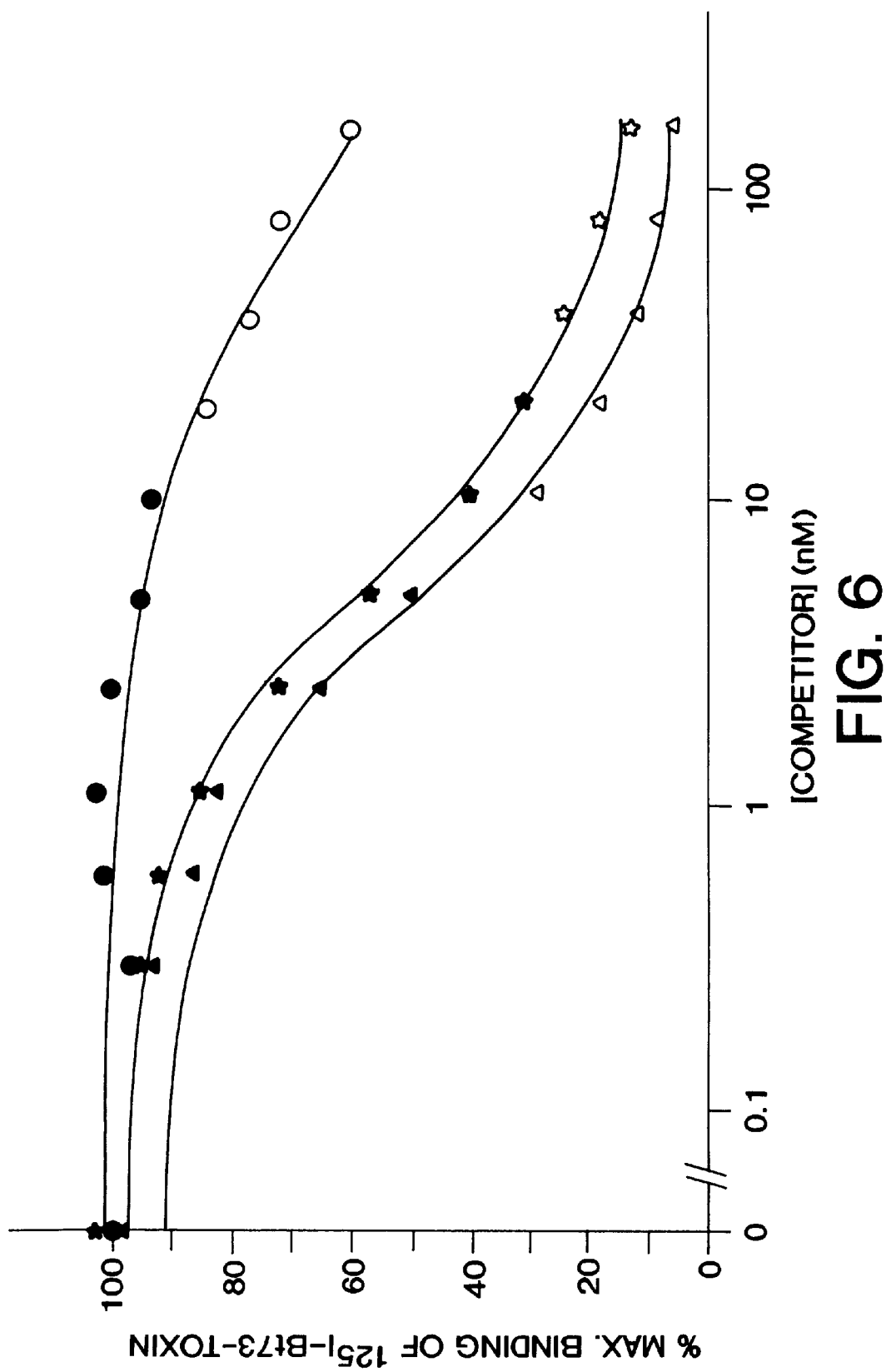
FIG. 6 is a graph showing the binding of $^{125}$I-labeled Bt73 toxin to *H. virescens* BBMV in the presence of increasing concentrations of Bt2 toxin (★), Bt3 toxin (●) or Bt73 toxin (▲).
Figure 7:
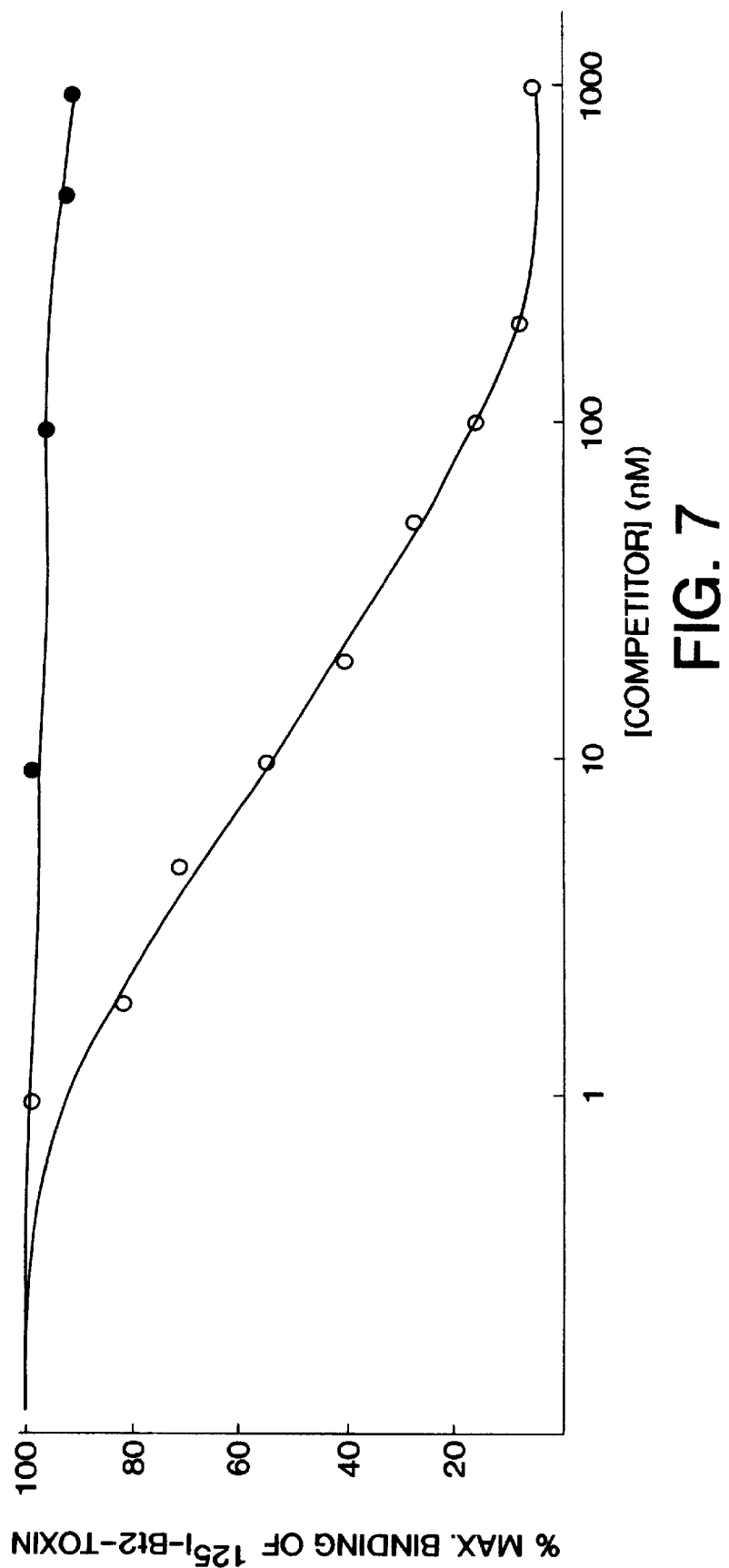
FIG. 7 is a graph showing the binding of $^{125}$I-labeled Bt2 toxin to *P. brassicae* BBMV in the presence of increasing concentrations of Bt2 toxin (○) or Bt14 toxin (●).
Figure 8:
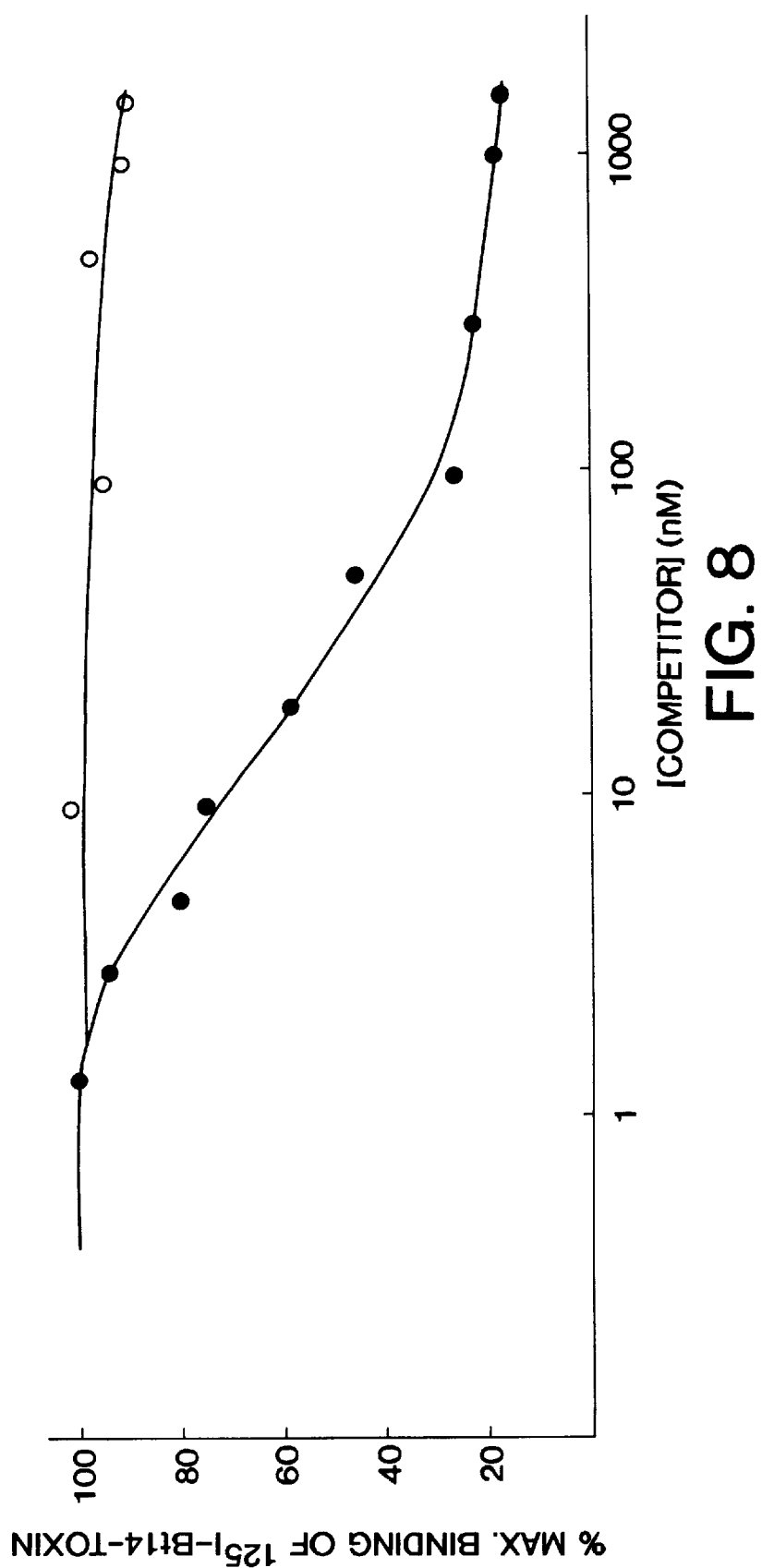
FIG. 8 is a graph showing the binding of $^{125}$I-labeled Bt14 toxin to *P. brassicae* BBMV in the presence of increasing concentrations of Bt2 toxin (○) or Bt14 toxin (●).

FIG. 6: shows the binding of $^{125}$I Bt73 toxin to *H.virescens* BBMV

Figure 9:
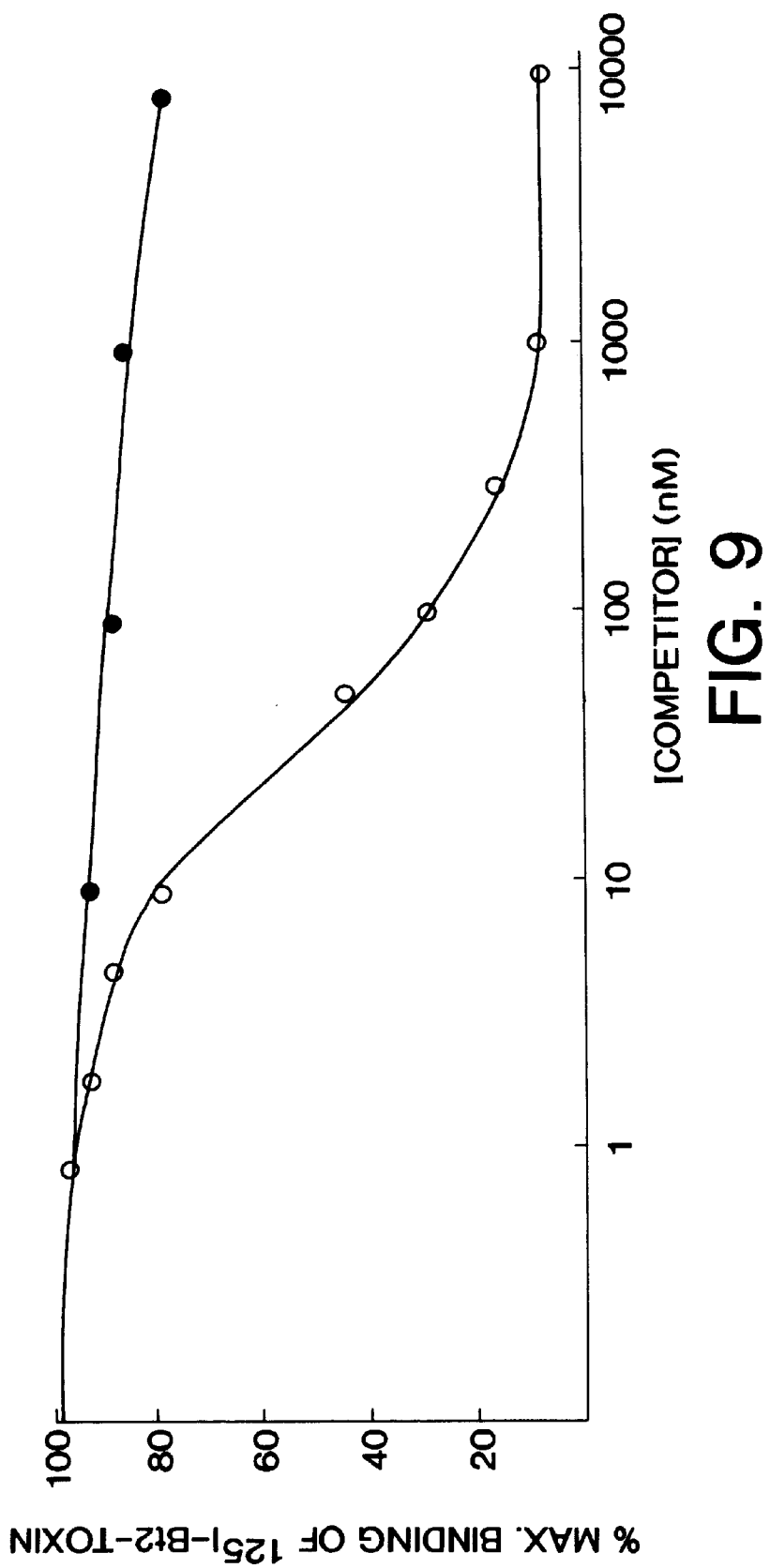
FIG. 9 is a graph showing the binding of $^{125}$I-labeled Bt2 toxin to *M. sexta* BBMV in the presence of increasing concentrations of Bt2 toxin (○) or Bt15 toxin (●).
Figure 10:
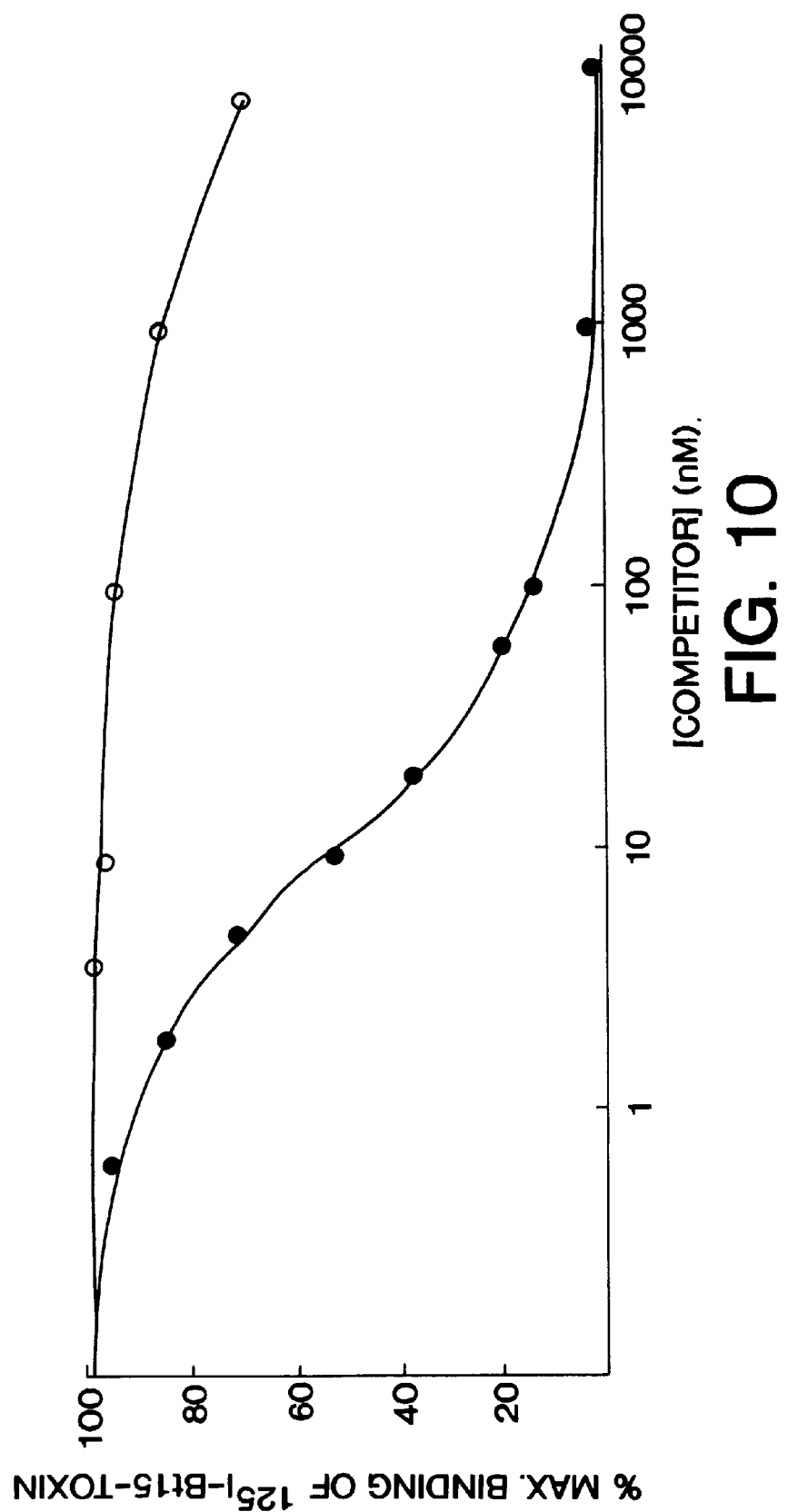
FIG. 10 is a graph showing the binding of $^{125}$I-labeled Bt15 toxin to *M. sexta* BBMV in the presence of increasing concentrations of Bt2 toxin (○) or Bt15 toxin (●).

The conclusions from FIGS. 1–6 are that Bt2 and Bt3, Bt3 and Bt73, and Bt2 and Bt73 are competitively-binding ICP's both for *Manduca sexta* and for *Heliothis virescens*. Indeed Bt3 competes for the entire population of receptor sites of Bt2 in *Manduca sexta* (FIG. 1): the % labelled Bt2 bound in the presence of 100 nM Bt3 is equal to the % Bt2 bound with 100 nM of Bt2 itself. The opposite is not true: in the presence of 100 nM Bt2 the % of labelled Bt3 is not reduced to the same level as with 100 nM of Bt3 (FIG. 2).

A similar reasoning is followed to observe competitivity of other toxin combinations: Bt3 competes for the entire population of receptor sites of Bt73 (FIG. 3) in *M. sexta*; the opposite is not true (FIG. 2); Bt2 and Bt73 compete for the entire population of each other's binding sites in *M. sexta* (FIGS. 1 and 3).

In *Heliothis virescens:* Bt2 competes for the entire population of receptor sites of Bt3 (FIG. 5); Bt73 competes for the entire population of receptor sites of Bt3 (FIG. 5); Bt73 competes for the entire population of receptor sites of Bt2 (FIG. 4); but the opposite statements are not true (FIGS. 4, 5 and 6).

The same data can be used in mathematical analysis (e.g., Scatchard analysis according to Scatchard, 1949; analysis with the LIGAND computer program according to Munson and Rodbard, 1980) to calculate the dissociation constant (Kd) of the toxin-receptor complex and the concentration of binding sites (Rt); the results of these calculations using the LIGAND computer program were the following:

| | | |
|---|---|---|
| Bt2-*M. sexta:* protein | Kd = 0.4 nM | Rt = 3.4 pmol/mg vesicle |
| Bt3-*M. sexta:* protein | Kd = 1.5 nM | Rt = 9.8 pmol/mg vesicle |
| Bt73-*M. sexta:* protein | Kd = 0.6 nM | Rt = 4.0 pmol/mg vesicle |
| Bt2-*H. virescens:* protein | Kd = 0.6 nM | Rt = 9.7 pmol/mg vesicle |
| Bt3-*H. virescens:* protein | Kd = 1.2 nM | Rt = 3.7 pmol/mg vesicle |
| Bt73-*H. virescens:* protein | Kd = 0.8 nM | Rt = 19.5 pmol/mg vesicle |

These data demonstrate the high affinity receptor binding of the toxins (Kds in the range of $10^{-10}$ to $10^{-9}$M.

Binding of Bt2 and Bt14 toxins to BBMV of *P. brassicae, Plutella xylostella* and *Phthorimaea opercullella*: an example two non-competitively binding Lepidopteran ICPs Bt2 and Bt14 toxins are toxic to *P. brassicae* (p.b.), *P. xylostella* (p.x.) and *P. operculella* (p.o.) as seen from the table below.

| | LC$_{50}$ of Toxins | |
|---|---|---|
| | Bt2 | Bt14 |
| P.b. | 1.3 | 2.0 |
| P.x. | 6.7 | 5.4 |
| P.o. | 4.20 | 0.8–4.0 |

LC$_{50}$ values of solubilized purified Bt2 and Bt14 toxins for P. x. are expressed as ng protein spotted per cm$^2$ of artificial diet. LC$_{50}$ values for P. b. are expressed as ug$^2$ toxin per ml solution into which leaf discs, fed to first instar Pb larvae, were dipped. For P. o., LC$_{50}$ values are expressed in ug/ml into which potato chips were dipped prior to feeding.

Labelled Bt2 toxin (1.05 nM) or Bt14 toxin (1.4M) was incubated with BBMV from *P. brassicae* (100 ug protein/ml) in a volume of 0.1 ml in combination with varying amounts of unlabelled Bt2 or Bt14. After a 30 min. incubation period at 22° C., the bound and free toxins were separated.

FIGS. 7 and 8 show the binding of $^{125}$I-labeled toxins to *P. brassicae* brush border membrane vesicles. Vesicles were incubated with labeled toxin [in FIG. 7: $^{125}$I-Bt2-toxin (1.05 nM); in FIG. 8: $^{125}$I-Bt14-toxin (1.4 nM)] in the presence of increasing concentrations of Bt2 toxin (○) or Bt14 toxin (●). Binding is expressed as percentage of the amount bound upon incubation with labeled toxin alone. Non-specific binding was not substracted. Data were analyzed with the LIGAND computer program. Each point is the mean of a duplicate sample. FIG. 7 shows the binding of labelled Bt2 toxin to *P. brassicae* BBMV, and FIG. 8 shows the binding of labelled Bt14 toxin to *P. brassicae* BBMV.

The competition data demonstrate the presence of high affinity binding sites both for Bt2 and Bt14, as well as the almost complete absence of competition of Bt14 for the Bt2 binding sites and of Bt14 for the Bt2 binding sites. This demonstrates that Bt2 and Bt14 are non-competitively binding toxins. Hence they are useful to prevent the development of *Pieris brassicae* resistance against *B. thuringiensis* ICP's expressed in Brassica sp.

Calculated Kd and Rt values were from these experiments were:

Bt2: Kd=2.8 nM, Rt=12.9 pmol/mg vesicle protein Bt14: Kd=8.4 nM, Rt=21.4 pmol/mg vesicle protein. Binding of Bt2 and Bt15 toxins to BBMV of *M. sexta, M. brassicae, P. xylostella* and *P. interpunctella:* an example of two non-competitively binding Lepidopteran IcPs Bt2 and Bt15 toxins are both toxic to *M. sexta* (LC50's of 20 and 111 ng/cm2, respectively). They also show activity against *M. brassicae, P. xylostella* and *P. interpunctella.*

Labelled Bt2 (1.05 nM) or Bt15 (0.7 nM) was incubated with BBMV from *M. sexta* (100 ug protein/ ml) in a volume of 0.1 ml in combination with varying amounts of unlabelled Bt2 or Bt15. After a 30 min. incubation period at 22° C., the bound and free toxins were separated.

FIGS. 9–10 show the binding of $^{125}$I-labeled toxins to *M. sexta* brush border membrane vesicles. Vesicles were incubated with labeled toxin [in FIG. 9: $^{125}$I-Bt2-toxin (1.05 nM); in FIG. 10: $^{125}$I-Bt15-toxin (0.7 nM)] in the presence of increasing concentrations of Bt2-toxin (○) or Bt15-toxin (●). Binding is expressed as percentage of the amount bound upon incubation with labeled toxin alone. Nonspecific binding was not substracted. Data were analyzed with the LIGAND computer program. Each point is the mean of a duplicate sample. FIG. 9 shows the data for binding of labelled Bt2, and FIG. 10 shows the binding of labelled Bt15.

The competition data demonstrate the presence of high affinity binding sites for both Bt2 and Bt15, as well as the complete absence of competition of Bt15 for the Bt2 binding sites and of Bt2 for the Bt15 binding sites. This demonstrates that Bt2 and Bt15 are non-competitively binding toxins. Hence the combination of Bt2 and Bt15 is useful to prevent the development of resistance of *M. sexta* against *B. thuringiensis* ICP's expressed in tobacco or other crops in which Manduca sp. are a pest. Calculated Kd and Rt values are: Bt2: Kd=0.4 nM, Rt=3.4 pmol/mg vesicle protein Bt15: Kd=0.3 nM Kd2=2.9 nM, Rt1=5.9 and Rt2=6.7 pmol/mg vesicle protein (2 distinct high affinity receptor sites are present).

Similar studies were performed for *S. littoralis* and *P. interpunctella*; and are also performed form *M. brassicae*. Although LD50, Kd and Rt values differed substantially, the essential observation that Bt2 and Bt15 are both toxic and are non-competitively binding toxins was confirmed in these three insect species. Thus, it is also a useful toxin combination to prevent resistance of *M. brassicae* to ICP's or to prevent resistance of Spodoptera species against ICP's expressed in any of the crop plants in which Spodoptera species are a pest.

Binding of Bt2 and Bt4 toxins to BBMV of *M. sexta*: an example of two non-competitively binding Lepidopteran ICPs Both Bt2 and Bt4 toxins are toxic to *Manduca sexta*. LD50 values are 20 and 5.4. ng/cm2, respectively. No mutual competition of Bt2 for binding of labelled Bt4 and of Bt4 for binding of labelled Bt2 was observed, demonstrating that Bt2 and Bt4 are non-competitively binding toxins.

Binding of Bt15 and Bt18 toxins to BBMV of *S. littoralis*: an example of two non-competitively binding Lepidopteran ICPs Both Bt15 and Bt18 toxins are toxic to *S. littoralis*. LD 50 values are 93 and 88 ng toxin/cm$^2$, respectively. Labelled Bt15 (0.7 nM) or Bt18 (0.9 nM) was incubated with 100 ug of vesicle protein from *S. littoralis* in combination with varying amounts of unlabelled Bt15 or Bt18 toxin. After a 45 min. incubation period, bound and free toxins were separated. Binding data demonstrate high affinity binding for both Bt15 and Bt18 to *S. littoralis* BBMV. As seen from FIGS. 11 and 12, the entire population of receptor sites of Bt15 was not saturable with Bt18, nor was the entire population of receptor sites of Bt18 saturable with Bt15.

Binding of Bt13 and Bt22 toxins to BBMV of *L. decemlineata*: an example of two non-competitively binding Coleopteran ICPs.

Both Bt13 and Bt22 toxins are toxic to *L. decemlineata*. LD 50 values are 0.8 and 1.1 ug toxin/ml respectively. Labelled Bt13 (1 nM) or Bt22 (0.7 nM) was incubated with 100 ug of vesicle protein/ml from *S. littoralis* in combination with varying amounts of unlabelled Bt13 or Bt22 toxin. After a 45 min. incubation period, bound and free toxins were separated. Binding data demonstrate high affinity binding for both Bt13 and Bt22 to *S. littoralis* BBMV. The entire population of receptor sites of Bt13 was not saturable with Bt22. Nor is the entire population of receptor sites of Bt22 saturable with Bt13.

Binding of Bt2 and Bt18 toxins to BBMV of *M. sexta*: an example of two non-competitively binding Lepidopteran ICPs Both Bt2 and Bt18 toxins are toxic to *M. sexta*, and LD 50 values are 20 to 73 ng toxin/cm$^2$ respectively. Labelled Bt2 (1.05 nM) or Bt18 (0.7 nM) was incubated with 100 ug/ml of vesicle protein from *M. sexta* in combination with varying amounts of unlabelled Bt2 or Bt18 toxin. After a 45 min. incubation period, bound and free toxins were separated. Binding data (FIGS. 11–12) demonstrate high affinity binding for both Bt2 and Bt18 to *M. sexta* BBMV. The entire population of receptor sites of Bt2 was not saturable with Bt18. Nor was the entire population of receptor sites of Bt18 saturable with Bt2. Calculated Kd and Rt values are:

Bt2: Kd=0.4 nM, Rt=3.4 pmol/mg vesicle protein. Bt18: Kd1=0.04 nM, Rt1=2.2 pmoles/mg vesicle protein and Kd2=168 nM Rt2=194 pmoles/mg vesicle protein (2 distinct receptor sites for Bt18 are present).

A list of non-competitively binding anti-Lepidopteran ICP combinations is given below, together with their common target insect species in which non-competitivity has been demonstrated:

Bt2-Bt15 (*Manduca sexta, Plutella xylostella, Plodia interpunctella*)

Bt2-Bt18 (*Manduca sexta, Spodoptera littoralis*)

Bt2-Bt14 (*Pieris brassicae, Plutella xylostella, Phthorimaea operculella*)

Bt2-Bt4 (*Manduca sexta*)

Bt15-Bt18 (*Manduca sexta, Spodoptera littoralis*)

Bt15-Bt4 (*Manduca sexta*)

Bt18-Bt4 (Manduca sexta, Spodoptera littoralis)

Bt18-Bt4 (*Manduca sexta*)

Also included in this list of non-competitively binding ICP combinations, together with their common target insect species in which non-competitively is demonstrated are:

Bt2-Bt15 (*Pieris brassicae, Mamestra brassicae*)

Bt14-Bt15 (*Pieris brassicae*)

Bt15-Bt4 (*Spodoptera exigua*)

Bt18-Bt14 (*Pieris brassicae*)

Bt13-Bt21 (*Lepinotarsa decemlineata*)

Bt13-Bt22 (*Lepinotarsa decemlineata*)

Bt21-Bt22 (*Lepinotarsa decemlineata*)

Of course, this list of specific non-competitively binding ICP combinations for specific target insect pests is not exhaustive, and it is believed that other such ICP combinations, including combinations for yet-to-be discovered ICPs, will be found using a similar approach for any target insect species. Likewise, the foregoing list of target insect pests also is not exhaustive, and it is believed that other target insects pests (as well as the plants that are to be transformed to prevent their attack by such pests), against which the specific combinations of ICPs can be used (e.g., the combination of the Bt2 and Bt14 ICPs in Brassica to prevent resistance of *Pieris brassicae* against the ICPs expressed in the plant), will be found using a similar approach.

EXAMPLE 7

Selection for resistance of i Manduca sexta(tobacco hornworm)

A selection experiment involves exposing a large number of larvae to a concentration of a toxin in a diet killing (e.g., 50–90%) of the larvae. The surviving larvae are again exposed to toxin concentrations killing a similar proportion of the larvae, and this process is continued for several generations. The sensitivity of the larvae to the toxin is investigated after each four generations of selection.

Selections for 20 generations of *M. sexta* were performed with Bt2 toxin alone, with Bt18 toxin alone and with a 1/4 (by weight) Bt2/Bt18 mixture. LC50 values of the reference strain for Bt2, Bt18 and the 1/4 Bt2/Bt18 mixture respectively were the following: 20 ng/cm2, 73 ng/cm2 and 62 ng/cm2 of diet.

Selection was initiated at concentrations killing around 75% of the larvae. After 4 generations of selection, survival increased in both the Bt2 and the Bt18 selection to around 70%, no such increase was observed in the selection with the combination of Bt2 and Bt18. Dosages were again increased to calculated LC75 values. This was repeated every 4 generations. The selection process was thus continued to the 20th generation. Final results were the following (LC50 of the 20th generation):

Bt2 selection: LC50 was 6400 ug/g (320 times decreased sensitivity)

Bt18 selection: LC50 was 15100 ug/g (207 times decreased sensitivity)

Bt2/Bt18 selection: LC50 was 181 ug/g (3 times decreased sensitivity).

Thus the decrease in sensitivity was about 100 times slower in the combined selection experiment.

Receptor binding in the three selected *M. sexta* strains was investigated with Bt2 and Bt18 and compared to those of the reference *M. sexta* strain (non-selected strain). Binding characteristics of the reference strain for the Bt2 and BT18 toxins were:

Bt2: Kd=0.4 nM, Rt=3.4 pmol/mg vesicle protein

Bt18: Kd1=0.04 nM, Rt1=2.2 pmoles/mg vesicle protein and Kd2=168nM, Rt2=194 pmoles/mg vesicle protein (2 distinct receptor sites for Bt18 are present).

Figure 11:
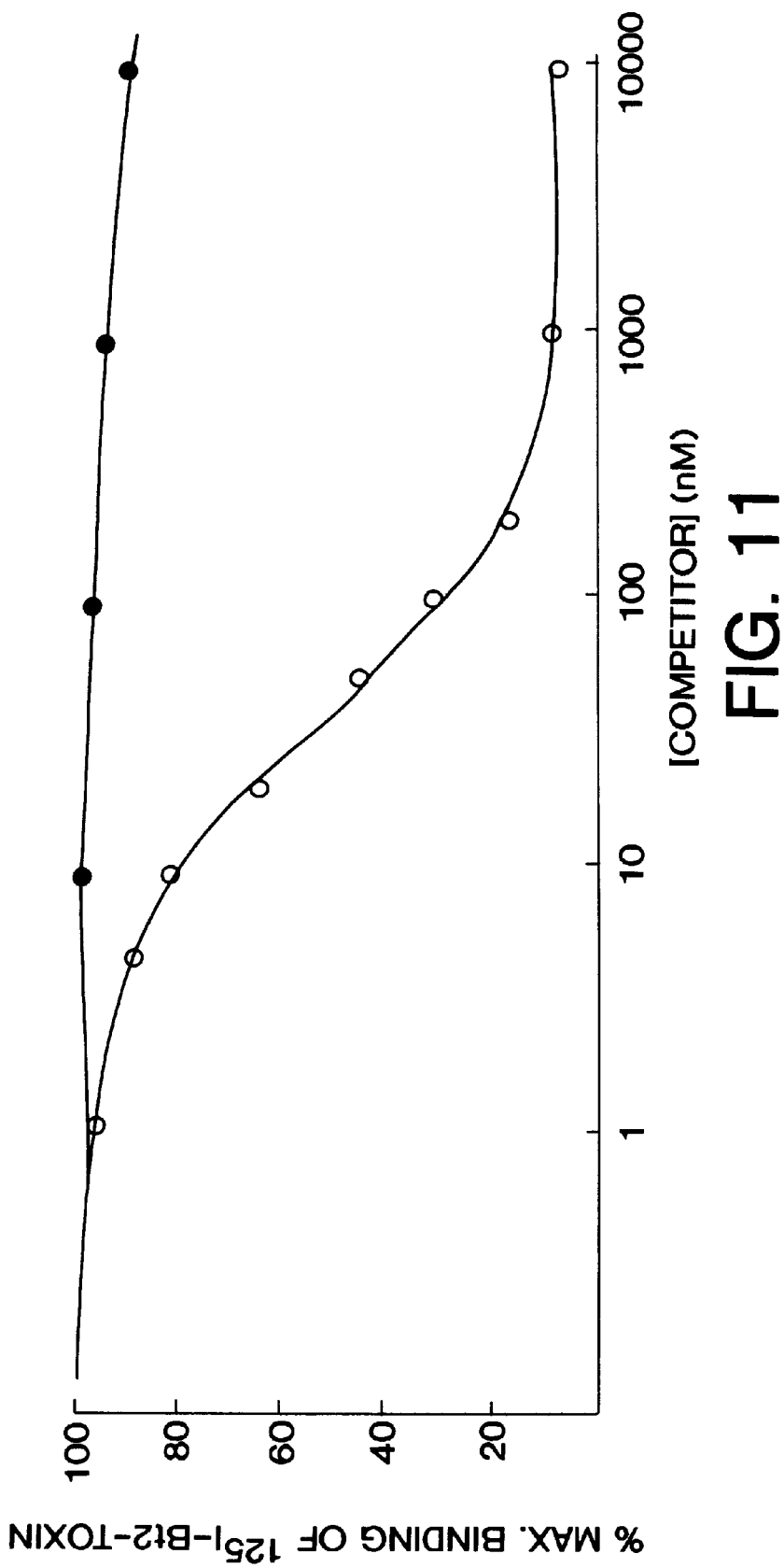
FIG. 11 is a graph showing the binding of $^{125}$I-labeled Bt2 toxin to *M. sexta* BBMV in the presence of increasing concentrations of Bt2 toxin (○) or Bt18 toxin (●).
Figure 12:
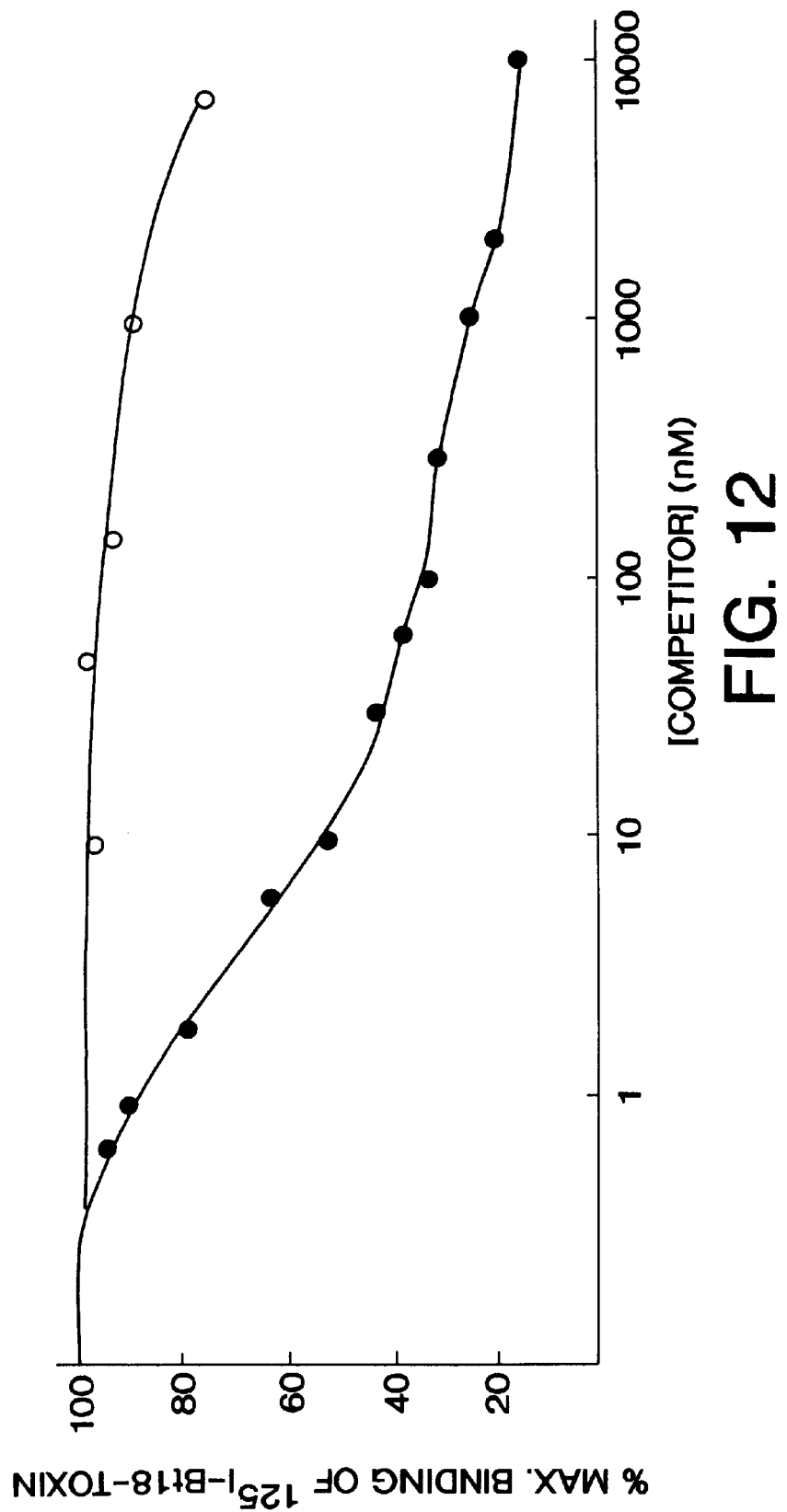
FIG. 12 is a graph showing the binding of $^{125}$I-labeled Bt18 toxin to *M. sexta* BBMV in the presence of increasing concentrations of Bt2 toxin (○) or Bt18 toxin (●).

FIGS. 11 and 12 show the binding of $^{125}$I-labeled toxins to *M. sexta* brush border membrane vesicle. Vesicles were incubated with labeled toxin [in FIG. 11: $^{125}$I-Bt2-toxin (1.05 nM); in FIG. 12: $^{125}$I-Bt18-toxin (0.7 nM)] in the presence of increasing concentrations of Bt2-toxin (○) or Bt18-toxin (●). Binding is expressed as percentage of the amount bound upon incubation with labeled toxin alone. Non-specific binding was not substracted. Data were analyzed with the LIGAND computer program. Each point is the mean of a duplicate sample.

The Bt2 selected strain showed no detectable high affinity binding of Bt2 whereas its Bt18 binding characteristics remained close to the reference strain. (Bt18: Kd1=0.03 nM, Rt1=2.8 pmoles/mg vesicle protein and Kd2=199nM, Rt2= 109 pmoles/mg vesicle protein; 2 distinct receptor sites for Bt18 are still present).

The Bt18 selected strain lost the high affinity receptor site for Bt18. The lower affinity site for Bt18 was still present in lower concentration than in the reference strain (Kd=189 nM, Rt=43 nM). Bt2 binding site concentration increased markedly compared to the reference strain (Kd=0.4 nM, Rt=20.8 pmoles/mg vesicle protein). This strain had a Bt2 sensitivity of $LC_{50}$=4 ng/cm$^2$. Thus, its sensitivity for Bt2 had increased as compared to the reference strain ($LC_{50}$=20 ng/cm$^2$).

The Bt2/Bt18 selected strain showed a slight but statistically non-significant decrease in Bt18 binding site concentration. (Bt2: Kd=0.4 nM, Rt=3.4 pmol/mg vesicle protein, Bt18: Kd1=0.04 nM, Rt1=1.0 pmoles/mg vesicle protein and Kd2=168 nM, Rt2=194 pmoles/mg vesicle protein; 2 distinct receptor sites for Bt18 are present). These data demonstrate that, in the two selection lines where resistance occurred, the mechanism was situated at the receptor level. Changes in receptor site are shown to be the most likely mechanism of resistance to *B. thuringiensis* ICPs.

EXAMPLE 8

Mechanism of resistance of the diamondback moth to the microbial insecticide *Bacillus thuringiensis*.

The mechanism of development of insect resistance to ICPs has been investigated in a *P. xylostella* strain ("PxR"). This insect strain has developed a high level of resistance in the field against Dipel. Crystals of Dipel preparations contain a mixture of ICPs such as Bt3, Bt2 and Bt73 ICPs; in Example 6, it has been shown that these toxins are competitively binding ICPs.

Resistance to Dipel was confirmed by the toxicity data for the sensitive strain ("PxS") and for the Dipel-resistant strain ("PxR"). High levels of resistance are also observed for the Bt2 protoxin and toxin as shown in the following table:

| | $LC_{50}$ of Strains | |
|---|---|---|
| | PxS | PxR |
| Bt2 | 6.7 | >1350 |
| Bt15 | 132.6 | 120.4 |

LC50 data are expressed as ng protein spotted per cm$^2$ of artificial diet.

However, insect toxicity data show that there is no resistance to the Bt15 protoxin and Bt15 toxin; this ICP is not present in Dipel crystals. To investigate whether a change in toxin-membrane binding was responsible for resistance, receptor binding studies were performed with $^{125}$I-labeled Bt2 toxin and Bt15 toxin, with BBMV derived from larvae midguts of the PxR and PxS strains. The results are summarized in Table 1, below.

Table 1. Binding characteristics of Bt2 and Bt15 toxins to brush border membrane vesicles from sensitive and resistant *P. xylostella*.

| ICP | strain | kd (nM) | Rt (pmol/ mg protein) |
|---|---|---|---|
| Bt2 toxin | PxS | 8.1 | 1.6 |
| | PxR | no binding detectable | |
| Bt15 toxin | PxS | 1.9 | 4.2 |
| | PxR | 3.7 | 5.8 |

Table 1 shows that there was high-affinity saturable binding of the Bt2 toxin to midgut membranes of the PxS strain, but the PxR strain showed no detectable level of Bt2 toxin binding. With the Bt15 toxin, there was significant binding to BBMW of both the PxR and PxS strains, and values are not significantly different for the two strains.

These data show that resistance in *P. xylostella* is due to an alteration in toxin-membrane binding. Resistance to the Bt2 toxin and the sensitivity toward the Bt15 toxin of the PxR strain is reflected by the binding characteristics shown in Table 1.

Hence, when different non-competitively binding ICPs (i.e., Bt2 and Bt15) are available with activity against the same insect species (e.g., *P. xylostella*), resistance to one ICP(Bt2) does not imply resistance against other ICPs (such as Bt15). Thus, ICPs with different binding properties can be used in combination to delay development of insect resistance to ICPs.

EXAMPLE 9

Separate transfer of two ICP genes within individual transcriptional units to the genome of plant cells Two procedures are envisaged for obtaining the combined expression of two ICP genes, such as the bt2 and bt15 genes in transgenic plants, such as tomato plants. These procedures are based on the transfer of two chimeric ICP genes, not linked within the same DNA fragment, to the genome of a plant of interest.

A first procedure is based on sequential transformation steps in which a plant, already transformed with a first chimeric ICP gene, is retransformed in order to introduce a second ICP gene. The sequential transformation makes use of two different selectable marker genes, such as the resistance genes for kanamycin ("km") and phosphinotricin acetyl transferase ("PPT"), which confers resistance to phoshinotricin. The use of both these selectable markers has been described in De-Block et al. (1987).

The second procedure is based on the cotransformation of two chimeric ICP genes on different plasmids in a single step. The integration of both ICP genes can be selected by making use of the two selectable markers conferring resistance to Km and PPT, linked with the respective ICP genes.

For either procedure, a Ti-plasmid vector is used for Agrobacterium-mediated transformation of each chimeric ICP gene into plant cells.

Plasmid pGSH163, described in EP 0193259, contains the following chimeric genes between the T-DNA border repeats: a gene fragment encoding the toxin part of the bt2 gene under the control of the TR2' promoter and the neo gene under control of the TR1' promoter. The 3' ends of the T-DNA gene 7 and octopine synthase respectively provide information for the 3' end formation of transcripts.

A chimeric bt15 gene containing a gene fragment encoding the toxin of the Bt15 ICP under the control of the TR2' promoter, was constructed in the following way (FIG. 15). pOH50 consists of pUC18 with the whole bt15 gene under the control of the lac promoter. A HindIII-BglII fragment was cloned in pMa5-8 yielding pJB3. By site-directed mutagenesis, a NcoI site was created at the initiation codon to yield pVE29. A fragment containing the truncated gene fragment of the bt15 gene, with a translational stop codon, was obtained by isolation of BclI-ClaI from pOH50 and cloning in pLK91, yielding pHW38. The whole toxin gene fragment was reconstructed under the control of the tac promoter, yielding pVE35, by ligation of a ClaI-PstI fragment from pHW38, a NcoI-ClaI fragment from pVE29 and a NcoI-PstI fragment from pOH48. A truncated bt15 gene fragment with a NcoI site at the initiation codon was obtained from pVE35 as a 1980 NcoI-BamHI fragment and cloned in pGSJ141, digested with ClaI and BamHI. pGSJ141 has been described in EPA 88402115.5. Ligation of the filled ClaI site to the filled NcoI site yielded a chimeric TR2'-truncated bt15 -3'g7 construct (pTVE47). As a selectable marker in this plasmid, the bar gene encoding phosphinothricin acetyl transferase and conferring resistance to PPT was used. A chimeric bar gene containing the bar gene under the control of the 35S promoter and followed by the 3' end of the octopine synthase was introduced in pTVE47. From pDE110, a 35S-bar-3'ocs fragment was obtained as a StuI-HindIII fragment and was cloned in pTVE47 digested with PstI and HindIII. This yielded the plasmid pTHW88 (FIG. 15) which contains the truncated bt15 gene under the control of the TR2' promoter and the bar gene under the control of the 35S promoter between the T-DNA border repeats. Plasmid pGSH163 is cointegration type Ti-plasmid vector, whereas pTHW88 is a binary type Ti-plasmid vector as described in EPA 0193259.

Both plasmids were mobilized in the A. tumefaciens strain C58C1Rif (pGV2260) according to Deblaere et al. (1988).

In the sequential transformation procedure, tomato was transformed according to De Block et al. (1987) with the A. tumefaciens strain C58C1Rif carrying pGS1163 resulting from the cointegration of pGSH163 and pGV2260. Individual transformants were selected for kanamycin resistance, and regenerated plants were characterized for expression of the truncated bt2 gene according to Vaeck et al. (1987). One representative transformant was subsequently retransformed with the A. tumefaciens strain C58C1Rif (pGV2260 and pTHW88), and transformants were selected for PPT resistance. Using this cotransformation procedure, the respective Agrobacteria strains, carrying the cointegrate vector pGS1163 and the binary vector pTHW88, were used for transformation of tomato. Individual plants were selected for resistance to Km and PPT.

Figure 15A:
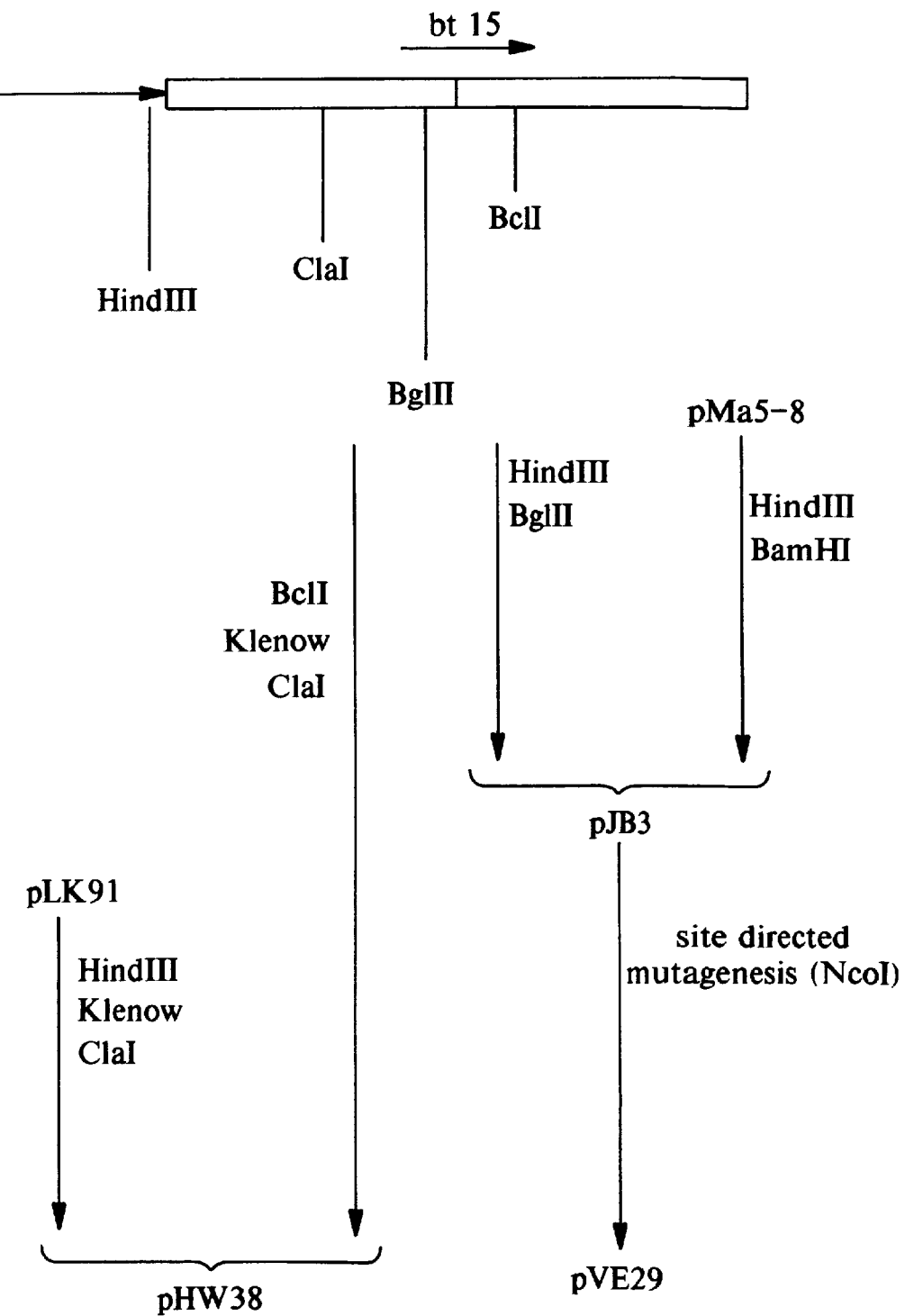
FIGS. 15A–15C schematically depict construction of pVE29, PVE35 and pTHW88.
Figure 15B:
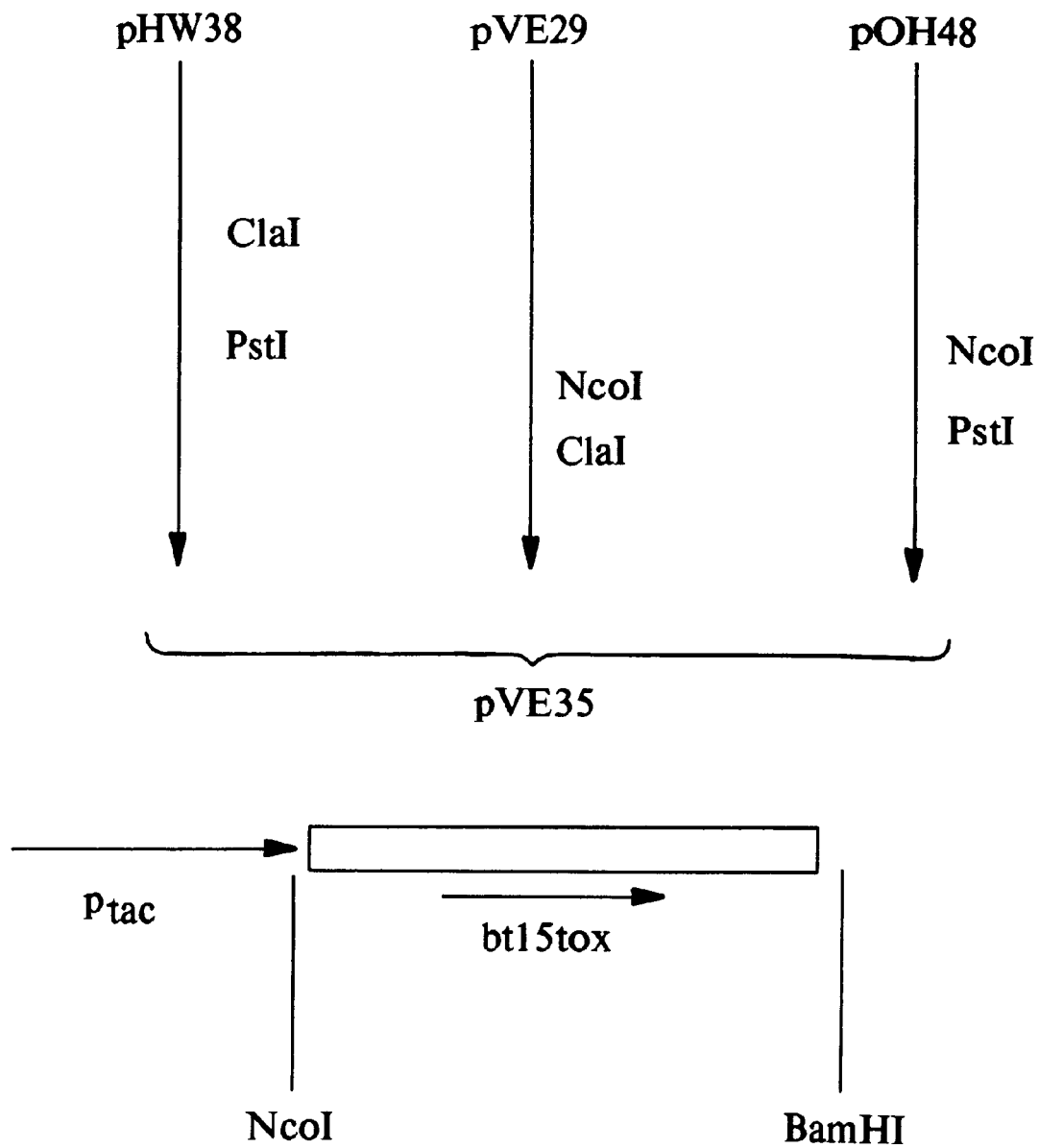
Figure 15C:
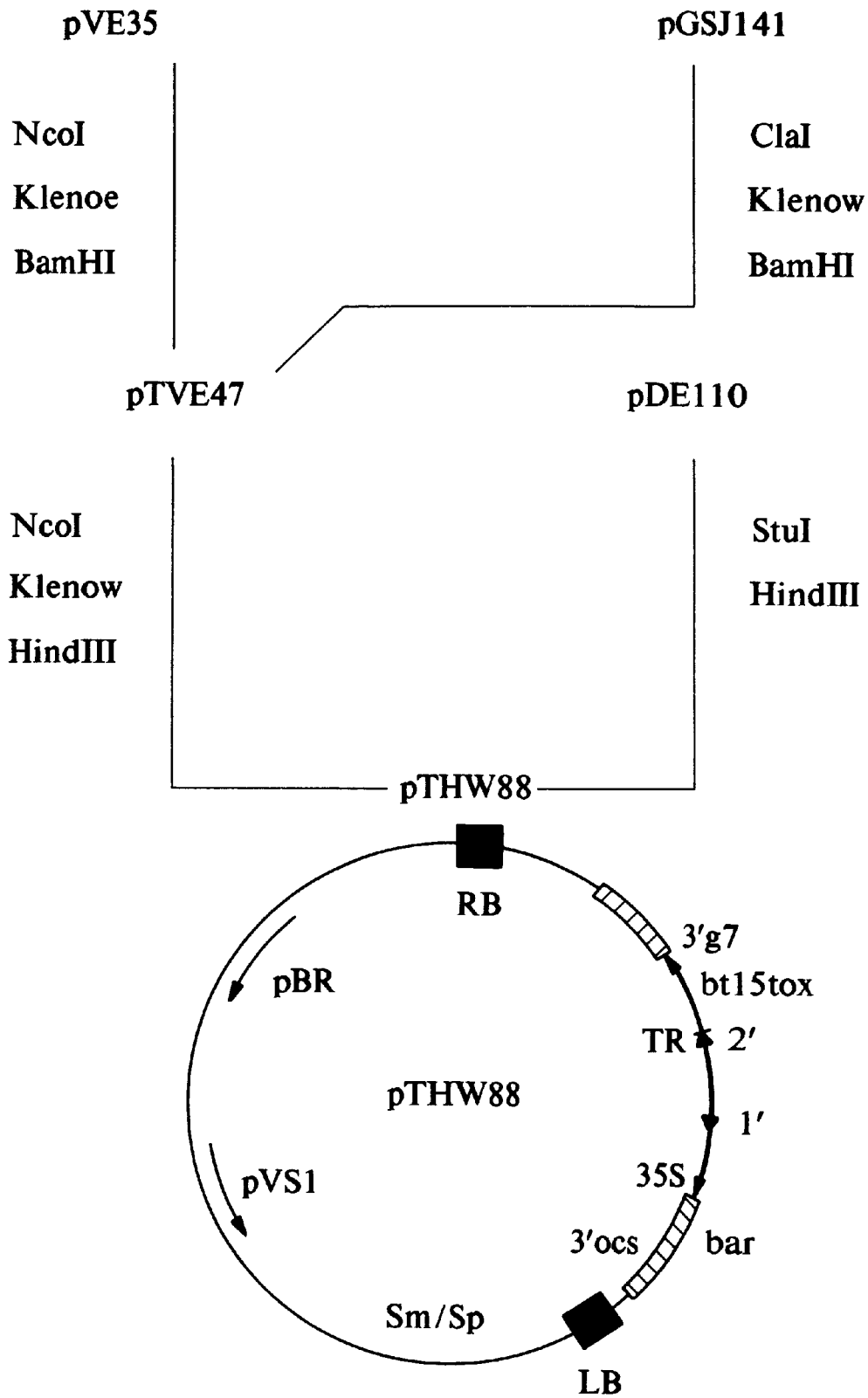
Figure 16A:
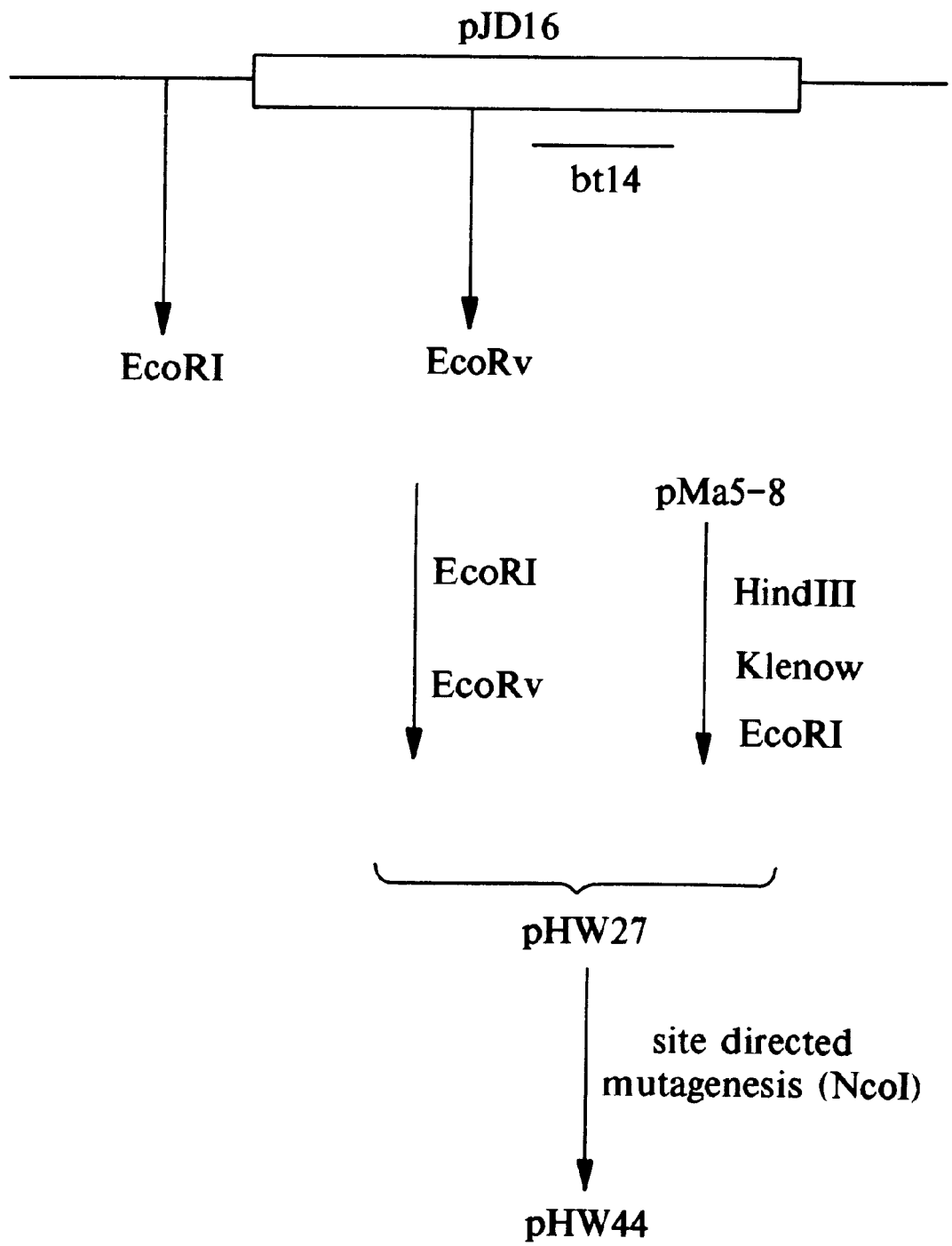
FIGS. 16A–16E schematically depict construction of pHW44, pHW67, pHW71 and pTHW94.
Figure 16B:
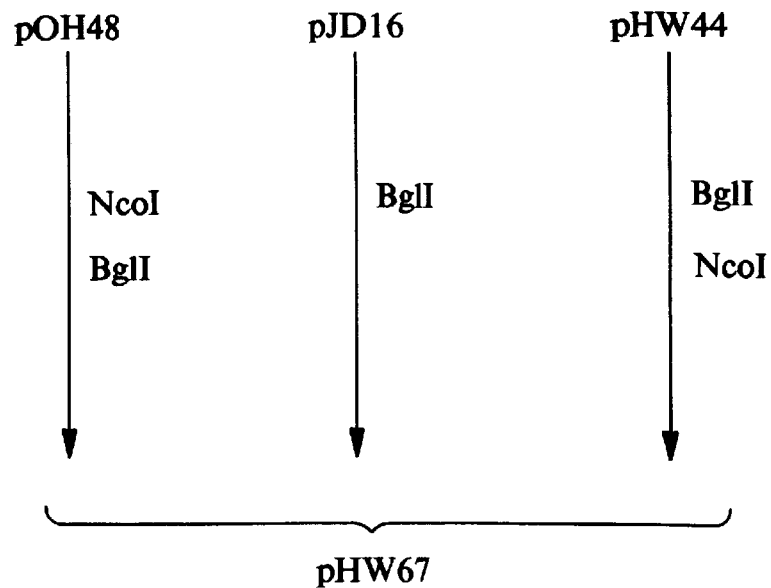
Figure 16B:
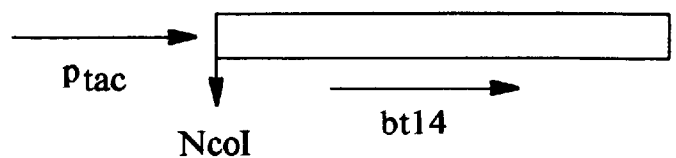
Figure 16C:
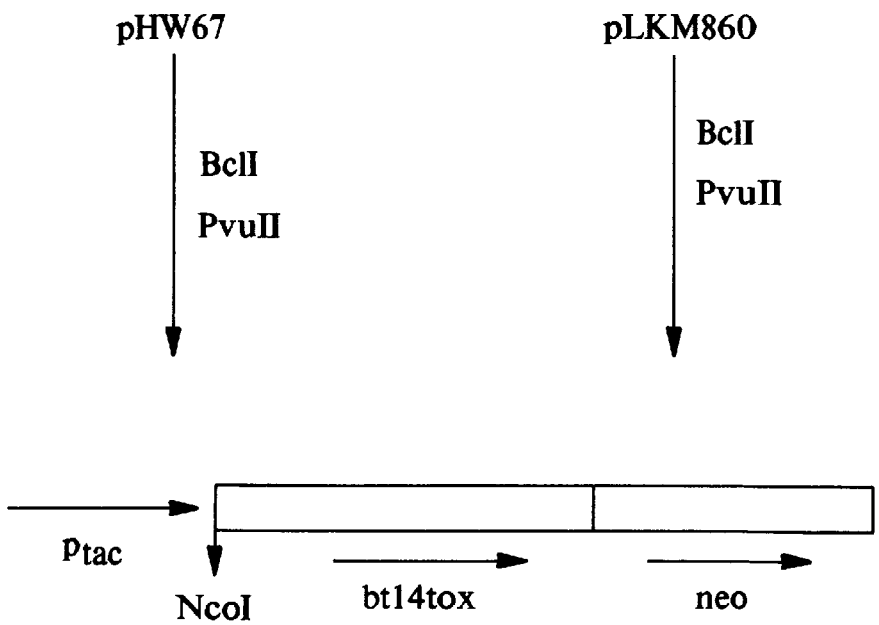
Figure 16D:
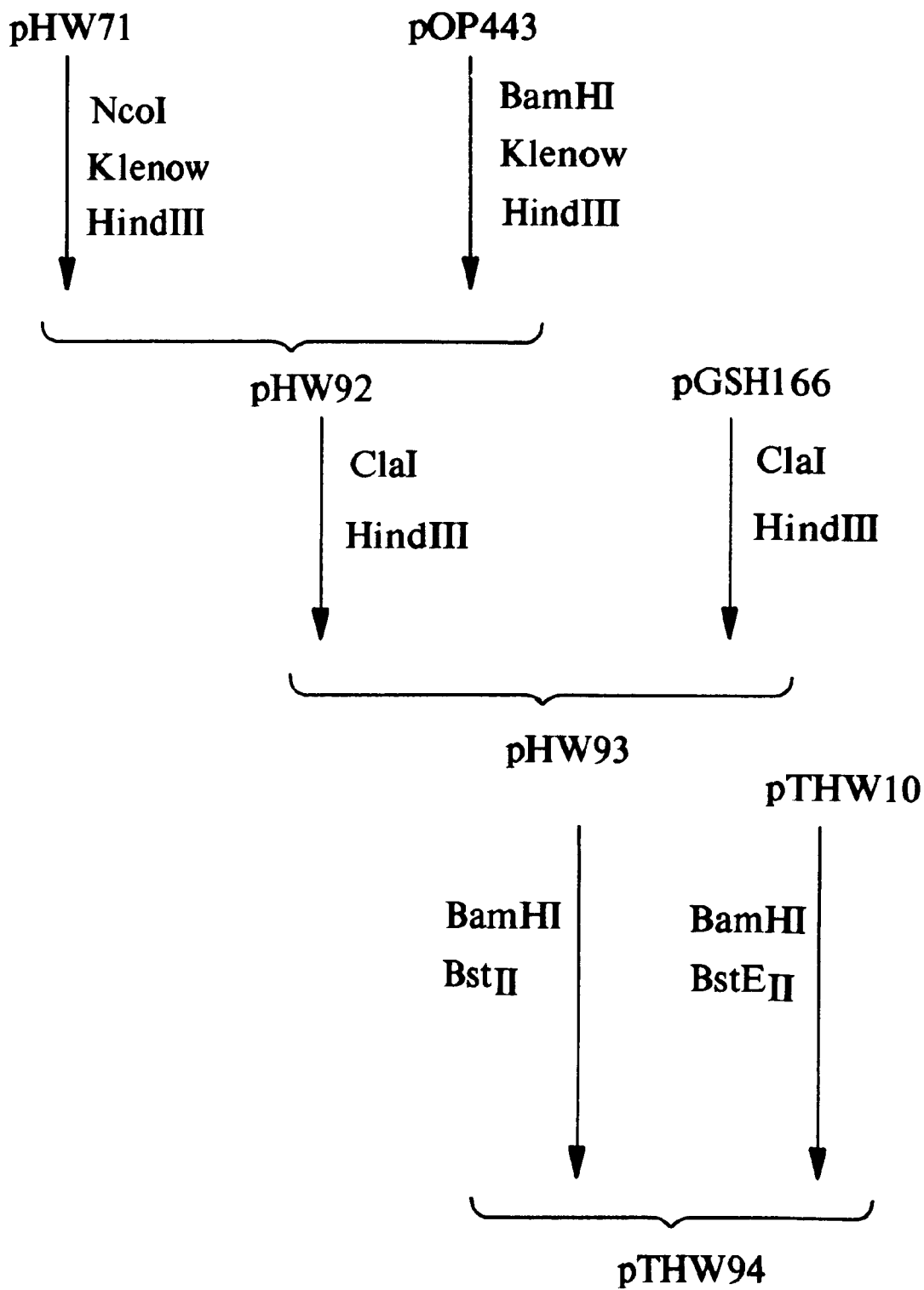
Figure 16E:
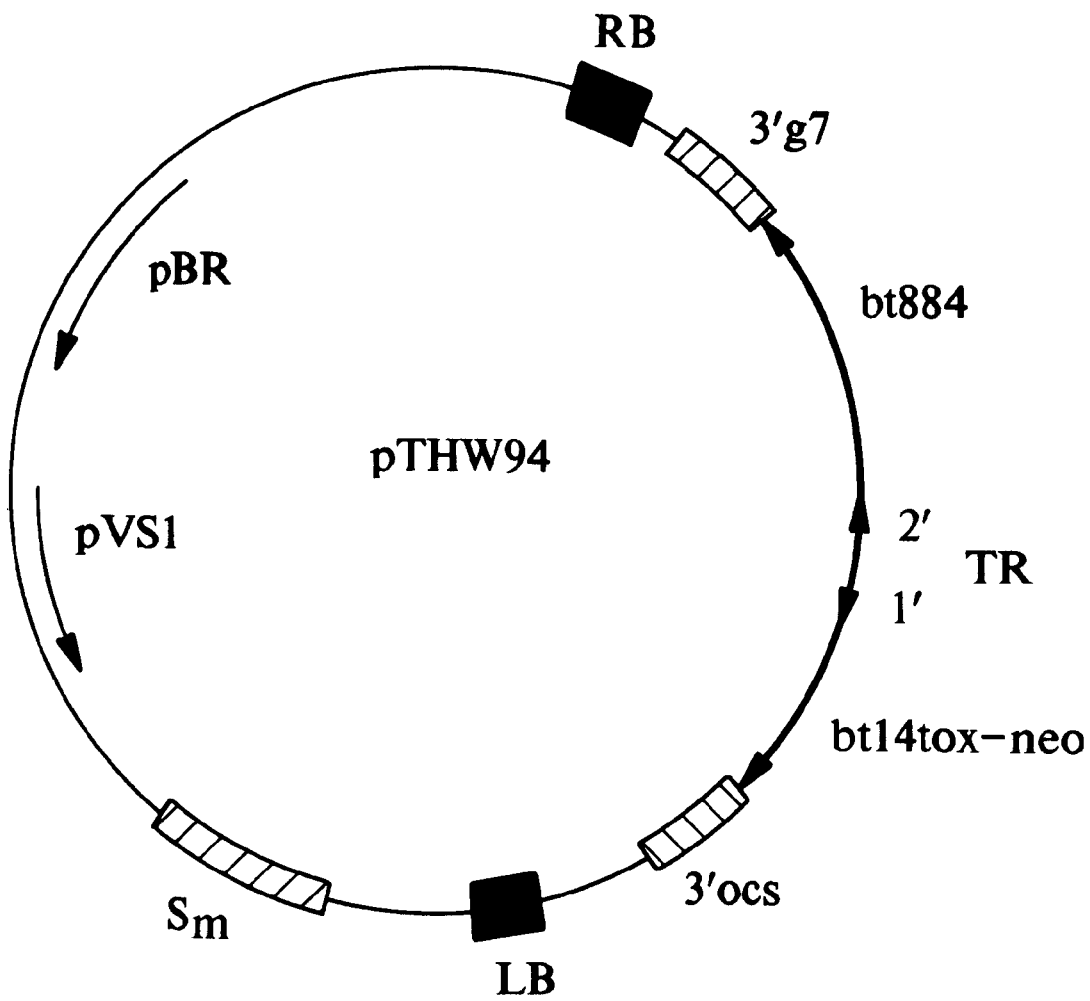
Figure 17:
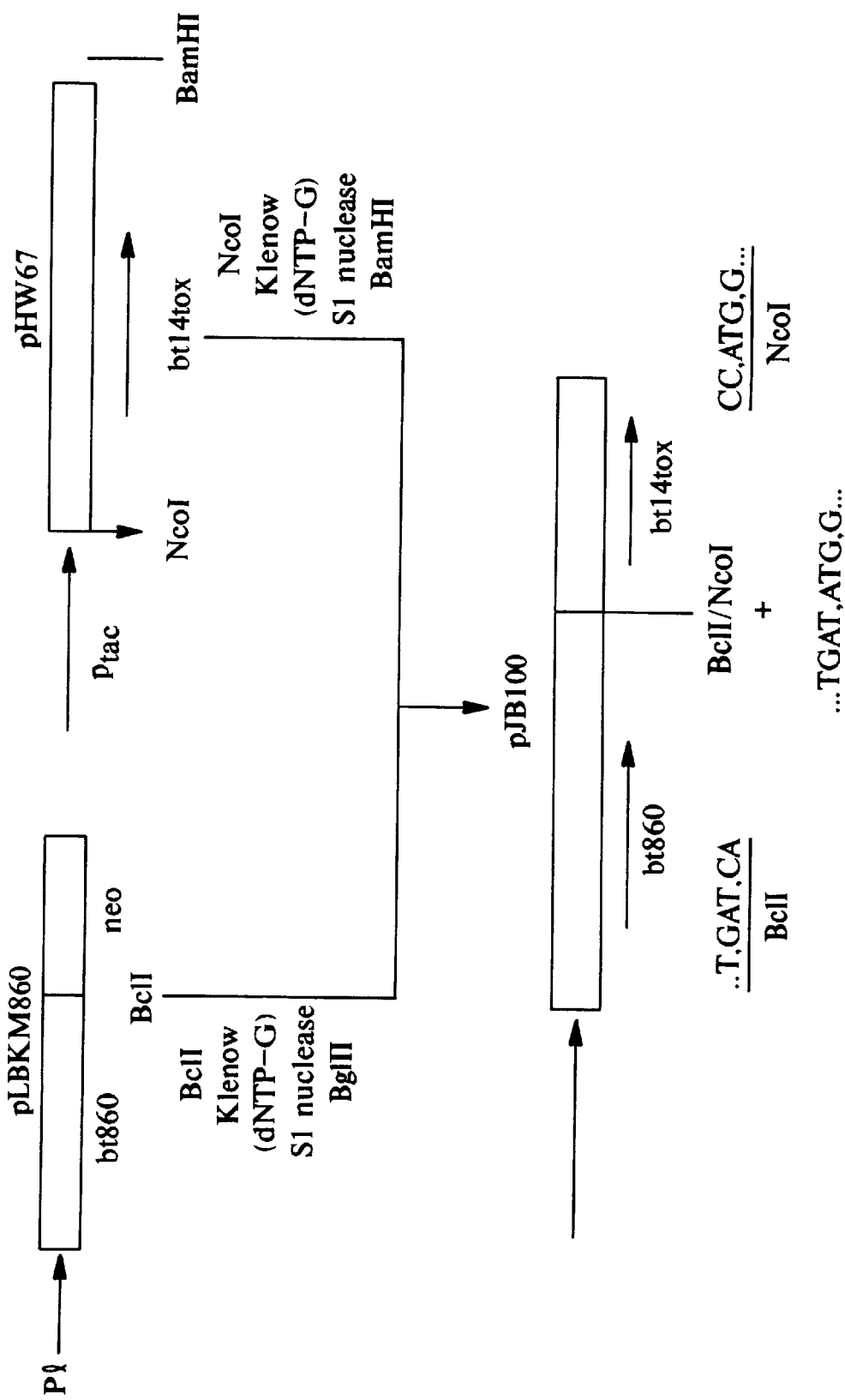
FIG. 17 depicts construction of the hybrid bt2–bt14 gene composed of a C-terminal bt2 gene fragment (bt860) encoding the toxic core of the Bt2 protoxin in frame with a C-terminal truncated bt14 gene fragment encoding the toxic core of the Bt14 protoxin.

Schematically shown in FIG. 15 are:

a) construction of pVE29: bt15 N-terminal gene fragment with NcoI site introduced at ATG initiation codon.

b) construction of pVE35: bt15 C-terminal truncated gene fragment under control of the tac promoter.

c) construction of pTHW88: binary T-DNA vector with a chimeric bt15 gene and a chimeric bar gene within the T-DNA border repeats.

In both cases, co-expression of the two ICP genes in the individual transformants was evaluated by insect toxicity tests as described in EP 0193259 and by biochemical means. Specific RNA probes allowed the quantitive analysis of the transcript levels; monoclonal antibodies cross-reacting with the respective gene products allowed the quantitative analysis of the respective gene products in ELISA tests (EP 0193259); and specific DNA probes allowed the characterization of the genomic integrations of the bt2 and bt15 genes in the transformants. It was found that the transformed tomato plants simultaneously expressed both the bt2 gene (8.1 ng/mg) and the bt15 gene (7.6 ng/mg) as measured by ELISA, which would prevent or delay development of resistance of M. sexta to the insecticidal effects of the Bt2 and Bt15 toxins, being expressed.

These procedures also could be applied when one or both ICP genes are part of a hybrid gene. For example, the same strategy as described above could be followed with the plasmid vectors pGSH152, containing a chimeric truncated bt2-neo hybrid gene under control of the TR2' promoter, and pTHW88 in suitable Agrobacterium strains.

EXAMPLE 10

Separate transfer of two ICP genes to the nuclear genome of separate plants in independent transformation events and subsequent combination in a single plant through crossing.

Tobacco plants have been transformed with either the bt18 gene or the bt15 gene by applying the same cloning strategies as described in EP 0358557 and EP 193259, respectively. For both genes, the plants were transformed with plant expression vectors containing either the truncated bt18 or bt15 gene, which just encode the Bt18 or Bt15 toxin, respectively.

The mortality rate of Spodoptera littoralis larvae feeding on the transformed plants is significantly higher than the mortality rate of larvae fed on untransformed plants.

The bt18-transformed plant, which is homozygous for the bt18 gene, is then crossed with the bt15 -transformed plant, which is homozygous for the bt15 gene. After selfing, a plant homozygous for both genes is obtained.

The resulting tobacco plants, expressing both the bt18 and bt15 genes, delay significantly development of resistance by S. littoralis to either the Bt18 or Bt15 toxin expressed by the plants.

EXAMPLE 11
Transfer of two chimeric ICP genes linked within the same DNA to the genome of plant cells The strategy used is based on the organization of two independent chimeric ICP genes between the T-DNA border repeats of a single vector. Binding studies indicated that the Bt2 and Bt14 toxins are two non-competitively binding ICPs with insecticidal activity towards *Pieris brassicae*. For expression in plants, both the bt2 and bt14 genes can be co-expressed to prevent insect resistance development. For the design of a plasmid vector with each ICP gene under the control of a separate promoter, two possibilities can be envisaged: 1) three chimeric constructs carrying the truncated bt2 and bt14 genes and a selectable marker, respectively; or 2) a hybrid of a truncated gene fragment (bt2 or bt14) and the neo gene can be used in combination with a truncated bt14 or bt2 gene.

This Example describes the construction of the vector pTHW94 for plant transformations carrying the following chimeric ICP genes between the T-DNA border repeats: a truncated bt2 gene fragment under the control of the TR2' promoter and a hybrid truncated bt14-neo gene under the control of the TR1' promoter. The 3' end of the T-DNA gene 7 and octopine synthase, respectively, provide information for proper 3' end formation. pTHW94 has been deposited at the DSM under accession no. 5514 on Aug. 28, 1989.

Schematically shown in FIG. 16 are the:

a) construction of pHW44: bt14 N-terminal gene fragment with NcoI site introduced at ATG initiation codon.

b) construction of pHW67: reconstruction of the bt14 gene under the control of the tac promoter.

c) construction of pHW71: construction of a hybrid truncated bt14-neo gene under the control of the tac promoter.

d) construction of pTHW94: binary T-DNA vector with a chimeric bt14 gene and a chimeric bt2 gene within the T-DNA border repeats.

The pTHW94 vector is mobilized into the Agrobacterium strain C58C1Rif (pMP90) which is used to transform *Brassica napus* according to the procedure described by De Block et al. (1989). Transformants are selected on Km, and regenerated plants are found to express both ICP gene products in insect toxicity tests and biochemical tests.

EXAMPLE 12

Expression of two ICP genes in a hybrid construct

In order to obtain a combined and simultaneous expression of two ICP genes, truncated gene fragments encoding the toxic parts of two different ICPs can be fused in a proper reading frame and placed, as a hybrid gene, under the control of the same promoter in a chimaeric gene construct. Toxic cores from certain ICPs can be liberated from their protoxins by protease activation at the N- and/or C-terminal end. Thus, hybrid genes can be designed with one or more regions encoding protease cleavage site(s) at the fusion point(s) of two or more ICP genes.

The simultaneous co-expression of the bt2 and bt14 genes is obtained by constructing a hybrid gene composed of a truncated bt14 gene fragment fused to a truncated bt2 gene fragment. Schematically shown in FIG. 17 is the construction of such a hybrid bt2-bt14 gene with a C-terminal bt2 gene fragment (bt860) encoding the toxic core of the Bt2 protoxin in frame with a C-terminal truncated bt14 gene fragment encoding the toxic core of the Bt14 protoxin. The BclI site in the bt2 gene, localized downstream of the trypsin cleavage site, is fused in frame with the NcoI site introduced at the N-terminal end of the truncated bt14 gene fragment. To this end, the plasmids pLBKm860 (EP 0193259) and pHW67 are used. pLBKm860 contains a hybrid bt2-neo gene under control of the lambda $P_L$ promoter. The bt2 gene moiety in the hybrid gene is a C-terminal truncated bt2 gene fragment, indicated as bt860 (in FIG. 17) (see also Vaeck et al, 1987). The construction of pHW67 is described in FIG. 16. pHW67 contains a C-terminal truncated bt14 gene fragment (bt14tox) with a NcoI site at the ATG initiation codon, a translation stop codon located at the BclI site of the intact bt14 gene and a BamHI site downstream of the whole gene fragment. To fuse both gene fragments in the proper reading frame, the BclI and NcoI ends of the respective plasmids are treated with Klenow DNA polymerase and S1 nuclease as indicated in FIG. 16. The resulting plasmid pJB100 contains the hybrid bt860-bt14tox gene under control of the lambda $P_L$ promoter and directs the expression in *E. coli* of a fusion protein with the expected mobility on SDS-PAGE.

Crude extracts of the *E. coli* strain show the toxicity of the fusion protein, expressed by the strain, against *P. brassicae*. It has also been confirmed by N-terminal amino acid sequence analyses of the fusion protein produced by the *E. coli* strain that the N-terminal amino acids from the Bt14 protoxin are processed upon activation. The bt2-bt4 hybrid gene product has thus two potential protease cleavage sites.

Subsequently, this hybrid gene is inserted into a vector for plant transformations and placed under control of a suitable promoter and transferred to the genome of *brassica* (EP 0193259) where both the bt2 and bt14 genes are expressed in insect toxicity tests.

TABLE 2

| Gene | Bt strain | Host range | amino acids encoded | predicted MW (kDa) of encoded amino acids | Disclosure of nucleotide sequence |
|---|---|---|---|---|---|
| bt3 | HD-1 kurstaki | L | 1176 | 133.2 | Schnepf et al., 1985 |
| bt2 | berliner 1715 | L | 1155 | 131 | Höfte et al., 1986 |
| bt73 | HD-73 | L | 1178 | 133.3 | Adang et al, 1985 |
| bt14 | entomocidus HD-110 | L | 1207 | 138 | Brizzard and Whiteley, 1988 |
| bt15 | entomocidus HD-110 | L | 1189 | 134.8 | FIG. 14 |
| bt4 | HD-68 aizawai | L | 1165 | 132.5 | FIG. 13 |
| bt18 | darmstadiensis HD-146 | L | 1171 | 133 | EP appln. 88402241.9 |
| bt13 | BtS1, DSM4288 22/10/87 | C | 644 | 73.1 | EP appln. 88402115.5 |
| bt21 | BLPGSI208, DSM 5131, 19/1/89 | C | 651 | 74.2 | EP appln. 89400428.2 |
| bt22 | BtPGSI245, DSM 5132, 19/1/89 | C | 1138 | 129 | EP appln. 8940028.2 |
| P2 | HD-263 | L/D | 633 | 70.9 | Donovan et al, 1988 |
| Cry B2 | HD-1 | L | 633 | 70.8 | Widner and Whiteley, 1989 |

REFERENCES

Adang M., Staver M., Rocheleau T., Leighton J., Barker R. and Thompson D. (1985), Gene 36, 289–300.

Angenon et al (1989), Molecular and Cellular Biology 9, 5676–5684.
Barton K., Whiteley H. and Yang N.-S. (1987), Plant Physiol. 85, 1103–1109.
Bernard H., Remaut E., Hersfield M., Das H., Helinski D., Yanofski C. and Franklin N. (1979), Gene 5, 59–76.
Bell R. and Joachim F. (1976), Ann. Entomol. Soc. Am. 69, 365–373.
Botterman J. and Zabeau M. (1987), DNA 6, 583–591.
Bradford M. (1976), Anal. Biochem. 72, 248–254.
Brattsten L., Holyoke C., Leeper J. and Raffa K. (1986), Science 231, 1255–1260.
Brizzard B. and Whiteley H. (1988), Nucleic Acids Research 16, 4168–4169.
Deblaere R., Reynaerts A., Höfte H., Hernalsteens J.-P., Leemans J. and Van Montagu M. (1988), Methods in Enzymol. 153, 277–292.
De Block M., Botterman J., Vandewiele M., Dockx J., Thoen, Gossele V., Rao Movva, Thompson C., Van Montagu M. and Leemans J. (1987), EMBO J. 6, 2513–2518.
De Block et al (1989), Plant Physiology 91, 694–701.
De Boer H., Comstock L. and Vasser M. (1983), Proc. Natl. Acad. Sci. U.S.A. 80, 21–25.
de Framond A., Back E., Chilton W., Kayes L. and Chilton M.-D. (1986), Mol. Gen. Genet. 202, 125–131.
De Greve et al (1982), J. Mol. Appl. Genet. 1 (6), 499–511.
De La Pena and Schell (1986), Nature 325, 274–276.
Delauney A., Tabaeizadeh Z. and Verma D. (1988), Proc. Natl. Acad. Sci. U.S.A. 85, 4300–4304.
Depicker A., Herman L., Jacobs A., Schell J. and Van Montagu M. (1985), Mol. Gen. Genet. 201, 477–484.
Donovan W., Dankoscik C. and Gilbert W. (1988), J. Bacteriol. 170, 4732–4738.
Dulmage H. T and cooperators (1981), In Microbial control of pests and plant diseases 1970–1980 (Ed. H. D. Burges), Academic Press, 193–222.
Finney D. (1962), Probit Analysis (University Press, Cambridge), pp. 50–80.
Fischhoff D., Bowdish K., Perlak F., Marrone P., McCormick S., Niedermeyer J., Dean D., Kuzano-Kretzmer K., Mayer E., Rochester D., Rogers S. and Fraley R. (1987), Bio/Technology 5, 807–812.
Franck, Guilley, Jonard, Richards and Hirth (1980), Cell 21, 285–294.
French B., Maul H. and Maul G. (1986), Anal. Biochem. 156, 417–423.
Fuller F. (1982), Gene 19, 43–54.
Gardner, Howarth, Hahn, Brown-Luedi, Shepard and Messing, Nucl. Acids Res. 9, 2871–2887.
Goldberg L. and Margalit J. (1977), Mosq. News 37, 355–358.
Goldman I., Arnold J. and Carlton B. (1986), J. Invert. Pathol. 47, 317–324.
Gould F. (1988), Bioscience 38, 26–33.
Haider M., Knowles B. and Ellar D. (1986), Eur. J. Biochem. 156, 531–540.
Herrera-Estrella (1983) Nature 303, 209–213.
Hofmann C., Lüthy P., Hütter R. and Pliska V. (1988a), Eur. J. Biochem. 173, 85–91.
Hofmann C., Vanderbruggen H., Höfte H., Van Rie J., Jansens S. and Van Mellaert H. (1988b), Proc. Natl. Acad. Sci. U.S.A. 85, 7844–7848.
Höfte H., Van Rie J., Jansens S., Van Houtven A., Verbruggen H. and Vaeck M. (1988), Appl. Environ. Microbiol. 54, 2010–2017.
Höfte H., De Greve H., Seurinck J., Jansens S., Mahillon J., Ampe C., Vanderkerkhove J., Vanderbruggen H., Van Montagu M., Zabeau M. and Vaeck M. (1987), Eur. J. Biochem. 161, 273–280.
Höfte H. and Whiteley H. R. (1989), Microbiological Reviews 53, 242–255.
Hsiung H. and Becker G. (1988), Biotech. and Genetic Engin. Rev. 6, 43–65.
Hull and Howell (1987), Virology 86, 482–493.
Hunter W. and Greenwood F. (1962), Nature 194, 495–496.
Kozak M. (1987), Mol. Cell. Biol. 7, 3438–3445.
Krebbers E., Herdies L., De Clercq A., Seurinck J., Leemans J., Van Damme J., Segura M.,Gheysen G., Van Montagu M. and Vandekerckhove J. (1988), Plant Physiol. 87, 859–866.
Knowles B. and Ellar D. (1986), J. Cell. Sci 83, 89–101.
Krieg A., Huger A., Langenbruch G. and Schnetter W. (1983), Z. Ang. Ent. 96, 500–508.
Krieg A. and Langenbruch G. (1981), In: Microbial control of pests and plant diseases 1970–1980 (Ed. H. D. Burges), Academic Press, 837–986.
Kirsch K. and Schmutterer H. (1988), J. Appl. Ent. 105, 249–255.
Kronstad J., Schnepf H. and Whiteley H. (1983), J. Bacteriol. 154, 419–428.
Mahillon J. and Delcour J. (1984), J. Microbiol. Methods 3, 69–73.
Maxam A. and Gilbert W. (1980), Methods in Enzymol. 65, 499–560.
McGaughey W. (1985), Science 229, 193–195.
McGaughey W. and Beeman R. (1988), J. Econ. Entomol. 81, 28–33.
Munson P. and Rodbard D. (1980), Anal. Biochem. 107, 220–239.
Pazkowski and cooperators (1984), EMBO J 3, 2717–2722.
Peleman J., Boerjan W., Engler G., Seurinck J., Botterman J., Alliote T., Van Montagu M. and Inzé D. (1989), The Plant Cell 1, 81–93.
Remaut E., Stanssen P. and Fiers W. (1981), Gene 15, 81–93.
Rocha-Sosa et al (1989) EMBO J. 8, 23–29.
Sandler S., Stayton M., Townsend J., Ralstan M., Bedbrook J. and Dunsmuir P. (1988), Plant Mol. Biol. 11, 301–310.
Scatchard G. (1949), Ann. New York Acad. Sci. 51, 660–672.
Schocher R., Shillito R., Saul M., Pazkowski J. and Potrykus I. (1986) Bio/technology 4, 1093–1096.
Shields (1987), Nature 328, 12–13.
Schnepf H., Wong H. and Whiteley H. (1985), J. Biol. Chem. 260, 6264–6272.
Stanssens P., Remaut E. and Fiers W. (1985), Gene 36, 211–223.
Stanssens P., McKeown Y., Friedrich K. and Fritz H. (1987): "Oligo-nucleotide directed construction of mutations by the gapped duplex DNA method using the pMa/c plasmid vectors", published in the Collection of Experimental Procedures distributed at the EMBO course entitled "Directed mutagenesis and protein engineering" in July 1987 at the Max Planck Institut für Biochemie, Martinsried, FRG.
Stone T., Sims S. and Marrone P. (1989), J. Invert. Pathol. 53, 228–234.
Vaeck M., Reynaerts A., Höfte H., Jansens S., De Beukeleer M., Dean C. Zabeau M., Van Montagu M. and Leemans J. (1987), Nature 327, 33–37.
Voller, Bidwell and Barlett (1976), In: Manual of Clinical Immunology (Eds. Rose and Friedman), pp. 506–512, American Society of Microbiology, Washington
Velten J., Velten L., Hain R. and Schell J. (1984), EMBO J. 3, 2723–2730.

Velten J. and Schell J. (1985), Nucl. Acids Res. 13, 6981–6998.

Widner W. and Whiteley R. (1989), J. Bacteriol. 171, 965–974.

Wolfersberger M., Luthy P., Maurer A., Parenti P., Sacchi V., Giordana B. and Hanozet G. (1987), Comp. Biochem. Physiol. 86, 301–308.

Yanish-Perron C., Veiera J. and Messing J. (1985), Gene 33, 103–119.

We claim:

1. A plant, comprising stably inserted into the genome of its cells, two to four DNA sequences each encoding a different *Bacillus thuringiensis* (Bt) insecticidal crystal protein (ICP) or an insecticidal portion thereof, toxic to the same insect species, wherein the encoded two to four Bt ICPs or the insecticidal portions thereof bind non-competitively to the brush border membrane of the midgut epithelial cells of said same insect species; and wherein said two to four Bt ICPs or the insecticidal portions thereof are produced in said plant.

2. The plant of claim 1, wherein said two to four DNA sequences are under the control of the same promoter or different promoters directing gene expression in a cell of said plant.

3. The plant of claim 2, wherein said two to four DNA sequences are under the control of separate promoters and have separate signals for 3' end formation.

4. The plant of claim 2, wherein said two to four DNA sequences are within the same transcriptional unit and under the control of a single promoter.

5. The plant of claim 4, wherein a DNA fragment, encoding a protease-sensitive or protease-cleavable amino acid sequence, is in said same transcriptional unit as said two to four DNA sequences and intercalated between said DNA sequences.

6. The plant of claim 1, wherein said two to four DNA sequences encode insecticidal proteins having activity against Lepidoptera species.

7. The plant of claim 1, wherein said two to four DNA sequences encode insecticidal proteins having activity against Coleoptera species.

8. The plant of claim 6, wherein said two to four DNA sequences encode the following ICPs or insecticidal portion thereof: Bt12, Bt4, Bt15 and Bt18.

9. The plant of claim 2, wherein said promoter is a constitutive promoter, a nopaline synthase promoter, an octopine synthase promoter, a wound-inducible promoter, a promoter which directs gene expression selectively in plant tissue having photosynthetic activity, a promoter inducible by temperature or chemical factors, or a tissue-specific promoter.

10. The plant of claim 2, wherein said promoter is: a 35S promoter, a TR1' promoter, a TR2' promoter, a SSU promoter, a tuber-specific promoter, a stem-specific promoter or a seed-specific promoter.

11. The plant of claim 1 wherein a marker gene is in the same genetic locus as one of said DNA sequences.

12. The plant of claim 11 in which said marker gene is under the control of a different promoter directing gene expression in cells of said plant and has a different signal for 3' end formation.

13. The plant of claim 11, wherein said marker gene is fused with at least one of said two to four DNA sequences and is within the same transcriptional unit and under the control of the same promoter as one of said DNA sequences.

14. The plant of claim 11, wherein said marker gene is:

a herbicide resistance gene, a gene encoding a modified target enzyme for a herbicide having a lower affinity for the herbicide, or an antibiotic resistance gene.

15. The plant of claim 14, wherein said marker gene is: a sfr gene a sfrv gene, a gene encoding a modified 5-EPSP as a target for glyphosate, a gene encoding a modified glutamine synthetase as a target for a GS inhibitor, or a gene encoding NPTII.

16. The plant of claim 1, wherein said two to four DNA sequences are naturally-occurring or synthetic.

17. A vector suitable for preparing the plant of claim 1, comprising said two to four DNA sequences.

18. A process for producing a plant of claim 1, comprising the following steps: transforming a plant cell by introducing said two to four DNA sequences into the nuclear genome of said cell and regenerating said plant including reproductive tissue from said cell.

19. A seed of the plant of claim 1, comprising said two to four DNA sequences.

20. A plant cell, comprising stably inserted into its genome, two to four DNA sequences each encoding a different *Bacillus thuringiensis* (Bt) insecticidal crystal protein (ICP) or an insecticidal portion thereof, toxic to the same insect species, wherein the encoded two to four Bt ICPs or the insecticidal portions thereof bind non-competitively to the brush border membrane of the midgut epithelial cells of said same insect species; and wherein said two to four Bt ICPs or the insecticidal portions thereof are produced by said cell.

21. A plant cell culture comprising a plurality of the plant cells of claim 20.

* * * * *

UNITED STATES PATENT AND TRADEMARK OFFICE
CERTIFICATE OF CORRECTION

PATENT NO. : 5,908,970
DATED : June 1, 1999
INVENTOR(S) : Herman Van Mellaert et al.

It is certified that error appears in the above-identified patent and that said Letters Patent is hereby corrected as shown below:

Title, line 2, change "BT" to --Bt--.

Col. 8, line 4, change "example-according" to --example according--.

Col. 8, line 37, change "$^{125}_{I}$" to --$^{125}I$--.

Col. 8, line 39, change "$10^{31\ 10}M$" to --$10^{-10}M$--.

Col. 15, line 48, change "-35'" to -- -3' --.

Col. 15, line 50, change "ATA<u>T</u>TGA" to --ATA<u>TT</u>GA--.

Col. 16, line 53, change "0.15M" to --0.15 M--.

Col. 17, line 46, change "0.15M" to --0.15 M--.

Col. 18, line 49, change "LC50values" to --LC50 values--.

Col. 20, line 55, change "IcPs" to --ICPs--.

Col. 21, line 23, change "form" to --for--.

UNITED STATES PATENT AND TRADEMARK OFFICE
CERTIFICATE OF CORRECTION

PATENT NO. : 5,908,970
DATED : June 1, 1999
INVENTOR(S) : Herman Van Mellaert et al.

It is certified that error appears in the above-identified patent and that said Letters Patent is hereby corrected as shown below:

Col. 22, line 37, change "competitively" to --competitivity--.

Col. 22, line 62, delete "i" (between "of" and "Manduca")

Col. 28, line 53, change "BLPGSI208" to --BtPGSI208--.

Col. 29, line 34, change "In Microbial control" to --In: Microbial control--

Col. 30, line 61, insert a comma after "Dean C." and before "Zabeau M."

Col. 31, line 42, change "Bt12" to --Bt2--.

Col. 32, line 21, insert a comma between "a sfr gene" and "a sfrv gene".

Signed and Sealed this

Twenty-ninth Day of May, 2001

*Attest:*

NICHOLAS P. GODICI

*Attesting Officer*  *Acting Director of the United States Patent and Trademark Office*